United States Patent
Dai et al.

(10) Patent No.: US 6,391,916 B1
(45) Date of Patent: May 21, 2002

(54) ENEDIYNE DERIVATIVES

(75) Inventors: Wei-Min Dai, Hong Kong; Anxin Wu, Gansu; Yuk Ha Lee, Hon Kong, all of (CN); Wataru Hamaguchi, Hyogo; Sei-ichi Nishimoto, Nara, both of (JP); Ling Zhou, Hong Kong (CN); Atsushi Ishii, Shobu-machi (JP)

(73) Assignee: The Hong Kong University of Science and Technology, Hong Kong (CN)

( * ) Notice: Subject to any disclaimer, the term of this patent is extended or adjusted under 35 U.S.C. 154(b) by 0 days.

(21) Appl. No.: 09/621,517

(22) Filed: Jul. 21, 2000

(51) Int. Cl.⁷ .................... A61K 31/216; A61K 31/045; A61K 31/015; C07C 43/02; C07C 69/66
(52) U.S. Cl. ................ 514/529; 514/416; 514/443; 514/465; 514/532; 514/543; 514/546; 514/548; 514/552; 514/719; 514/729; 514/730; 548/490; 548/491; 549/49; 549/58; 549/462; 560/187; 560/188; 568/659; 568/660
(58) Field of Search .................... 514/416, 443, 514/465, 529, 532, 543, 546, 548, 552, 719, 729, 730; 548/490, 491; 549/49, 58, 462; 560/187, 188; 568/659, 660

(56) References Cited

PUBLICATIONS

Nicolaou and Dai, *Angew, Chem. Int. Ed. Endl.*, 30:1387 (1991).
Cortazzo and Schor, *Cancer Res.* 56:1199 (1996).
Zein et al., *Chem. Biol.* 2:451 (1995).
Zein et al., *Proc. Natl. Acad. Sci. U.S.A.* 90:8009 (1993).
Jones et al., *Org. Lett.* 2:811 (2000).
Nicolaou et al., *J. Am. Chem. Soc.*, 110:4866 (1988).
Nicolaou et al., *J. Am. Chem. Soc.*, 114:7360 (1992).
Huber and Jones, *Tetrahedron Lett.*, 35:2655 (1994).
Jones et al., *J. Chem. Soc., Chem. Commun.*, 1791 (1995).
Jones et al., *J. Am. Chem. Soc.*, 122:1937 (2000).
Beau and Crèvisy, *Tetrahedron Lett.*, 32:3171 (1991).
Dai et al., *Angew. Chem. Int. Ed. Engl.*, 35:779 (1996).
Dai et al., *J. Org. Chem.*, 64:5062 (1999).
Dai et al., *Tetrahedron Lett.*, 39:8149 (1998).
Shull et al., *J. Am. Chem. Soc.*, 118:11690 (1996).
Dai et al., *Tetrahedron Lett.*, 40:2397 (1999).
Mosman, *J. Immunol. Methods* 65:55 (1983).
Ferrari et al., *J. Immunol. Methods* 131:165 (1990).
Dai et al., *J. Org. Chem.*, 64:682 (1999).
Nicolaou and Dai, *J. Am. Chem Soc.*, 114:8908 (1992).
Nishiwaki et al., *Heterocycles*, 27:1945 (1988).
Suffert et al., *Tetrahedron Lett.* 38:5507 (1997).

*Primary Examiner*—Ba K. Trinh
(74) *Attorney, Agent, or Firm*—Mark A. Litman & Assoc. P.A.

(57) ABSTRACT

Novel $C_3$-substituted cyclodeca-1,5-diynes can be prepared through novel synthetic procedures using starting (E)-$C_3$-substituted-4-(aryl- or heteroarylmethylidene)cyclodeca-1, 5-diynes reagents. Both the $C_3$-substituted cyclodeca-1,5-diyn-3-enes and the starting reagents have improved thermal stability compared to unsubstituted counterparts.

33 Claims, 3 Drawing Sheets

ENEDIYNE DERIVATIVES

TECHNICAL FIELD

This invention relates to certain cyclic enediyne compounds and their precursor compounds, both of which have DNA cleavage, protein degrading and/or modulating antimicrobial and cytotoxic (antitumor) properties. More particularly, the invention relates to $C_3$-substituted cyclodeca-1,5-diyn-3-enes and (E)-$C_3$-substituted-4-(aryl- or heteroarylmethylidene)cyclodeca-1,5diynes, processes for preparing such compounds including a novel allylic rearrangement for converting the latter compounds into the former compounds, pharmaceutical compositions containing such compounds and their use for cleaving DNA, degrading or modulating a protein, inhibiting tumor growth, inhibiting microbial growth and treating cancer.

BACKGROUND OF THE INVENTION

The (Z)-hexa-1,5-diyn-3-ene moiety embedded in a 10-membered ring is highly strained but is a biologically important structural unit found in the naturally occurring enediyne antitumor antibiotics. See Nicolaou and Dai, *Angew. Chem. Int. Ed. Engl.*, 30:1387 (1991). It is generally believed that the enediyne core found in the naturally occurring enediyne antitumor antibiotics, such as Calicheamicin $\gamma_1^1$, is bio-reductively activated and forms a 1,4-benzenoid diradical through cycloaromatization. The resultant radical species are reported to cause DNA strand scission by abstraction of hydrogen atom(s) from the sugar-phosphate backbone. Interaction of the carbon-centered radical with peptides and proteins has been reported. Cortazzo and Schor demonstrated enediyne-induced apoptosis in an article published in *Cancer Res.* 56:1199 (1996). Damage to histones by enediynes are also known in the literature [Zein et al., *Chem. Biol.* 2:451 (1995); Zein et al., *Proc. Natl. Acad. Sci. U.S.A.* 90:8009 (1993)]. Recently, Jones et al. demonstrated that peptide radicals are generated from the interaction with enediyne-derived diradical species in an article published in *Org. Lett.* 2:811 (2000). Reactive enediynes capable of generating a 1,4-benzenoid diradical through cycloaromatization are therefore useful compounds for biomedical applications.

Synthesis of the 10-membered ring enediynes is a challenging undertaking in organic synthesis because of the high strain energy associated with the bent acetylene units. The parent cyclodeca-1,5-diyn-3-ene was first synthesized, albeit in low yield, via a Ramberg-Bäcklund reaction using KO-t-Bu at −78° C. Nevertheless, this synthetic enediyne was confirmed to exert the natural product-like biological activities in causing both DNA strand breakage and cell death [Nicolaou et al., *J. Am. Chem. Soc.*, 110:4866 (1988); Nicolaou et al., *J. Am. Chem. Soc.*, 114:7360 (1992)]. Jones and co-workers used an intramolecular carbenoid coupling reaction performed at −45° C. in the presence of LiHMDS to close the 10-membered ring with significantly improved efficiency [Huber and Jones, *Tetrahedron Lett.*, 35:2655 (1994); Jones et al., *J. Chem.Soc., Chem. Commun.*, 1791 (1995)]. Beau and Crévisy reported a synthesis of a 10-membered ring enediyne possessing a hydroxyl functionality by using the $CrCl_2$—$NiCl_2$-mediated ring closure as published in *Tetrahedron Lett.*, 32:3171 (1991). However, the monocyclic enediynes are thermally unstable and readily undergo cycloaromatization at ambient temperature or above. The half-life of cyclodeca-1,5-diyn-3-ene was reported to be 18 hours at 37° C. by Nicolaou et a. as published in *J. Am. Chem. Soc.*, 110:4866 (1988). The thermal instability of the simple unsubstituted monocyclic enediynes therefore renders their practical application difficult.

Various 10-membered ring enediynes have been synthesised which are substituted at one or more of the four —$CH_2$ positions between the two triple bonds, that is, the 7-, 8-, 9- and 10-positions. For instance, Suffert and Toussaint (*Tetrahedron Lett.*, 38(31), 5507–5510, (1997)) disclose 10-membered ring enediynes which are substituted at the 7- and 8-positions and fused with a phenyl ring at the 9- and 10-positions and Dai et al (*J. Org. Chem.*, 64,682–683, (1999)) discloses, inter-alia, (E)-3-hydroxy-4-benzylidene-10-anthraquinone-2-carbonyloxycyclodeca-1,5-diyne, 3-(1-hydroxy-1-phenyl)methyl-and 3-(1ethoxy-1-phenyl)methyl-7-anthraquinone-2-carbonyloxycyclodeca-1,5-diyn-3-ene.

SUMMARY OF THE INVENTION

It has now been discovered that certain novel $C_3$-substituted cyclodeca-1,5-diyn-3-enes have improved thermal stability compared to the parent unsubstituted compound. Moreover, these compounds can be prepared from certain novel (E)-$C_3$-substituted-4-(aryl- or heteroarylmethylidene)cyclodeca-1,5-diynes, which also have good thermal stability and act as enediyne prodrugs, by a novel method. Both the $C_3$-substituted cyclodeca-1,5-diyn-3-enes and their precursors can be used as tools for interactions with DNA and proteins and as antimicrobial and antitumor agents.

According to a first aspect of the present invention there is therefore provided a compound having a nucleus of the general formula

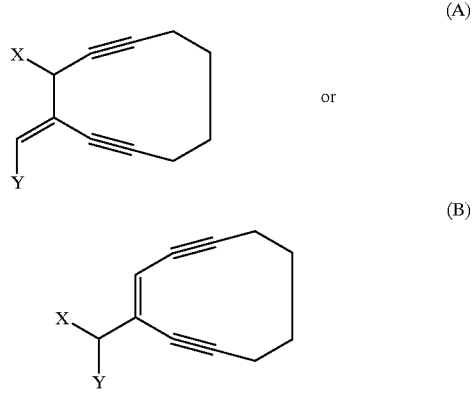

which may be substituted or, more preferably, unsubstituted, wherein

X represents a hydroxyl group or an optionally substituted alkoxy or acyloxy group; and Y represents an optionally substituted aryl or heteroaryl group; or, in the case of formula B, X and Y together with the interjacent carbon atom represent an optionally substituted heterocyclic group;

or a salt thereof. If a compound of formula (A) or (B) is substituted, it is preferred that the substituent or substituents is or are located at one or more of the 7-, 8-, 9- and 10-positions of the ring.

In a second aspect, a process for preparing compounds of the general formula A is provided which comprises either cyclizing an appropriate 10-halo-2-(aryl- or heteroarylmethylidene)deca-3,9-diyn-1-al in the presence of a first-row transition metal (II) halide, prefereably chromium (II) and/or nickel (II) chloride, or cyclizing a 2-halo- or 2-trifluoromethanesulfonate-1-(aryl- or heteroaryl)-3-(hydroxy- or alkoxy)undeca-1-en-4,10-diyne in the presence of a palladium (0) catalyst and a suitable co-catalyst, preferably copper (I) or silver (I) iodide, to form compounds of formula A in which X represents a hydroxyl group or an optionally substituted alkoxy group. If desired, compounds of formula A in which X represents a hydroxyl group can then be reacted with a suitable carboxylic acid, acid anhydride and/or acid chloride in the presence of 1,3-dicyclohexylcarbodiimide (DCC) and 4-dimethylaminopyridine (DMAP) to form compounds of formula A in which X represents an optionally substituted acyloxy group.

In a third aspect, a process for preparing compounds of the general formula B is provided which comprises reacting a compound of the general formula A in which X represents an optionally substituted acyloxy group in the presence of a lanthanide catalyst to form compounds of the general formula B in which X represents an optionally substituted acyloxy group or X and Y together with the interjacent carbon atom represent an optionally substituted heterocyclic group.

In a fourth aspect, a process for preparing compounds of the general formula B is provided which comprises reacting a compound of the general formula A in which X represents a hydroxyl group with a protic acid in the presence of a suitable alcohol or with a protic acid optionally in the presence of water to form compounds of the general formula A in which X represents a hydroxyl group or an optionally substituted alkoxy group.

In another aspect, pharmaceutical compositions are provided which comprise a carrier and, as active ingredient, a compound of the general formula A or B or a salt thereof.

Methods for inhibiting tumor growth, treating cancer, inhibiting microbial growth, cleaving DNA and degrading or modulating a protein are also provided which utilize a compound of the general formula A or B or a salt thereof.

BRIEF DESCRIPTION OF THE DRAWINGS

In the drawings forming a portion of this disclosure.

DETAILED DESCRIPTION OF THE INVENTION

Figure 1:
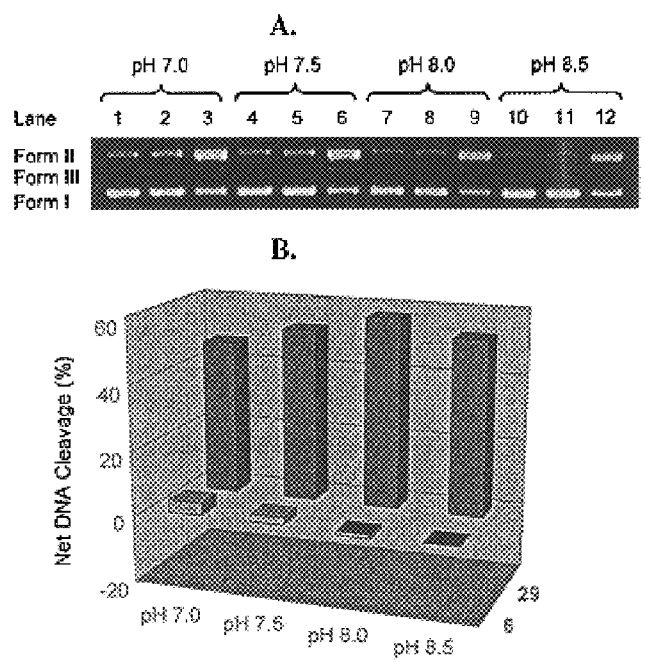
FIG. 1A is a photograph of an ethidium bromide stained 1 percent agarose gel that illustrates the cleavage of φX174 RFI (Form I) DNA by Compounds 6 and 29 at 37° C. after 72 hours TEA buffer containing 20% DMSO at various pHs. Lanes 1, 4, 7, and 10 are controls; Lanes 2,5, 8, and 11 show the results obtained with 100 μM Compound 6, respectively; Lanes 3, 6, 9, and 12 show the results obtained with 100 μM Compound 29, respectively.
FIG. 1B is a graph of the scanning densitometry results of the gel picture shown in FIG. 1A.

The primary compounds of the invention are compounds of the general formula

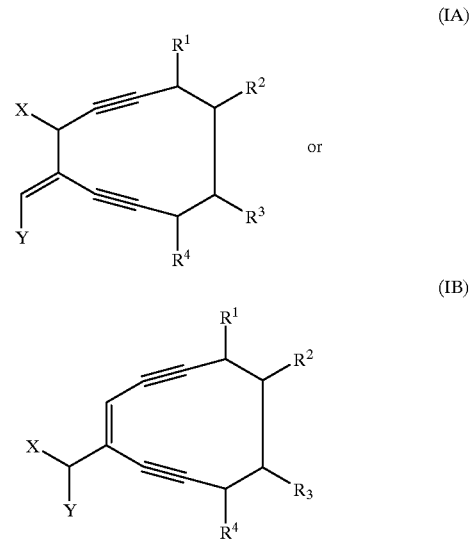

wherein
$R^1$, $R^2$, $R^3$ and $R^4$ each independently represent a hydrogen atom or a group —OR, where R represents a hydrogen atom, an optionally substituted alkyl or acyl group or a moiety which is capable of binding to a nucleic acid; and/or, R¹ and R², R² and R³ or R³ and R⁴ together with the interjacent carbon atoms represent an optionally substituted cycloalkyl group;

X represents a hydroxyl group or an optionally substituted alkoxy or acyloxy group; and Y represents an optionally substituted aryl or heteroaryl group; or, in the case of formula IB, X and Y together with the interjacent carbon atom represent an optionally substituted heterocyclic group;

or a salt thereof; with the proviso that, when R¹ represents an anthraquinone-2-carbonyloxy group, X represents a hydroxyl group or, in the case of formula IB, an ethoxy group and Y represents a phenyl group, then one of R², R³ and R⁴ represents a group OR or R² and R³ or R³ and R⁴ together with the interjacent carbon atoms represent an optionally substituted cycloalkyl group.

Suitable salts include acid addition salts and these may be formed by reaction of a suitable compound of formula A, B, IA or IB with a suitable acid, such as an organic acid or a mineral acid. Pharmaceutically acceptable salts are preferred such as acid addition salts with a mineral acid such as hydrochloric, sulfuric, phosphonic or nitric acid, or with an organic acid such as ethanoic, propanoic, maleic or an alkylsulfonic acid. Acid addition salts formed by reaction with a mineral acid are particularly preferred, especially salts formed by reaction with hydrochloric or hydrobromic acid. Suitable salts also include metal salts of compounds in which a substituent bears a terminal carboxyl group. Such metal salts are preferably formed with an alkali metal atom, such as a lithium, sodium or potassium atom, or with a group —AHal, where A is an alkaline earth metal atom, such as magnesium, and Hal is a halogen atom, preferably a chlorine, bromine or iodine atom. Sodium salts are particularly preferred.

It should also be appreciated that the compounds of general formulae A, B, IA and IB are capable of existing as different geometric and optical isomers. The present invention thus includes both the individual isomers and mixtures of such isomers.

Any alkyl group, unless otherwise specified, may be linear or branched and may contain up to 12, preferably up to 8, more preferably up to 6, and especially up to 4 carbon atoms. Preferred alkyl groups are methyl, ethyl, propyl and butyl. When an alkyl moiety forms part of another group, for example the alkyl moiety of an aralkyl group, it is preferred that it contains up to 6, especially up to 4, carbon atoms. Preferred alkyl moieties are methyl and ethyl.

An aryl group may be any monocyclic or polycyclic aromatic hydrocarbon group and may contain from 6 to 24, preferably 6 to 18, more preferably 6 to 16, and especially 6 to 14, carbon atoms. Preferred aryl groups include phenyl, naphthyl, anthryl(anthracenyl), phenanthryl and pyryl groups, especially a phenyl or naphthyl, and particularly a phenyl, group. When an aryl moiety forms part of another group, for example the aryl moiety of an aralkyl group, it is preferred that it is a phenyl, naphthyl, anthryl, phenanthryl or pyryl, especially phenyl or naphthyl, and particularly a phenyl, moiety.

An aralkyl group may be any alkyl group substituted by an aryl group. A preferred aralkyl group contains from 7 to 30, particularly 7 to 24, more preferably 7 to 18, and especially 7 to 16, carbon atoms, particularly preferred aralkyl groups being benzyl, naphthylmethyl, anthrylmethyl, phenanthrylmethyl and pyrylmethyl groups. A particularly preferred aralkyl group is a benzyl group.

A cycloalkyl group may be any saturated cyclic hydrocarbon group and may contain from 3 to 12, preferably 3 to 8, and especially 3 to 6, carbon atoms. Preferred cycloalkyl groups are cyclopropyl, cyclopentyl and cyclohexyl groups.

A heteroaryl group may be any aromatic monocyclic or polycyclic ring system which contains at least one heteroatom. Preferably, a heteroaryl group is a 5- to 18-membered, particularly a 5- to 14-membered, and especially a 5- to 10-membered, aromatic ring system containing at least one heteroatom selected from oxygen, sulphur and nitrogen atoms. Preferred heteroaryl groups include pyridyl, pyrylium, thiopyrylium, pyrrolyl, furyl, thienyl, indolinyl, isoindolinyl, indolizinyl, imidazolyl, pyridonyl, pyronyl, pyrimidinyl, pyrazinyl, oxazolyl, thiazolyl, purinyl, quinolinyl, isoquinolinyl, quinoxalinyl, pyridazinyl, benzofuranyl, benzothienyl, benzoxazolyl and acridinyl groups.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Preferably, a heterocyclic group is a 3- to 18-membered, particularly a 3- to 14-membered, especially a 5- to 10-membered, ring system containing at least one heteroatom selected from oxygen, sulphur and nitrogen atoms. Preferred heterocyclic groups include the specific heteroaryl groups named above as well as pyranyl, piperidinyl, pyrrolidinyl, dioxanyl, piperazinyl, morpholinyl, thiomorpholinyl, morpholinosulphonyl, tetrahydroisoquinolinyl and tetrahydrofuranyl groups.

An acyl group may any group of formula B—(CO)— where B represents an optionally substituted alkyl, cycloalkyl, aryl or heteroaryl group. Suitable acyl groups thus include alkanoyl, arylcarbonyl and heteroarylcarbonyl groups.

A moiety which is capable of binding to a nucleic acid includes groups which function as DNA intercalators, DNA minor groove binders, DNA binding proteins, DNA fragments, RNA fragments and monoclonal antibodies. The structure of such groups is well known to those skilled in the art. However, examples include polypyrrolecarboxamides of the general formula

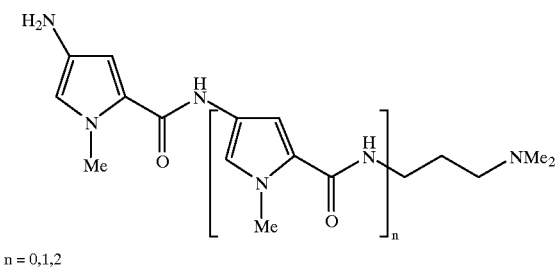

n = 0,1,2

Polypyrrolecarboxamides are well-known DNA minor groove binders. Their synthesis is described in an article by Shibuya, M. et al., *Heterocycles.* 27:1945 (1988).

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano, hydroxyl, cycloalkyl, alkyl, haloalkyl, cycloalkyloxy, alkoxy, haloalkoxy, amino, alkylamino, dialkylamino, formyl, alkoxycarbonyl, carboxyl, alkanoyl, alkylthio, alkylsulfinyl, alkylsulfonyl, alkylsulfonato, arylsulfinyl, arylsulfonyl, arylsulfonato, carbamoyl, alkylamido, aryl, aralkyl, optionally substituted aryl and optionally substituted aralkyl groups. When any of the foregoing substituents represents or contains an alkyl substituent group, this may be linear or branched and may contain up to 12, preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A halogen atom may be a fluorine, chlorine, bromine or iodine atom and any group which contains a halo moiety, such as a haloalkyl group, may thus contain any one or more of these halogen atoms.

In one preferred embodiment, $R^1$, $R^2$, $R^3$ and $R^4$ each independently represent a hydrogen atom or a group —OR, where R represents a hydrogen atom, $C_{1-12}$ alkyl, $C_{1-12}$ alkanoyl, $C_{6-18}$ arylcarbonyl or 5- to 18-membered heteroarylcarbonyl group, or a group which is capable of binding to a nucleic acid, each group being optionally substituted by one or more substituents selected from the group consisting of halogen atoms, nitro and hydroxyl groups and groups of formula —$R^5$ or —$OR^5$, where $R^5$ is a $C_{1-12}$ alkyl or $C_{7-16}$ aralkyl group each optionally substituted by one or more substituents selected from the group consisting of halogen atoms, nitro, hydroxyl, $C_{1-6}$ alkyl, $C_{1-6}$ haloalkyl, $C_{1-6}$ alkoxy and $C_{1-6}$ haloalkoxy groups.

More preferably $R^1$, $R^2$, $R^3$ and $R^4$ each independently represent a hydrogen atom or a group —OR, where R represents a hydrogen atom, $C_{1-6}$ alkyl or $C_{1-6}$ alkanoyl group, each group being optionally substituted by one or more substituents selected from the group consisting of halogen atoms, nitro, hydroxyl, $C_{1-4}$ alkoxy and $C_{1-4}$ haloalkoxy groups.

In another preferred embodiment, $R^1$ and $R^2$, $R^2$ and $R^3$ or $R^3$ and $R^4$ together with the interjacent carbon atoms represent a $C_{5-8}$ cycloalkyl, preferably a $C_{5-6}$ cycloalkyl and especially a cyclopentyl, group optionally substituted by one or more substituents selected from the group consisting of halogen atoms, nitro, hydroxyl, $C_{1-6}$ alkyl, $C_{1-6}$ haloalkyl, $C_{1-6}$ alkoxy, $C_{1-6}$ haloalkoxy and oxo groups. Halogen atoms, $C_{1-4}$ alkyl, $C_{1-4}$ haloalkyl and oxo groups are particularly preferred as optional substituents with methyl and oxo groups being especially preferred.

When only one of $R^1$, $R^2$, $R^3$ and $R^4$ does not represent a hydrogen atom, it is preferred that $R^1$ or $R^4$, especially $R^1$, does not represent a hydrogen atom. In other words, it is preferred that, when only one of the 7-, 8-, 9- and 10-positions is substituted, it is the 7- or 10-position, especially the 7-position, which is substituted.

When two of $R^1$, $R^2$, $R^3$ and $R^4$ do not represent a hydrogen atom, it is preferred that $R^1$ and $R^2$, $R^2$ and $R^3$ or $R^3$ and $R^4$, especially $R^2$ and $R^3$, do not represent a hydrogen atom. In other words, it is preferred that, when two of the 7-, 8-, 9- and 10-positions are substituted, adjacent positions, especially the 8- and 9-positions, are substituted. Compounds in which $R^1$ and $R^2$, $R^2$ and $R^3$ or $R^3$ and $R^4$ represent hydroxyl groups, that is, diols, are preferred with 8,9-diols being especially preferred. Other preferred compounds include compounds in which $R^1$ and $R^2$, $R^2$ and $R^3$ or $R^3$ and $R^4$, especially $R^2$ and $R^3$, together with the interjacent carbon atoms represent a cyclopentyl group which is substituted by two oxo groups (5-membered ring carbonate) or two $C_{1-4}$ alkyl, especially methyl, groups (5-membered ring acetal).

In some instances, $R^1$ and $R^2$, $R^2$ and $R^3$ or $R^3$ and $R^4$ together with the interjacent carbon atoms may represent a cycloalkyl group and one or both of the remaining sites $R^3$ and $R^4$, $R^1$ and $R^4$ or $R^1$ and $R^2$ may also be substituted.

It is particularly preferred that $R^1$, $R^2$, $R^3$ and $R^4$ each represent a hydrogen atom, that is, the compound is unsubstituted at the 7-, 8-, 9- and 10-positions of the diyne ring.

Preferably, X represents a hydroxyl, $C_{1-2}$ alkoxy, $C_{1-2}$ alkanoyloxy, $C_{6-18}$ arylcarbonyloxy or 5- to 18-membered heteroarylcarbonyloxy group, each group being optionally substituted by one or more substituents selected from the group consisting of halogen atoms, nitro and hydroxyl groups and groups of formula —$R^6$ or —$OR^6$, where $R^6$ is a $C_{1-12}$ alkyl or $C_{7-16}$ aralkyl group each optionally substituted by one or more substituents selected from the group consisting of halogen atoms, nitro, hydroxyl, $C_{1-6}$ alkyl, $C_{1-6}$ haloalkyl, $C_{1-6}$ alkoxy and $C_{1-6}$ haloalkoxy groups.

More preferably, X represents a hydroxyl, $C_{1-8}$ alkoxy, $C_{1-8}$ alkanoyloxy, $C_{6-14}$ arylcarbonyloxy or 5- to 10-membered heteroarylcarbonyloxy group, each group being optionally substituted by one or more substituents selected from the group consisting of halogen atoms and groups of formula —$R^6$ or —$OR^6$, where $R^6$ is a $C_{1-8}$ alkyl or $C_{7-10}$ aralkyl group each optionally substituted by one or more substituents selected from halogen atoms, nitro, $C_{1-4}$ alkoxy (especially methoxy) and $C_{1-4}$ haloalkoxy (especially trifluoromethoxy) groups.

It is particularly preferred that X represents a hydroxyl, methoxy, ethanoyloxy, methoxyethanoyloxy, propanoyloxy, dimethylpropanoyloxy, pentanoyloxy, heptanoyloxy, benzoyloxy, dimethoxybenzoyloxy, naphthylcarbonyloxy, anthracenecarbonyloxy, pyridinecarbonyloxy, benzyloxyethanoyloxy, methoxybenzyloxyethanoyloxy, nitrobenzyloxyethanoyloxy or trifluoroethoxyethanoyloxy group especially a hydroxyl, methoxy, ethanoyloxy, methoxyethanoyloxy, n-propanoyloxy, 2,2-dimethylpropanoyloxy, n-heptanoyloxy, 2,5-dimethoxybenzoyloxy, 1-anthracenecarbonyloxy, benzyloxyethanoyloxy or 4-methoxybenzyloxyethanoyloxy group.

Preferably, Y represents a $C_{6-18}$ aryl or 5- to 18-membered heteroaryl group, each group being optionally substituted by one or more substituents selected from the group consisting of halogen atoms, nitro and hydroxyl groups and groups of formula —$(Z)_m$—$(CR^7R^8)_n$—$R^9$ where m is 0 or 1, Z is an oxygen or sulfur atom, n is 0 or an integer from 1 to 6, $R^7$ and $R^8$ each independently represent a hydrogen atom or a $C_{1-6}$ alkyl group, and $R^9$ represents a hydroxyl, $C_{1-12}$ alkyl, $C_{1-12}$ haloalkyl, $C_{1-12}$ alkoxy, $C_{1-12}$ haloalkoxy, amino, $C_{1-12}$ alkylamino, di-$C_{1-12}$ alkylamino, carboxyl, $C_{1-12}$ alkanoyl, sulfanyl, $C_{1-12}$ alkylsulfanyl or 5- to 14-membered heterocyclic group or a group —$(W)_p$—$R^{10}$, where p is 0 or 1, W is an oxygen or sulfur atom and $R^{10}$ represents a silyl protecting group, a $C_{1-12}$ alkanoyl or $C_{1-12}$ alkoxycarbonyl group each optionally substituted by a $C_{6-10}$ aryl group which is itself optionally substituted by one or more substituents selected from the group consisting of halogen atoms, nitro, hydroxy, $C_{1-6}$ alkyl, $C_{1-6}$ haloalkyl, $C_{1-6}$ alkoxy and $C_{1-6}$ haloalkoxy groups, or a group of formula —CO—$R^{11}$, —CO—$OR^{12}$ or —CO—$NHR^{13}$ where $R^{11}$, $R^{12}$ and $R^{13}$ each independently represent a moiety which is capable of binding to a nucleic acid. A silyl protecting group is any group which contains a silicon atom and is capable of protecting a site from chemical attack during a specific chemical reaction.

More preferably, Y represents a $C_{6-14}$ aryl or 5- to 14-membered heteroaryl group, each group being optionally substituted by one or more substituents selected from the group consisting of groups of formula —$(Z)_m$—$(CR^7R^8)_n$—

$R^9$ where m and Z are as defined above, n is 0 or an integer from 1 to 4, $R^7$ and $R^8$ each independently represent a hydrogen atom or a $C_{1-4}$ alkyl (especially methyl) group, and $R^9$ represents a hydroxyl, $C_{1-6}$ alkyl, $C_{1-6}$ alkoxy, amino, $C_{1-6}$ alkylamino, carboxyl, sulfanyl or -5 to 10-membered heterocyclic group or a group —(W)$_p$—$R^{10}$ where p and W are as defined in claim 6 and $R^{10}$ represents a tri-($C_{1-6}$ alkyl)silyl group, a $C_{1-6}$ alkanoyl or $C_{1-6}$ alkoxycarbonyl group optionally substituted by a phenyl group which is itself optionally sustituted by one or more substituents selected from the group consisting of nitro, hydroxy, $C_{1-4}$ alkyl (especially methyl) and $C_{1-4}$ alkoxy (especially methoxy) groups, or a group of formula —CO—$R^{11}$, —CO—$OR^{12}$ or —CO—$NHR^{13}$ where $R^{11}$, $R^{12}$ and $R^{13}$ each independently represent a moiety which is capable of binding to the minor groove of DNA.

It is particularly preferred that Y represents a phenyl, methoxyphenyl, hydroxymethylphenyl, aminomethylphenyl, propylaminomethylphenyl, hexylaminomethylphenyl, sulfanylmethylphenyl, dioxoisoindolinylmethylphenyl, hydroxyethoxyphenyl, hydroxypropoxyphenyl, carboxylmethoxyphenyl, ethanoylthiomethylphenyl, dimethylpropanoyloxyphenyl, (tert-butyldimethyl)silyloxyphenyl, (tert-butyldimethyl) silyloxymethylphenyl, (tert-butyldimethyl) silyloxyethoxyphenyl, (tert-butyldimethyl) silyloxypropoxyphenyl, methoxybenzyloxycarbonylmethoxyphenyl, naphthyl, pyridyl or quinolinyl group, especially a phenyl, 4-methoxyphenyl, 2-(hydroxymethyl)phenyl, 2-(aminomethyl)phenyl, 2-((n-propylamino)methyl)phenyl, 2-((n-hexylamino)methyl)phenyl, 2-(sulfanylmethyl) phenyl, ((1,3-dioxosoindolin-2-yl)methyl)phenyl, 4-(hydroxyethoxy)phenyl, 4-(hydroxypropoxy)phenyl, 4-(carboxylmethoxy)phenyl, 2-((ethanoylthio)methyl)phenyl, 4-(2,2-dimethylpropanoyloxy)phenyl, 4-((tert-butyldimethyl)silyloxyphenyl, 2-(((tert-butyldimethyl) silyloxy)methyl)phenyl, 4-(2-((tert-butyldimethyl)silyloxy) ethoxy)phenyl, 4-(3-((tert-butyldimethyl)silyloxy)propoxy) phenyl, 4-((((4-methoxybenzyl)oxy)carbonyl)methoxy) phenyl, 1-naphthyl, 2-naphthyl, pyrid-4-yl or quinolin-4-yl group.

In an alternative preferred group of compounds of formula B or IB, X and Y together with the interjacent carbon atom represent a 3- to 18-membered heterocyclic group optionally substituted by one or more substituents selected from the group consisting of halogen atoms, nitro and hydroxyl groups and $C_{1-12}$ alkyl and $C_{1-12}$ alkoxy groups each optionally substituted by one or more substituents selected from the group consisting of halogen atoms, nitro and hydroxyl groups.

Preferably, X and Y together with the interjacent carbon atom represent a group of formula (II)

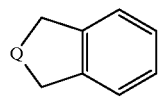

where Q represents an oxygen or sulphur atom or a group $NR^{14}$ and $R^{14}$ represents a hydrogen atom or a $C_{1-8}$ alkyl group optionally substituted by one or more substituents selected from halogen atoms and hydroxyl groups. Preferably, $R^{14}$ represents a hydrogen atom or a methyl, propyl, hexyl or hydroxyethyl group.

In one preferred subgroup of compounds of formula IA or IB, $R^1$, $R^2$, $R^3$ and $R^4$ each represent a hydrogen atom; X represents a hydroxyl group, a $C_{1-8}$ alkanoyloxy group, an arylcarbonyloxy or heteroarylcarbonyloxy group wherein the aryl or heteroaryl moiety is selected from the group consisting of phenyl, 2,5-dimethoxyphenyl, pyridyl, naphthyl and anthryl(anthracene) groups, or an alkoxyethanoyloxy group of formula —O—(O)—C($R^{15}R^{16}$)$OR^{17}$, wherein $R^{15}$ and $R^{16}$ each independently represent a hydrogen atom or a $C_{1-4}$ alkyl, preferably methyl, group and $R^{17}$ represents a benzyl, 4-methoxybenzyl, 2-nitrobenzyl, $C_{1-8}$ alkyl or 2,2,2-trifluoroethyl group; and Y represents a phenyl, 4-methoxyphenyl, 2-hydroxymethylphenyl or silyl protected analog thereof, naphthyl, pyridyl, quinolinyl or anthryl(anthracene) group.

In another preferred subgroup of compounds of formula IB, $R^1$, $R^2$, $R^3$ and $R^4$ each represent a hydrogen atom; and X and Y together represent a group (IIA)

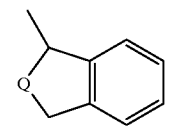

where Q represents an oxygen or sulphur atom or a group $NR^{14}$ wherein $R^{14}$ represents a hydrogen atom or a $C_{1-8}$ alkyl group.

In a further preferred subgroup of compounds of formula IA or IB, $R^1$, $R^2$, $R^3$ and $R^4$ each represent a hydrogen atom; X represents a hydroxyl group, a $C_{1-8}$ alkanoyloxy group, an arylcarbonyloxy or heteroarylcarbonyloxy group wherein the aryl or heteroaryl moiety is selected from the group consisting of phenyl, pyridyl, naphthyl and anthryl (anthracene) groups, or an alkoxyethanoyloxy group of formula —O—C(O)—C($R^{15}R^{16}$)$OR^{17}$, wherein $R^{15}$ and $R^{16}$ each independently represent a hydrogen atom or a $C_{1-4}$ alkyl, preferably methyl, group and $R^{17}$ represents a benzyl, 4-methoxybenzyl, 2-nitrobenzyl, $C_{1-8}$ alkyl or 2,2,2-trifluoroethyl group; and Y represents a group of formula

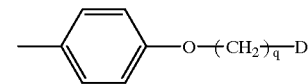

wherein q is 1, 2 or 3; and D is a hydroxyl or carboxyl group or a group of formula —O—C(O)—$R^{11}$, —C(O)—$OR^{12}$ or —C(O)—$NHR^{13}$ where $R^{11}$, $R^{12}$ and $R^{13}$ each independently represent a moiety which is capable of binding to a nucleic acid.

Compounds of general formula IA in which X represents a hydroxyl group can be prepared by cyclizing a compound of the general formula

III

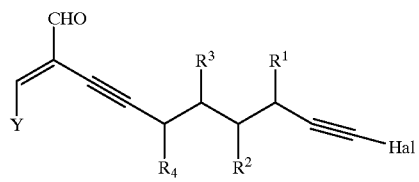

in which $R^1$, $R^2$, $R^3$, $R^4$ and Y are as defined above and Hal represents a halogen, preferably a bromine or iodine, or especially an iodine, atom, in the presence of a catalyst which preferably comprises a first-row transition metal halide, especially a chloride. Preferably, the first-row transition metal halide is of formula $MCl_2$ where M represents a first-row transition metal ion, especially a chromium (II) or nickel (II) ion. Combinations of transition metal halides may also be used with a combination of chromium (II) chloride and nickel (II) chloride being especially preferred. Preferably, a combination of 3 parts chromium (II) chloride to 1 part nickel (II) chloride is utilised. Ideally, the reaction should take place in an inert solvent, for instance, an ether solvent such as tetrahydrofuran (THF). Preferably, the reaction is carried out at room temperature, that is, 15 to 35° C., particularly about 20° C. The reaction time is preferably from 6 to 10, particularly about 8, hours.

Compounds of formulae III may be conveniently prepared by oxidising a compound of the general formula

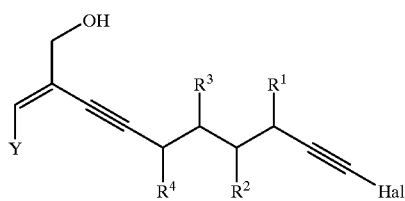

(V)

in which $R^1$, $R^2$, $R^3$, $R^4$, Y and Hal are as defined above, in the presence of a suitable oxidising agent, such as pyridinium chlorochromate (PCC). Preferably, the reaction is carried out in a suitable solvent, preferably a chlorocarbon solvent such as dichloromethane. It is preferred that the reaction is carried out at room temperature, that is, 15 to 35° C., particularly about 20° C., and that the reaction time is from 1 to 3, particularly about 2, hours.

Compounds of formula V may be conveniently prepared by halogenating a compound of the general formula

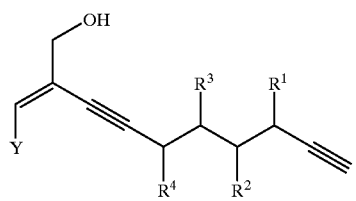

(VI)

in which $R^1$, $R^2$, $R^3$, $R^4$ and Y are as defined above, with a suitable halogenating agent, such as iodine in the presence of morpholine.

Preferably, the reaction is carried out in a suitable solvent, preferably a hydrocarbon solvent such as toluene. It is preferred that the reaction is carried out at a temperature from 30 to 60° C., preferably 40 to 50° C., and that the reaction time is from 4 to 28, particularly about 6 to 24, hours.

Compounds of formula VI may be conveniently prepared by reducing a compound of the general formula

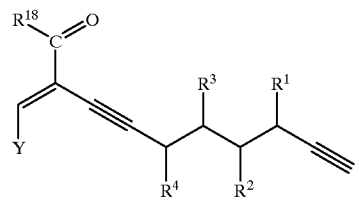

(VII)

wherein $R^1$, $R^2$, $R^3$, $R^4$ and Y are as defined above and $R^{18}$ represents a hydrogen atom or an alkoxy, preferably a $C_{1-4}$ alkoxy and especially a methoxy, group, with a suitable reducing agent such as sodium borohydride or diisobutylaluminium hydride (DIBAL). Preferably, the reaction is carried out in a suitable solvent, preferably an alcohol such as methanol or a hydrocarbon solvent such as toluene. Preferably, the reaction is carried out at a temperature from −80° C. to room temperature, preferably −78° C., to 20° C., depending on the choice of reducing agent and/or solvent. The reaction time is preferably from 20 minutes to 1½ hours, more preferably ½ to 1 hour.

Compounds of formula (VII) may be conveniently prepared by reacting a compound of formula

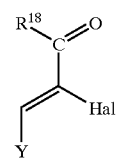

(VIII)

in which Y, $R^{18}$ and Hal are as defined above, Hal preferably being a bromine atom, with a suitable dialkyne of formula

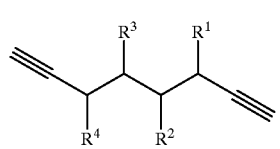

(IX)

in which $R^1$, $R^2$, $R^3$ and $R^4$ are as defined above in the presence of a suitable catalyst, such as tetrakis(triphenylphosphine)palladium(0) and copper (I) or silver (I) iodide. Preferably, the reaction is carried out in a suitable solvent such as triethylamine, tetrahydrofuran, N-ethylpiperidine, acetonitrile and mixtures thereof. Preferably, the reaction is carried out at room temperature, that is, 15 to 35° C., particularly about 20° C. The reaction time is preferably from 1 to 10 hours, especially 1½ to 8 hours, depending on the choice of solvent.

Compounds of general formula IA in which X represents a hydroxyl group or an optionally substituted alkoxy group can be prepared by cyclizing a compound of the general formula

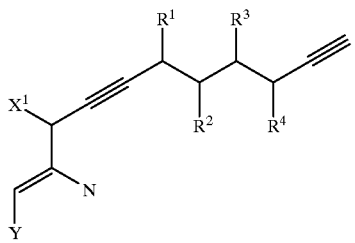 (IV)

in which $X^1$ represents a hydroxyl or an optionally substituted alkoxy group, N represents a halogen, preferably bromine or iodine and especially bromine, atom or a trifluoromethanesulfonate group, and $R^1$, $R^2$, $R^3$, $R^4$ and Y are as defined above, in the presence of a suitable catalyst. Suitable catalysts include palladium (0) catalysts and palladium (II) salts which can be converted in situ into palladium (0) compounds, for example, tetrakis(triphenylphosphine)palladium(0), dichlorobis(triphenylphosphine)palladium(II), bis(acetato)bis(triphenylphosphine)palladium(II), bis(benzonitrile)dichloropalladium(II) and a combination of palladium(II) acetate and triphenylphosphine. A co-catalyst may also be used, preferably a group IB metal (I) halide, such as copper (I) iodide or silver (I) iodide, with copper (1) iodide being especially preferred. Suitable, solvents include amines, such as triethylamine. Preferably, the reaction is carried out at a temperature of 40 to 70° C., preferably 50 to 60° C. The reaction time is preferably from ½ to 2½ hours, preferably 1 to 2 hours.

Compounds of formula IV in which $X^1$ represents a hydroxyl group may be conveniently prepared by reacting a compound of formula VIII in which $R^{18}$ represents a hydrogen atom with a monolithium acetylide formed by reacting a suitable compound of formula IX with n-butyl lithium. Suitable solvents include ethers, such as tetrahydrofuran. Preferably, the reaction is carried out at a temperature from −80 to −60° C., especially about −78° C. for, preferably, 20 minutes to 1 hour, especially 20 to 40 minutes.

Compounds of formula IV in which $X^1$ represents an optionally substituted alkoxy group may be conveniently prepared by reacting a compound of formula IV in which $X^1$ represents a hydroxyl group with a suitable alkyl halide, especially an alkyl iodide. Preferably, the reaction is carried out in the presence of a base, such as potassium hydroxide. It is also preferred that the reaction is carried out in the presence of a solvent, such as dimethyl sulfoxide (DMSO). Preferably, the reaction is carried out at room temperature, that is, 15 to 35° C., especially about 20° C. for, preferably, 3 to 7, especially 4 to 6, hours.

Compounds of formulae VIII and IX are all known compounds or can be prepared from known compounds by processes analogous to known processes.

Compounds of general formula IA in which X represents an optionally substituted acyloxy group can be prepared by reacting a compound of formula IA in which X represents a hydroxyl group with a suitable carboxylic acid, acid anhydride and/or acid chloride in the presence of a catalyst, such as 1,3-dicyclohexylcarbodiimide (DCC) and/or 4-dimethylaminopyridine (DMAP). Preferably, the reaction is carried out in the presence of a suitable solvent, preferably a chlorocarbon solvent, such as dichloroemethane. Preferably, the reaction is carried out at room temperature, that is, 15 to 35° C., especially about 20° C. The reaction time may be from 10 minutes to 28 hours, preferably 15 minutes to 24 hours depending on the reactivity of the compounds.

The carboxylic acids, acid anhydrides and acid chlorides utilised are all known compounds or can be prepared by processes analogous to known processes.

Compounds of general formula IB in which X represents an optionally substituted acyloxy group can be prepared by a novel process in which a compound of general formula IA in which X represents an optionally substituted acyloxy group is reacted in the presence of a lanthanide catalyst. Preferably, the lanthanide catalyst is of the formula L(fod)$_3$, where L represents a lanthanide metal and fod represents tris(6,6,7,7,8,8,8-heptafluoro-2,2-dimethyl-3,5-octanedionate. It is preferred that the lanthanide metal L is selected from the group consisting of europium, praseodymium, erbium and ytterbium, especially europium. Suitable solvents include chlorocarbon solvents, such as trichloromethane. Preferably, the reaction is carried out at room temperature, that is, 15 to 35° C., especially about 20° C. The reaction time may be from 20 to 50, especially about 24 to 48, hours.

Lanthanide catalysts as described above are known compounds which are commercially available.

Compounds of general formula IB in which X represents a hydroxyl group or an optionally substituted alkoxy group can be prepared by reacting a compound of general formula IA in which X represents a hydroxyl group with a protic acid in the presence of a suitable alcohol or with a protic acid optionally in the presence of water. The presence of a suitable alcohol is essential for the conversion of compounds of formula IA in which X represents a hydroxyl group into compounds of formula IB in which X represents an optionally substituted alkoxy group. However, the conversion of compounds of formula IA in which X represents a hydroxyl group into compounds of formula IB in which X represents an hydroxyl group can occur without the addition of water because water is generated in situ in the reaction. Nevertheless, it can be advantageous to add water to the reaction mixture. Suitable protic acids include camphorsulfonic acid, trifluoromethanesulfonic acid, trifluoroethanoic acid and hydrochloric acid, with camphorsulfonic acid being especially preferred. Preferably, the reaction is carried out in a solvent, preferably a chlorocarbon solvent such as dichloromethane. It is also preferred that the reaction is carried out at room temperature, that is, 15 to 35° C., especially about 20° C. The reaction time may be from 20 to 100, preferably 24 to 96, hours.

More specifically, a compound of this invention having the formula IA in which X represents a hydroxyl group was prepared according to Scheme I illustrated below.

Scheme I

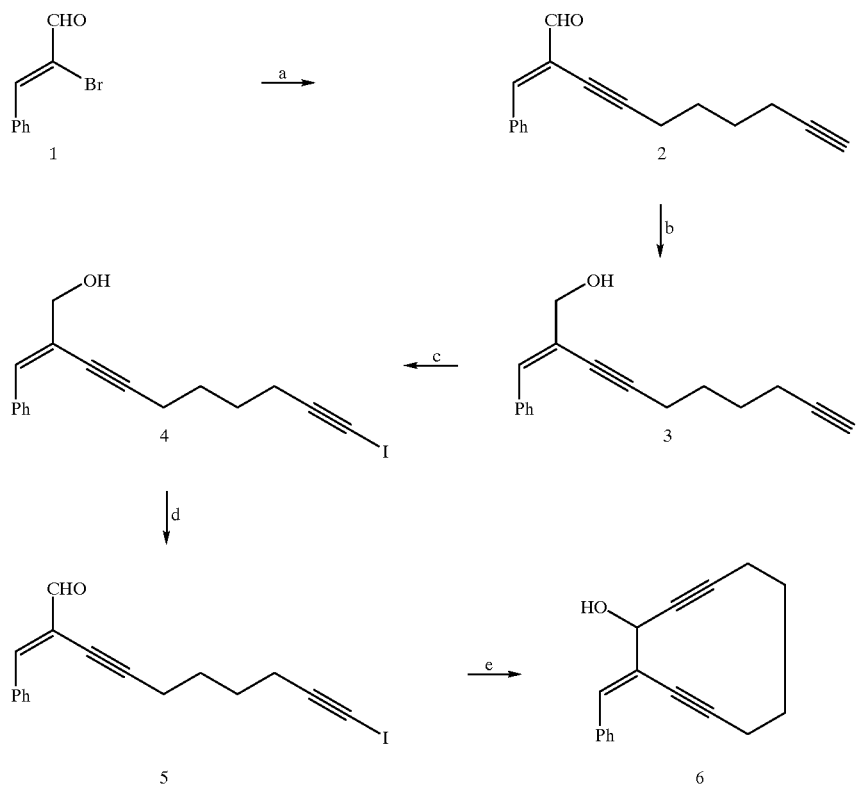

Thus, in accordance with Scheme I, the commercially available α-bromocinnamaldehyde, Compound 1, was reacted in step a with excess 1,7-octadiyne in the presence of catalytic Pd(PPh$_3$)$_4$ and CuI in a mixed triethylamine-THF (in 1:15 ratio) solvent at 20° C. for 8 hours to form Compound 2 in 91 percent yield [Dai et al., *Angew. Chem. Int. Ed. Engl.*, 35:779 (1996)]. Compound 2 was then reduced in step b by sodium borohydride in methanol at 20° C. for 30 minutes to form Compound 3 in 91 percent yield. Compound 3 was reacted in step c with 3 equivalents of iodine and 8 equivalents of morpholine in toluene at 40–50° C. for 6 hours to form Compound 4 in 89 percent yield. Compound 4 was then oxidized in step d by PCC in dichloromethane at 20° C. for 2 hours to form Compound 5 in 75 percent yield. Finally, Compound 5 was cyclized in step e in the presence of 3 equivalents of CrCl$_2$ and 1 equivalent of NiCl$_2$ in THF under high dilution condition at 20° C. for 8 hours to form Compound 6 in 29 percent yield.

Another method of preparing Compound 6 is illustrated in Scheme II.

Scheme II

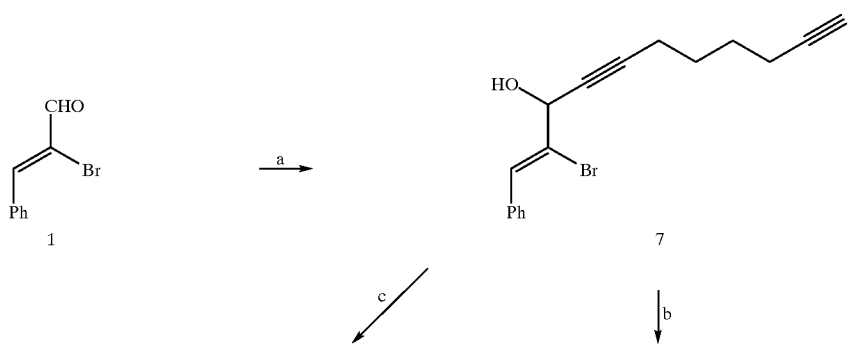

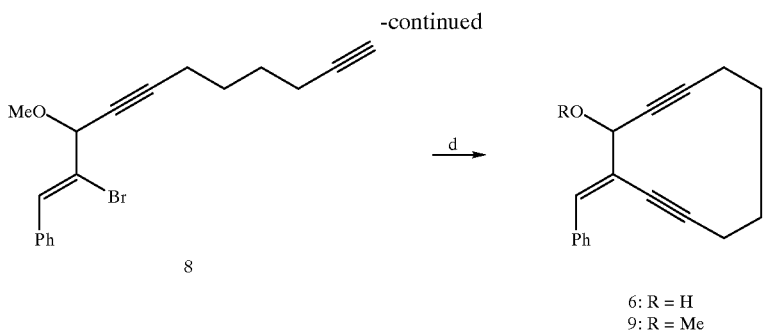

6: R = H
9: R = Me

In accordance with Scheme II, Compound 1 was reacted in step a with the mono lithium acetylide pre-formed from 1,7-octadiyne and "BuLi in THF at −78° C. for 30 minutes to form Compound 7 in 97 percent yield. Compound 7 was cyclized in step b in the presence of catalytic Pd(PPh$_3$)$_4$ and CuI in acetonitrile-diethylamine at 80–85° C. for 1 hour to form Compound 6 in 42.5 percent yield. Compound 7 was also reacted in step c with excess methyl iodide in the presence of potassium hydroxide in DMSO at 20° C. for 5 hours to form Compound 8 in 68 percent yield. Compound 8 was cyclized in the presence of catalytic Pd(PPh$_3$)$_4$ and CuI in diethylamine at 50–60° C. for 1.5 hours to form Compound 9 in 12.4 percent yield.

Another method for preparing a compound of this invention having the formula IA in which X represents a hydroxyl group is illustrated below in Scheme III. Thus, the Horner-Wadsworth-Emmons reaction of anisaldehyde (Compound 10) with trimethyl phosphonoacetate (Compound 13) in step a in the presence of "BuLi in THF at −78° C. for 5 hours gave Compound 14a in 100 percent yield [Dai et al. *J. Org. Chem.*, 64:5062 (1999)]. Similarly, reactions of 1-naphthaldehyde (Compound 11a), 2-naphthaldehyde (Compound 11b), 4-pyridinecarboxaldehyde, (Compound 12a) and 4-quinolinecarboxaldehyde (Compound 12b) with Compound 13 formed Compounds 14b–e as a mixture of trans and cis isomers in 96 to 100 percent yield. The mixture was used in the following operations and both isomers can be converted into a single compound before the ring closure. Compounds 14a–e were reacted in step b with bromine in dichloromethane at −78 to 0° C. for 1 to 5 hours to form the dibromide intermediates that were then treated with triethylamine at 20° C. for 16 to 18 hours to form Compounds 15a–e in 80 to 98 percent yield. Compounds 1 5a–e were reacted in step c with excess 1,7-octadiyne in the presence of catalytic Pd(PPh$_3$)$_4$ and CuI in a mixed N-ethylpiperidine-acetonitrile (in 1:9 ratio) solvent at 20° C. for 1.5 to 5 hours to form Compounds 16a–e in 66 to 73 percent yield. Compounds 16a–e were reduced in step d by excess DIBAL in toluene at −78° C. for 1 hour to form Compounds 17a–e in 80 to 94 percent yield. Compounds 17a–e were reacted in step e with 3 equivalents of iodine and 8 equivalents of morpholine in toluene at 40–50° C. for 6 to 24 hours to form Compounds 18a–e in 70 to 92 percent yield. Compounds 18a–e were oxidized in step f by Scheme III

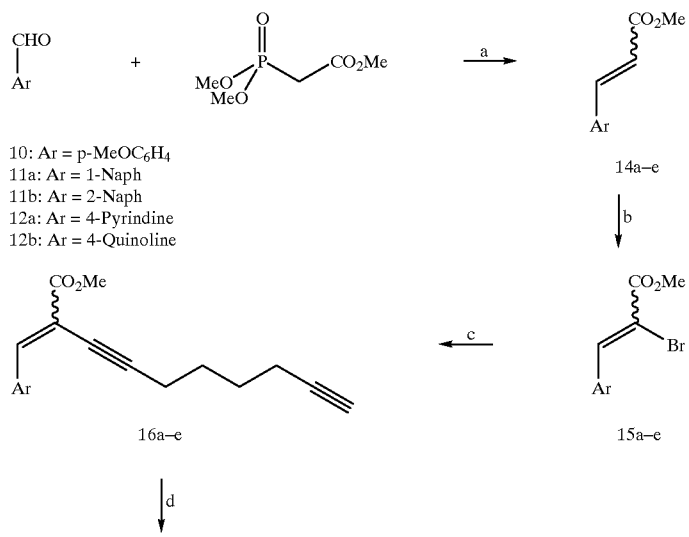

10: Ar = p-MeOC$_6$H$_4$
11a: Ar = 1-Naph
11b: Ar = 2-Naph
12a: Ar = 4-Pyrindine
12b: Ar = 4-Quinoline

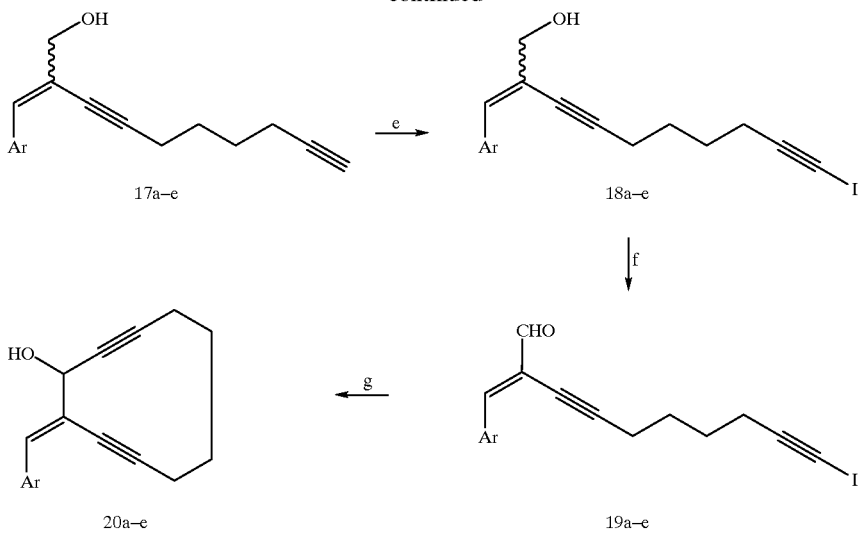

20a–e
a: Ar = p-MeOC₆H₄; b: Ar = 1-Naph; c: Ar = 2-Naph
d: Ar = 4-Pyridine; e: Ar = 4-Quinoline PCC in dichloromethane at 20° C. for 2 hours to form Compounds 19a–e as a single isomer in 66 to 88 percent yield. Control experiments using both pure isomers of Compounds 18a–e confirmed that isomerization of the undesired isomer occurred during the oxidation step. Compounds 19a–e were then cyclized in step g in the presence of 3 equivalents of CrCl$_2$ and 1 equivalent of NiCl$_2$ in THF under high dilution conditions at 20° C. for 8 hours to form Compounds 20a–e in 17 to 25 percent yield.

Another method for preparing a compound of this invention having the formula IA in which X represents a hydroxyl group is illustrated below in Scheme IV. Phthalic dicarboxaldehyde (Compound 21) was reacted in step a with Compound 13 in the presence of "BuLi in THF at −78° C. for 5 hours to give the mono aldehyde that, without isolation, was then reduced by sodium borohydride in aqueous methanol at 0° C. for 2 hours to form Compound 22 in 55

Scheme IV

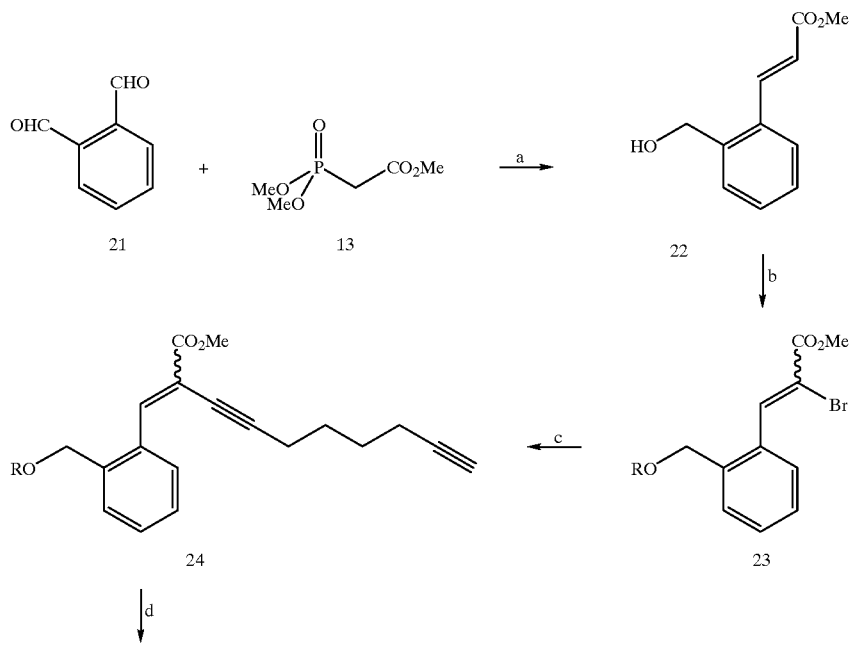

-continued

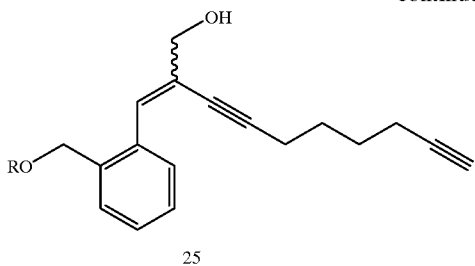

25

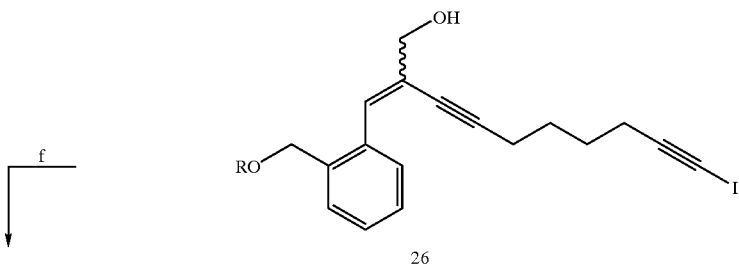

26

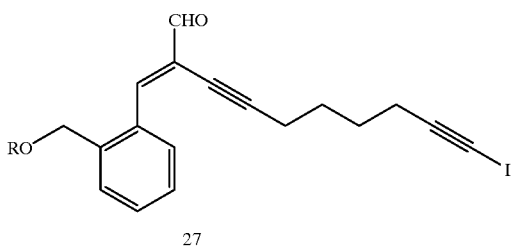

27

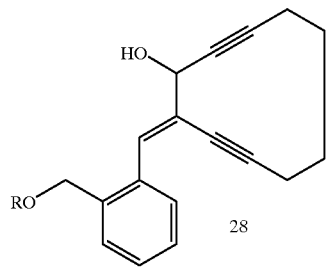

28

R = $^t$BuMe$_2$Si percent yield [Dai et al., *Tetrahedron Lett.*, 39:8149 (1998)]. The hydroxyl group in Compound 22 was protected in step b with $^t$BuMe$_2$SiCl in the presence of imidazole in DMF at 20° C. for 1.5 hours to form the silyl ether that reacted with bromine in dichloromethane chloride at 0° C. for 1 hour followed by treating with triethylamine at 20° C. for 2 hours to form Compound 23 as a mixture of isomers in 38 percent overall yield. Compound 23 was coupled in step c with excess 1,7-octadiyne in the presence of catalytic Pd(PPh$_3$)$_4$ and CuI in THF at 20° C. for 20 hours to form Compound 24 in 40 percent yield. The ester moiety in Compound 24 was reduced in step d by excess DIBAL in toluene at −78° C. for 1 hour to form Compound 25 in 77 percent yield. Compound 25 was reacted in step e with 3 equivalents of iodine and 8 equivalents of morpholine in toluene at 60° C. for 18 hours to form Compound 26 in 85 percent yield. The free allylic alcohol unit in Compound 26 was selectively oxidized in step f by PCC in dichloromethane at 20° C. for 48 hours to form Compound 27 as a single isomer in 88 percent yield. The undesired isomer underwent isomerization during the oxidation step. Compound 27 was then cyclized in step g in the presence of 3 equivalents of CrCl$_2$ and 1 equivalent of NiCl$_2$ in THF under high dilution conditions at 20° C. for 8 hours to form Compound 28 in 25.8 percent yield.

A compound of this invention having the formula IA in which X represents an acyloxy group was prepared according to Scheme V illustrated below. Compounds 6 and 20a–e were reacted in step a with excess acetic anhydride in the presence of DMAP or triethylamine in

Scheme V

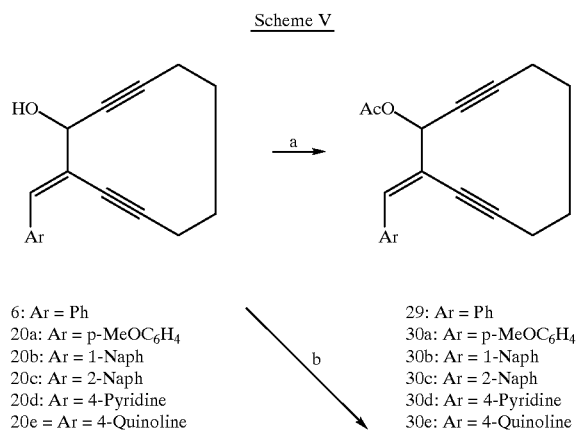

6: Ar = Ph
20a: Ar = p-MeOC$_6$H$_4$
20b: Ar = 1-Naph
20c: Ar = 2-Naph
20d: Ar = 4-Pyridine
20e: Ar = 4-Quinoline 29: Ar = Ph
30a: Ar = p-MeOC$_6$H$_4$
30b: Ar = 1-Naph
30c: Ar = 2-Naph
30d: Ar = 4-Pyridine
30e: Ar = 4-Quinoline 31: Ar = Ph
32a: Ar = p-MeOC$_6$H$_4$
32b: Ar = 1-Naph
32c: Ar = 2-Naph
32d: Ar = 4-Pyridine
32e: Ar = 4-Quinoline

33 dichloromethane at 20° C. for 2 to 3 hours to form Compounds 29 and 30a–e in 50 to 70 percent yield. Alternatively, Compounds 6 and 20a-d were reacted in step b with methoxyethanoic acid in the presence of DCC and DMAP in dichloromethane at 20° C. for 2 to 12 hours to form Compounds 31 and 32a–e in 65 to 66 percent yield. During the purification over silica gel, Compound 32a was converted into Compound 33 in 43 percent yield.

Another method for preparing a compound of this invention having the formula (I) with X being an acyloxy group is illustrated below in Scheme VI. Compound 28 was reacted in step a with excess acetic anhydride in the presence of DMAP in dichloromethane at 20° C. for 15 minutes to form Compound 34a in 82 percent yield. Alternatively, Compound 28 were reacted with methoxyethanoic acid in the presence of DCC and DMAP in dichloromethane at 20° C. for 4 hours to form Compound 34b in 77 percent yield. The silyl group in Compounds 34a,b were removed in step b by treating with PPTS in methanol at 20° C. for 16 hours to form Compounds 35a,b in 83 and 40 percent yield, respectively.

Scheme VI

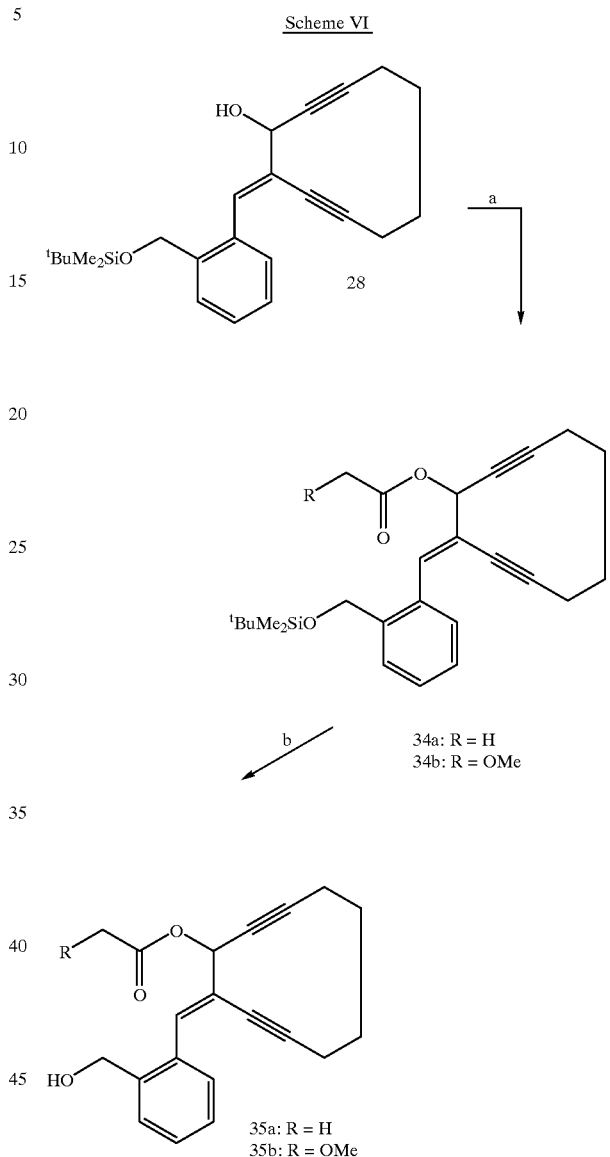

34a: R = H
34b: R = OMe

35a: R = H
35b: R = OMe

Another method for preparing a compound of this invention having the formula IA in which X represents an acyloxy group is illustrated below in Scheme VII. Compound 20b was reacted in step a with aliphatic carboxylic acids having three and eight carbon atoms in the presence of DCC and DMAP in dichloromethane at 20° C. for 4 hours to form Compounds 36 and 37 in 69 and 78 percent yield, respectively. Similarly, Compound 20b was reacted in step b with benzyloxyacetyl chloride and (p-methoxybenzyloxy) ethanoic acid in the presence of DMAP or DCC and DMAP in dichloromethane at 20° C. for 4 to 15 hours to form Compounds 38 and 39 in 73 and 71 percent yield, respectively.

Scheme VII

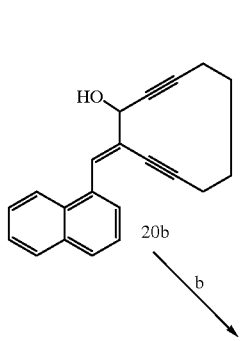
20b

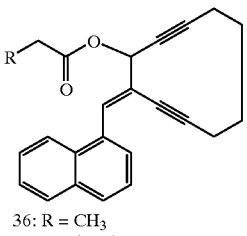
36: R = CH₃
37: R = (CH₂)CH₃

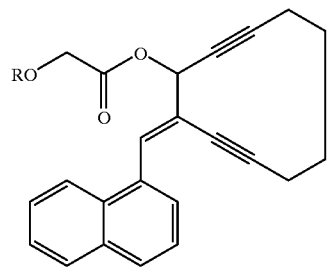
38: R = PhCH₂
39: R = pMeOPhCH₂

Another method for preparing a compound of this invention having the formula IA in which X represents an aromatic acyloxy group is illustrated below in Scheme VIII. Compound 20b was reacted in step a with 2,5-dimethoxybenzoic acid in the presence of DCC and DMAP in dichloromethane at 20° C. for 24 hours to form Compound 40 in 74 percent yield. Similarly, Compound 20b was reacted in step b with 1-anthracenecarboxylic acid in the presence of DCC and DMAP in dichloromethane at 20° C. for 24 hours to form Compound 41 in 72 percent yield.

Scheme VIII

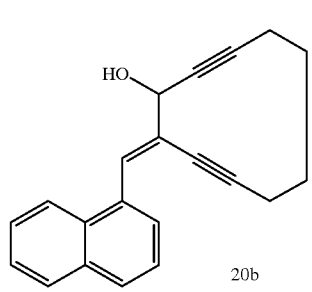
20b

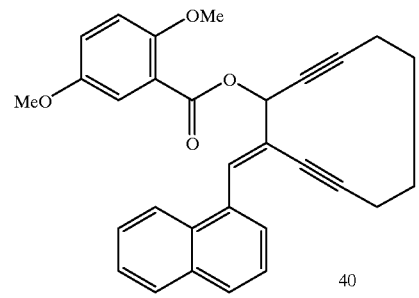
40

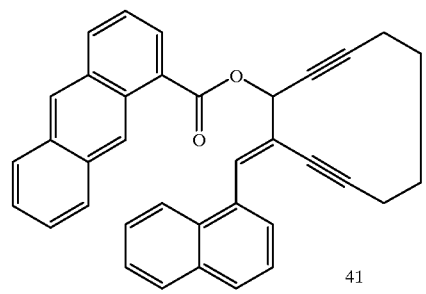
41

A compound of this invention having the formula IB in which X represents an acyloxy group was prepared according to the Scheme IX below. A lanthanide(III)-catalyzed allylic rearrangement was developed for the first time for the conversion of Compound 31 into 10-membered ring enediyne [Shull et al., *J. Am. Chem. Soc.*, 118:11690 (1996); Dai et al., *Tetrahedron Lett.*, 40:2397 (1999)]. Thus, in accordance with Scheme IX, Compound 31 was converted in step a into Compound 42 in the presence of 0.1 equivalents of Eu(fod)$_3$ in chloroform at 20° C. for 48 hours in 79 percent yield. Other lanthanide catalysts such as Pr(fod)$_3$, Er(fod)$_3$, and Yb(fod)$_3$ were used to promote the same transformation from Compound 31 into Compound 42 in 57 to 59 percent yield.

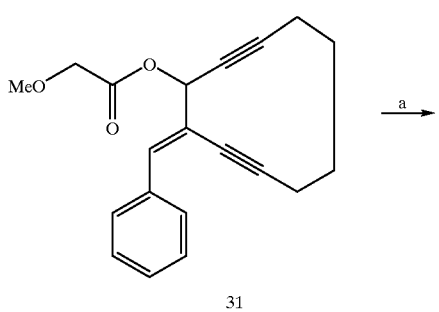

Scheme IX

| catalyst | yield |
| --- | --- |
| Pr(fod)$_3$ | 59% |
| Eu(fod)$_3$ | 79% |
| Er(fod)$_3$ | 57% |
| Yb(fod)$_3$ | 58% |

Another method for preparing a compound of this invention having the formula IB in which X represents a methoxyethanoyloxy group is illustrated below in Scheme X. Compounds 32b-e and 34b were treated in step a with 0.1 equivalents of Eu(fod)$_3$ in trichloromethane at 20° C. for 24 to 40 hours to form Compounds 43a,b, 44a,b, and 45 in 59 to 79 percent yield. These results demonstrated that the Eu(fod)$_3$-catalyzed rearrangement of allylic methoxyacetates is a general and reliable method for synthesis of 10-membered ring enediynes.

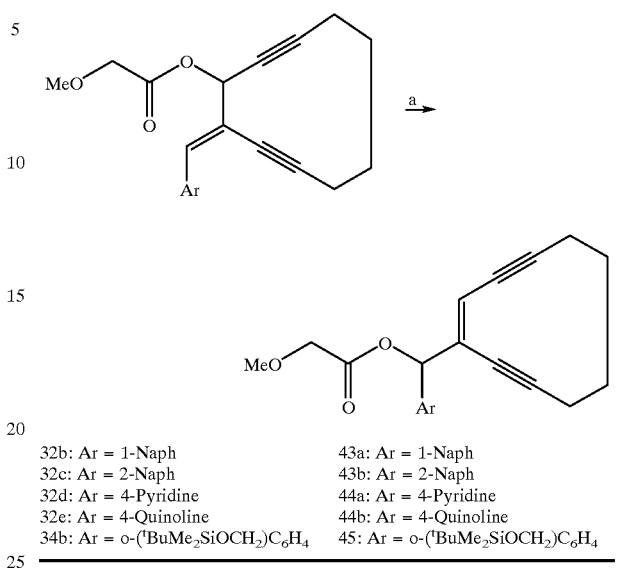

Scheme X

32b: Ar = 1-Naph  
32c: Ar = 2-Naph  
32d: Ar = 4-Pyridine  
32e: Ar = 4-Quinoline  
34b: Ar = o-($^t$BuMe$_2$SiOCH$_2$)C$_6$H$_4$ 43a: Ar = 1-Naph  
43b: Ar = 2-Naph  
44a: Ar = 4-Pyridine  
44b: Ar = 4-Quinoline  
45: Ar = o-($^t$BuMe$_2$SiOCH$_2$)C$_6$H$_4$ Another method for preparing a compound of this invention having the formula IB in which X represents an alkoxyethanoyloxy group is illustrated below in Scheme XI. Compounds 38 and 39 were treated in step a with 0.1 equivalents of Eu(fod)$_3$ in trichloromethane at 20° C. for 24 hours to form Compounds 46 and 47 in 60 and 58 percent yield, respectively. These results confirmed again that Eu(fod)$_3$-catalyzed rearrangement can be generally used for allylic alkoxyacetates.

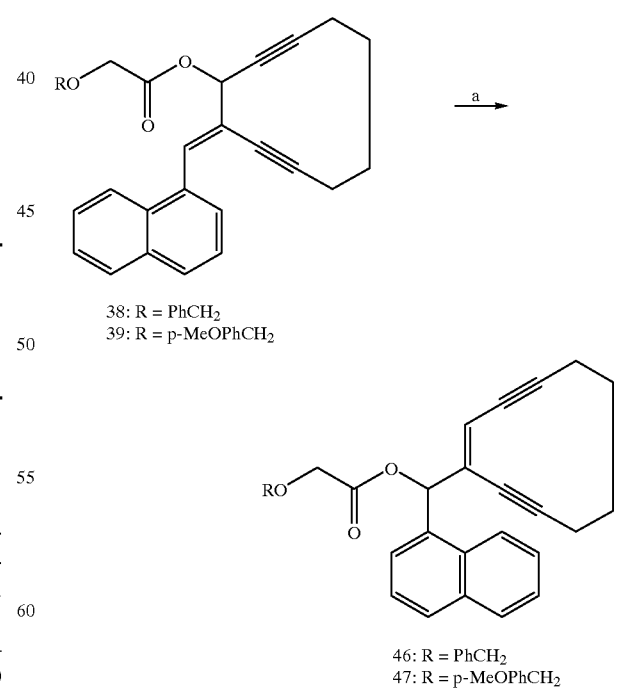

Scheme XI

38: R = PhCH$_2$  
39: R = p-MeOPhCH$_2$

46: R = PhCH$_2$  
47: R = p-MeOPhCH$_2$

Another method for preparing a compound of this invention having the formula IB in which X represents an acyloxy group is illustrated below in Scheme XII. Selective removal of the silyl group in Compound 45 was achieved in step a by treating with a catalytic amount of pyridinium p-toluenesulfonate (PPTS) in methanol at 20° C. for 22 hours to form Compound 48 in 72 percent yield. On the other hand, esters of Compound 33 were prepared in step b. Treatment with excess acetic anhydride in the presence of DMAP in dichloromethane at 20° C. for 1 hour gave Compound 49 in 80 percent yield. Alternatively, Compound 33 was reacted with methoxyethanoic acid in the presence of DCC and DMAP in dichloromethane at 20° C. for 10 hours to form Compound 50 in 75 percent yield.

Scheme XII

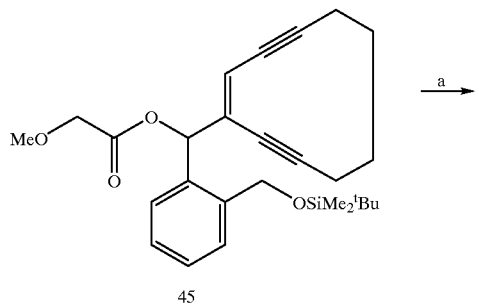

45

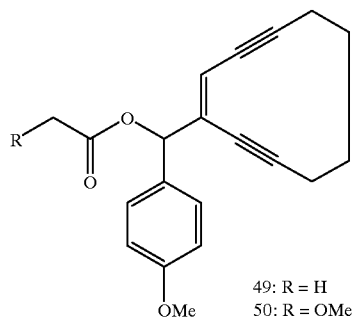

49: R = H
50: R = OMe

A compound of this invention having the formula IB in which X and Y together with the interjacent carbon atom represent a heterocyclic group containing an oxygen atom was prepared according to the Scheme XIII given below. In contrast to the reaction of Compound 34b showed in Scheme X, when Compound 34b was treated in step a with 0.1 equivalents of Eu(fod)$_3$ in trichloromethane at 20° C. for 48 hours, Compound 51 was obtained in 95 percent yield. Compound 51 was also obtained from Compound 34a after treatment with 0.1 equivalents of Eu(fod)$_3$ in trichloromethane at 20° C. for 72 hours in 91 percent yield. These results demonstrated, for the first time, that Eu(fod)$_3$ catalyzed an intramolecular $S_N2'$ displacement reaction. Complexation of the ester group with Eu(fod)$_3$ is necessary for the ring closure.

Scheme XIII

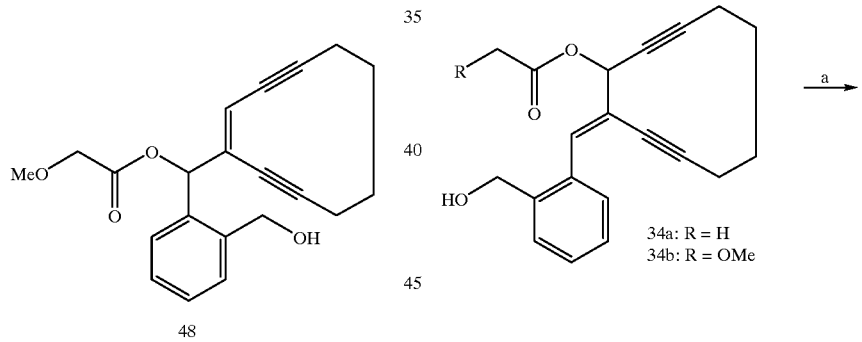

34a: R = H
34b: R = OMe

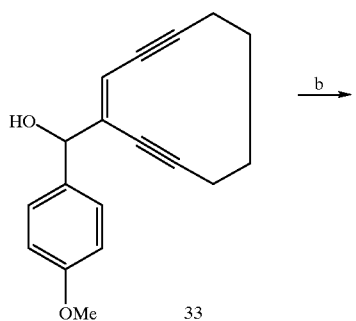

33

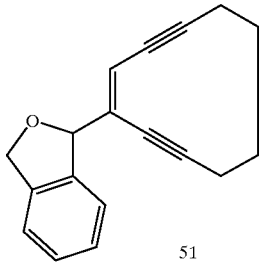

51

Another method for preparing a compound of this invention having the formula IB in which X and Y together with the interjacent carbon atom represent a heterocyclic group containing a sulfur atom is illustrated below in Scheme XIV.

Thus, Compound 28 was reacted in step a with trimethylacetyl chloride in the presence of excess triethylamine in dichloromethane chloride at 20° C. for 2 hours to form Compound 52 in 80 percent yield. The ester moiety in Compound 52 is relatively more stable and allows selective removal of the

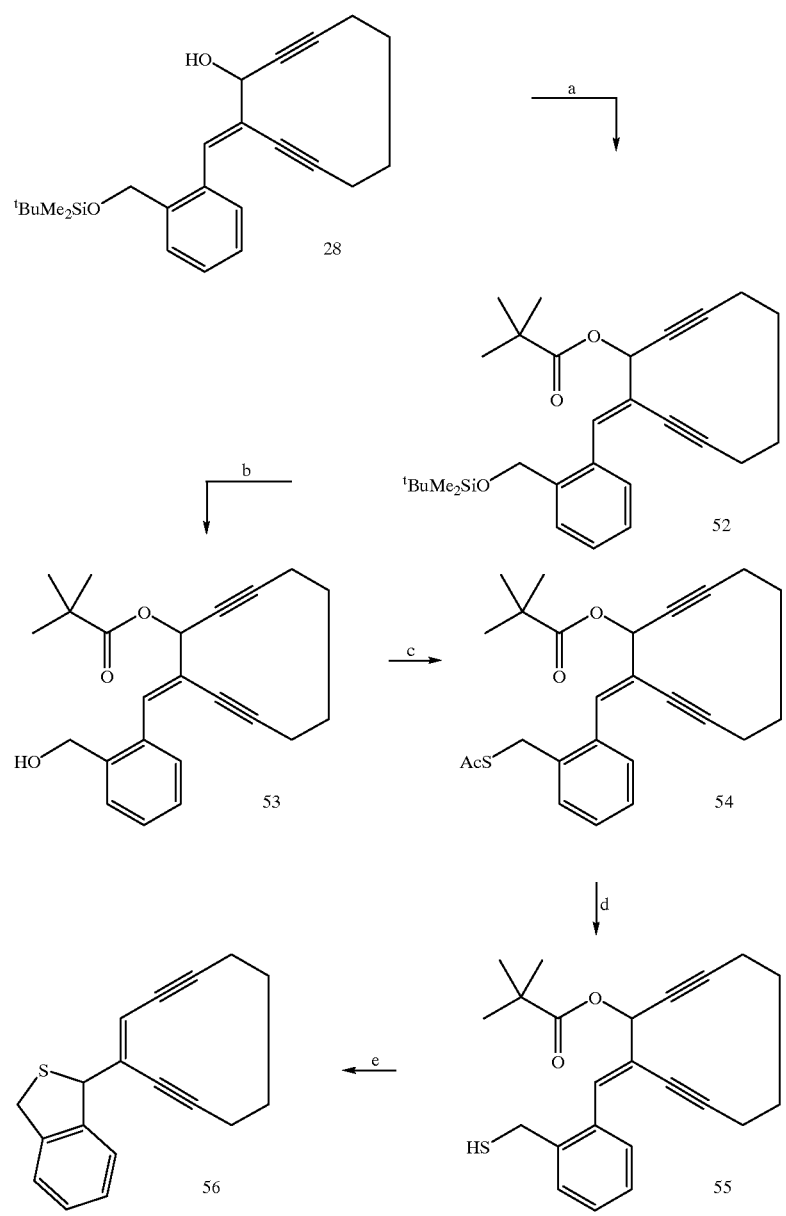

Scheme XIV silyl group. Compound 52 was treated in step b with a catalytic amount of PPTS in methanol at 20° C. for 20 hours to form Compound 53 in 70 percent yield. Compound 53 was reacted in step c with excess thioethanoic acid, diethyl azodicarboxylate, and triphenylphosphine in THF at 20° C. for 1 hour to form Compound 54 in 60 percent yield [Dai et al., Tetrahedron Lett., 39:8149 (1998)]. Compound 54 was treated in step d with potassium carbonate in aqueous methanol at 20° C. for 15 minutes to selectively remove the ethanoyl group from the sulfur atom to form Compound 55 in 60 percent yield. Finally, Compound 55 was converted in step e into Compound 56 in the presence of 0.1 equivalents of Eu(fod)$_3$ in trichloromethane at 20° C. for 89 hours to form Compound 56 in 90 percent yield.

Another method for preparing a compound of this invention having the formula IB in which X and Y together with the interjacent carbon atom represent a heterocyclic group containing a NR group is illustrated below in Scheme XV. In accordance with the Mitsunobu reaction, Compound 53 was reacted in step a with excess phthalimide, diethyl azodicarboxylate, and triphenylphosphine in THF at 20° C. for 5 hours to form Compound 57 in 65 percent yield. Compound 57 was reacted in step b with hydrazine monohydrate in Scheme XV

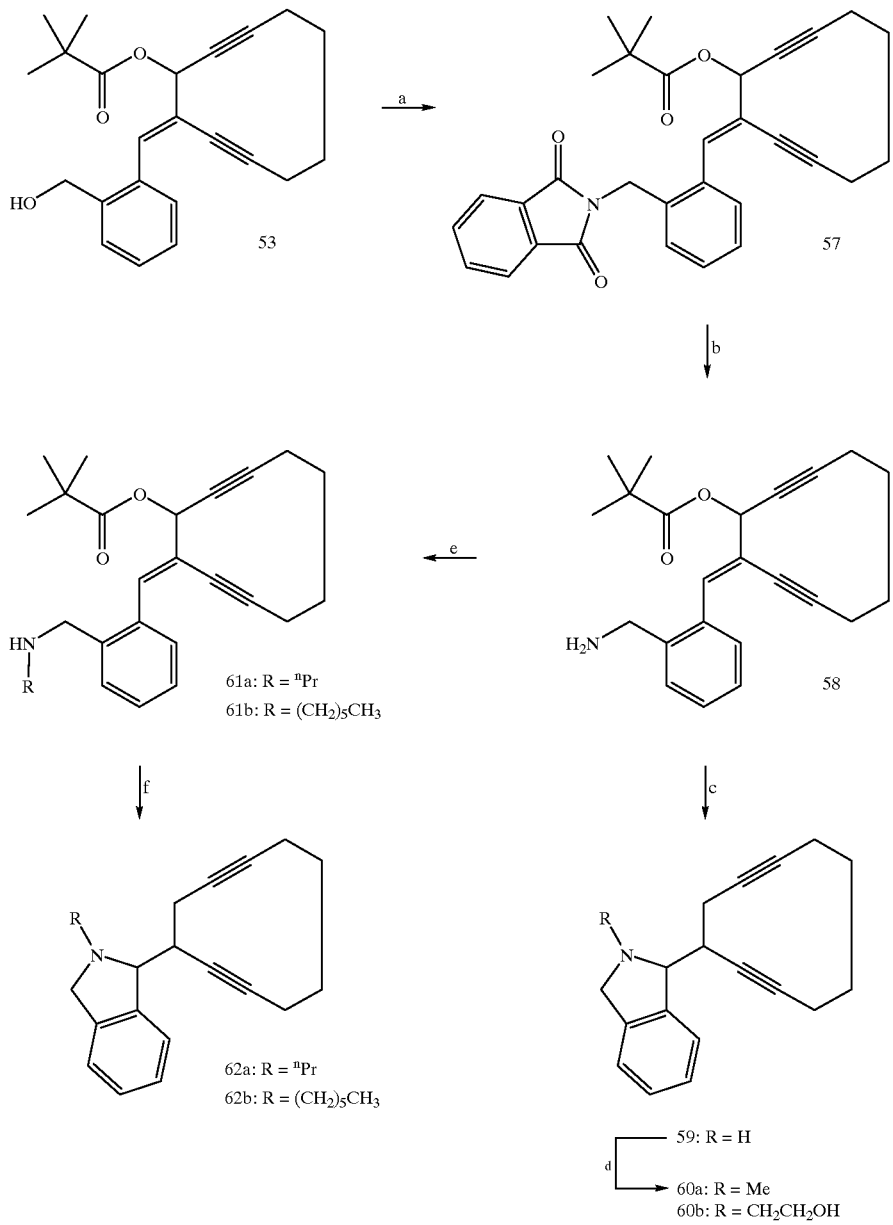

methanol at 60° C. for 10 hours to form Compound 58 in 80 percent yield. A ring closure reaction in Compound 58 was performed in step c by treating with 0.1 equivalents of Eu(fod)$_3$ in trichloromethane at 20° C. for 70 hours to form Compound 59 in 88 percent yield. Alkylation of the nitrogen atom in Compound 59 was carried out in step d with excess methyl iodide in the presence of potassium carbonate in methanol at 20° C. for 5 hours to form Compound 60a in 80 percent yield. Alternatively, Compound 59 was reacted with excess 2-bromoethanol in the presence of potassium carbonate in THF at 35° C. for 10 hours to form Compound 60b in 65 percent yield. On the other hand, Compound 58 was reacted in step e with aldehydes in the presence of sodium cyanoborohydride and ethanoic acid in THF at 20° C. for 5 hours to form the mono alkylation products, Compounds 61a,b in 70 to 85 percent yield. In the same manner, Compounds 61a,b were then treated in step f with 0.1 equivalents of Eu(fod)$_3$ in chloroform at 20° C. for 70 hours to form Compounds 62a,b in 85 to 90 percent yield.

A compound of this invention having the formula IA in which X represents a hydroxyl group was prepared according to the Schemes XVI and XVII illustrated below. The commercially available p-hydroxybenzaldehyde, Compound 63 was protected as the silyl ether in step a by treating with excess tert-butyldimethylsilyl chloride and imidazole in DMF at 20° C. for 30 minutes to form Compound 64 in 98 percent yield. Compound 64 was then reacted in step b with Compound 13 in the presence of "BuLi in THF at −78° C. to 20° C. for 20 hours to form Compound 65 in 81 percent yield. Compound 65 was reacted in step c with 10 bromine in

Scheme XVI

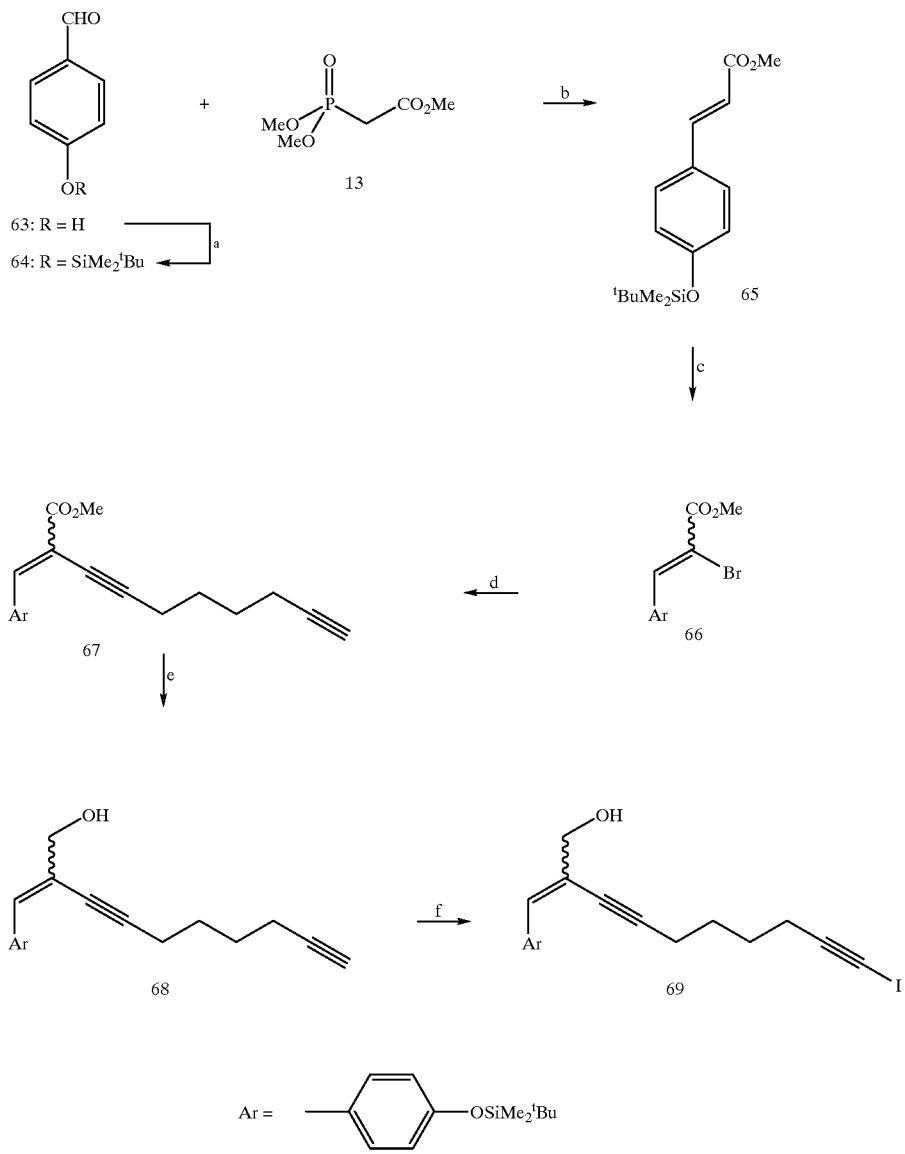

dichloromethane at 20° C. for 1 hour followed by treating with triethylamine at 20° C. for 15 hours to form Compound 66 as a mixture of trans and cis isomers in 94 percent yield. Compound 66 was reacted in step d with excess 1,7-octadiyne in the presence of catalytic $Pd(PPh_3)_4$ and CuI in a mixed N-ethylpiperidine-acetonitrile (in 1:9 ratio) solvent at 20° C. for 2 hours to form Compound 67 in 74 percent yield. Compound 67 was reduced in step e by excess DIBAL in toluene at −78° C. for 1 hour to form Compound 68 in 70 percent yield. Compound 68 was reacted in step f with 3 equivalents of iodine and 8 equivalents of morpholine in toluene at 60° C. for 15 hours to form Compound 69 in 76 percent yield.

As illustrated in Scheme XVII, Compound 69 was oxidized in step a by PCC in dichloromethane at 20° C. for 2 hours to form Compound 70 as a single isomer in 70 percent yield. Removal of the silyl group was achieved in step b by treating Compound 70 with tetrabutylammonium fluoride (TBAF) in THF at 0° C. for 10 minutes to give Compound 71 in 85 percent yield. Compound 71 was deprotonated in step c by using NaH in THF at 0° C. followed by reacting with Compound 72 [Nicolaou and Dai, *J. Am. Chem. Soc.,* 114:8908 (1992)] to form Compound 73 in 78 percent yield. Compound 73 was cyclized in step d in the presence of 3 equivalents of $CrCl_2$ and 1 equivalent of $NiCl_2$ in THF under high dilution conditions at 20° C. for 8 hours to form Compound 74a in 30 percent yield. Similarly, Compound 74b was obtained from Compound 70 in step e in 24 percent yield. Compounds 74a,b were then treated in step f with excess acetic anhydride in the presence of DMAP at 20° C. for 3 hours to form Compounds 75a,b in 72 and 65 percent yield, respectively.

Scheme XVII
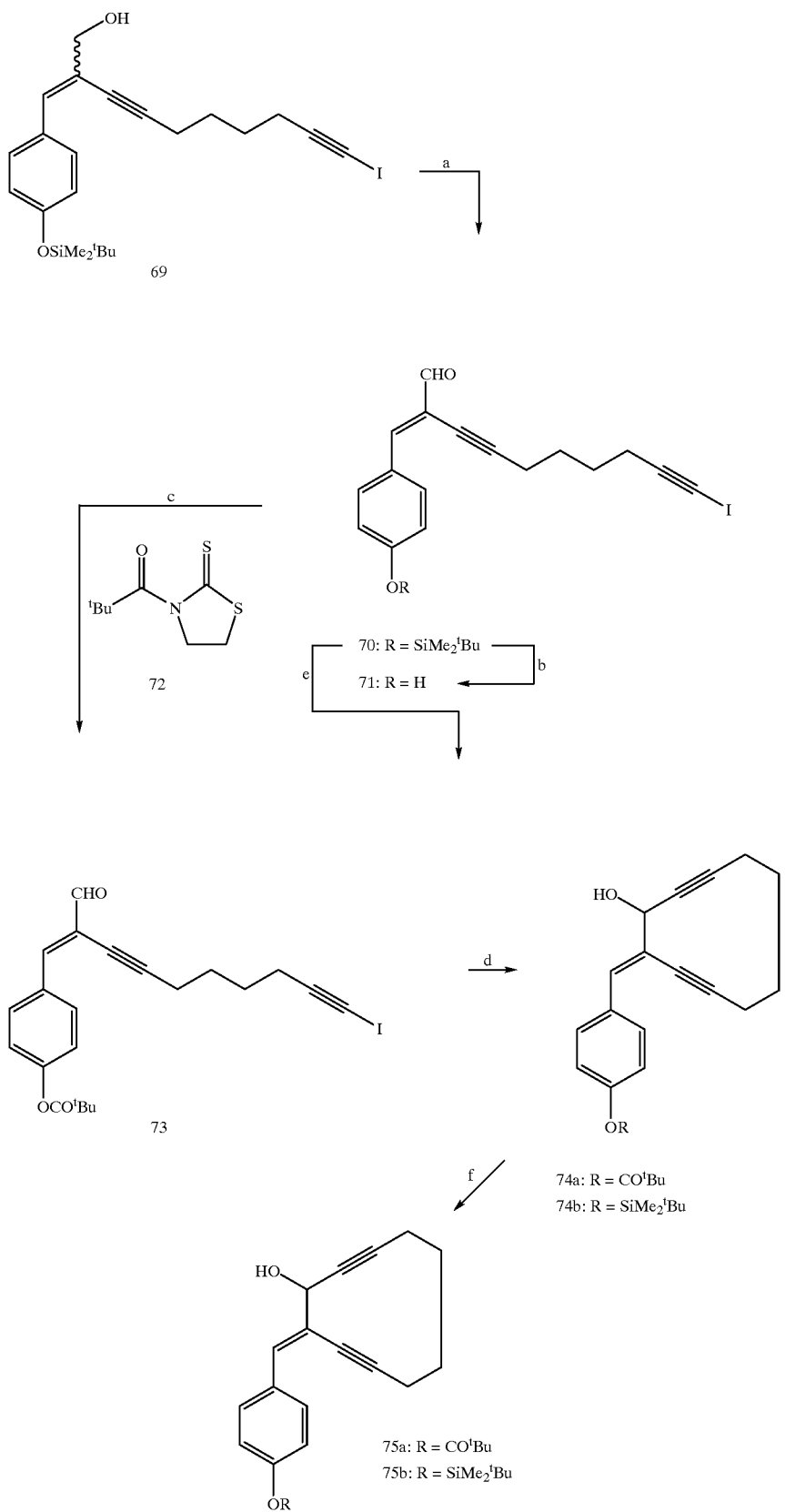

Another method for preparing a compound of this invention having the formula IA in which X represents a hydroxyl group is illustrated in Scheme XVIII below. Compound 71 was reacted in step a with Compound 76a or 76b in the presence of potassium carbonate in THF at 20° C. for 40 hours to form Compound 77a or 77b in 70 and 75 percent yield, respectively. Compound 77a or 77b was cyclized in step b in the presence of 3 equivalent of $CrCl_2$ and 1 equivalent of $NiCl_2$ in THF under high dilution conditions at 20° C. for 8 hours to form Compound 78a or 78b in 35 and 41 percent yield, respectively.

Compound 78b was reacted with methoxyethanoic acid in the presence of DCC and DMAP in dichloromethane at 20° C. for 10 hours to form Compound 80 in 65 percent yield. The p-methoxybenzyl group in Compounds 79 and 80 were removed in step b by dichlorodicyanoquinone (DDQ) in $CH_2Cl_2$—$H_2O$ to form Compounds 81 and 82 in 80 to 85 percent yield. Similarly, Compound 78a was reacted in step c with excess acetic anhydride in the presence of DMAP in dichloromethane at 20° C. for 2 hours to form Compound 83 in 63 percent yield. Alternatively, Compound 74 was reacted Scheme XVIII

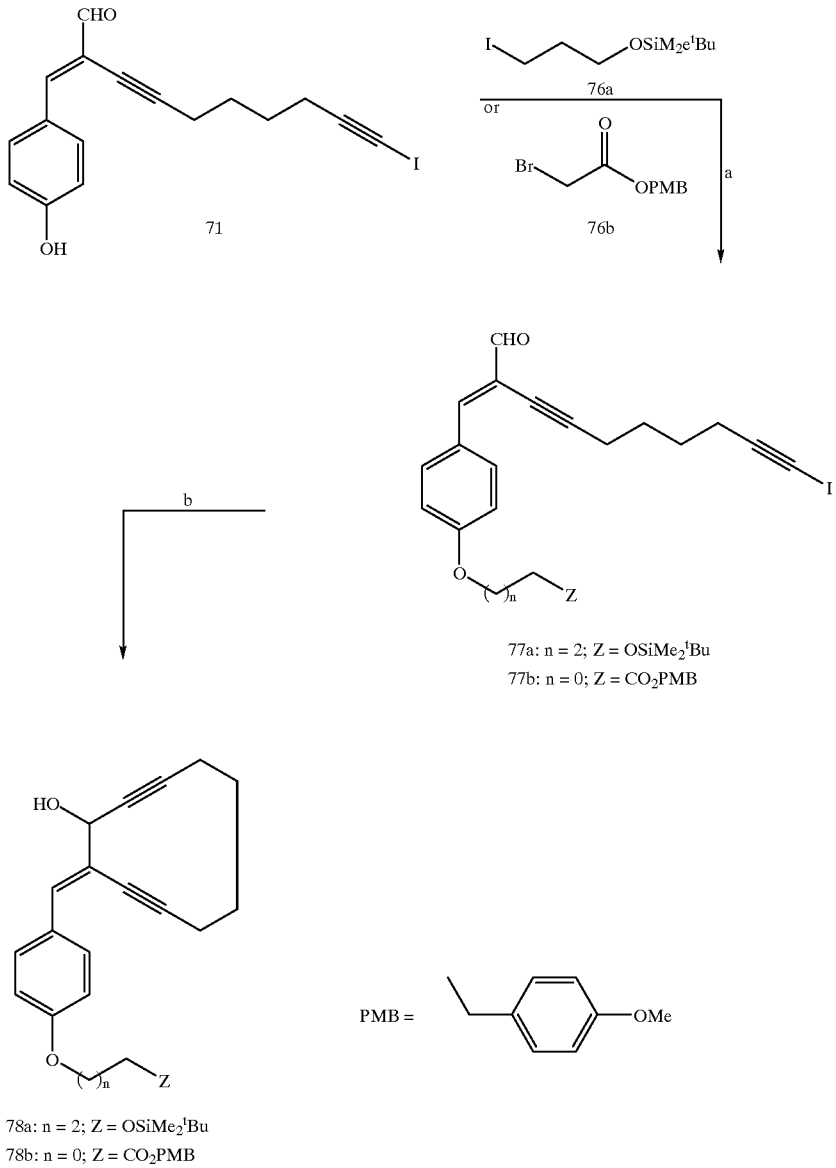

Another method for preparing a compound of this invention having the formula IA in which X represents an acyloxy group is illustrated below in Scheme XIX. Compound 78b was reacted in step a with excess acetic anhydride in the presence of DMAP in dichloromethane at 20° C. for 2 hours to form Compound 79 in 60 percent yield. Alternatively, with methoxyethanoic acid in the presence of DCC and DMAP in dichloromethane at 20° C. for 10 hours to form Compound 84 in 68 percent yield. Compounds 83 and 84 were treated in step d with catalytic PPTS in methanol at 20° C. for 20 hours to form Compounds 85 and 86 in 70 to 75 percent yield.

Scheme XIX

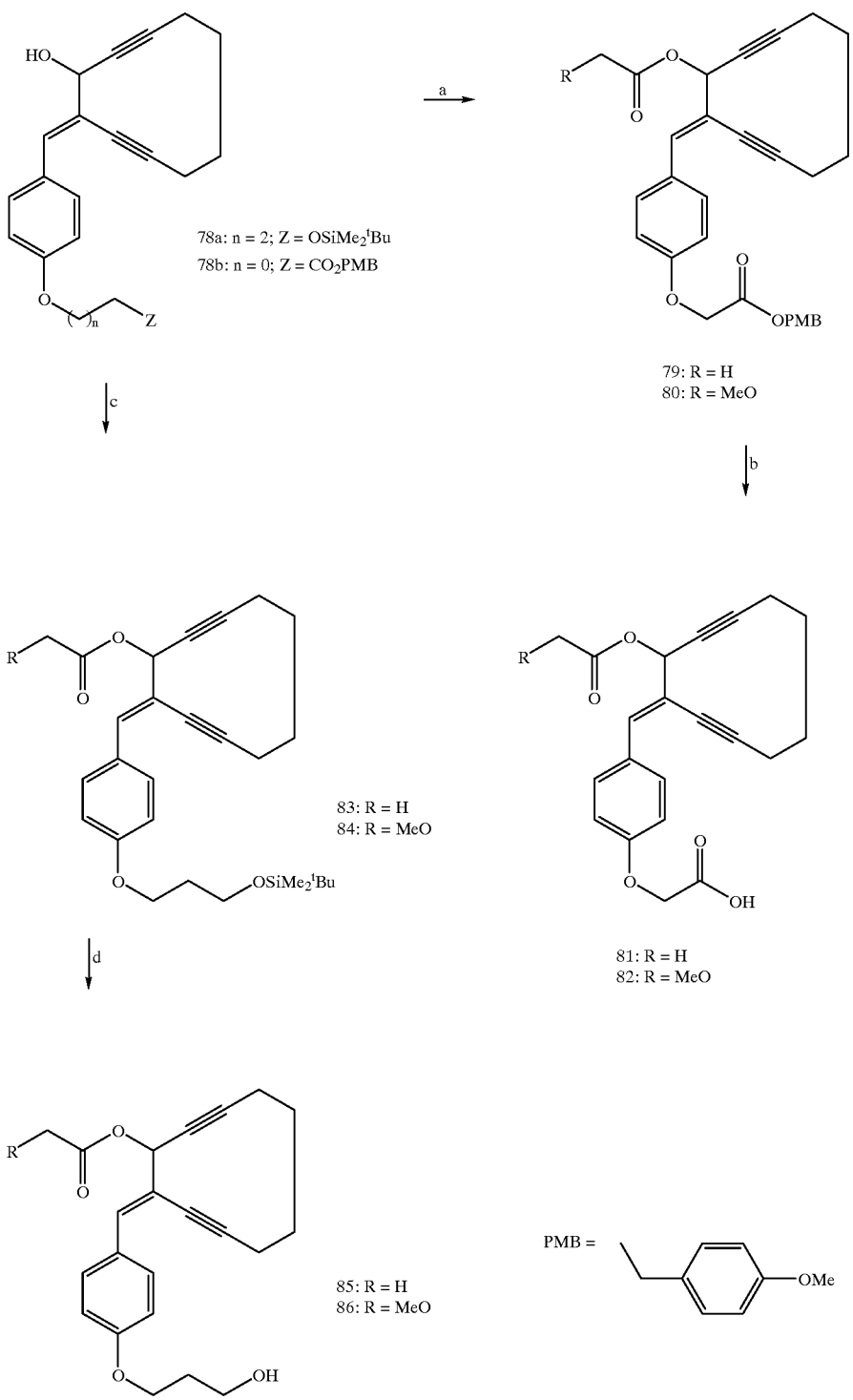

A compound of this invention having the formula IB in which X represents an acyloxy group was prepared according to Scheme XX illustrated below. Compounds 80 and 84 were treated in step a with 0.1 equivalents of Eu(fod)$_3$ in trichloromethane at 20° C. for 40 hours to form Compounds 87 and 88 in 60 to 65 percent yield. Compound 87 was irradiated in step b with UV light in aqueous THF at 0° C. for 15 minutes to form Compound 89 in 86 percent yield. On the other hand, Compound 88 was treated with a catalytic amount of PPTS in methanol at 20° C. for 20 hours to form Compound 90 in 73 percent yield.

Scheme XX

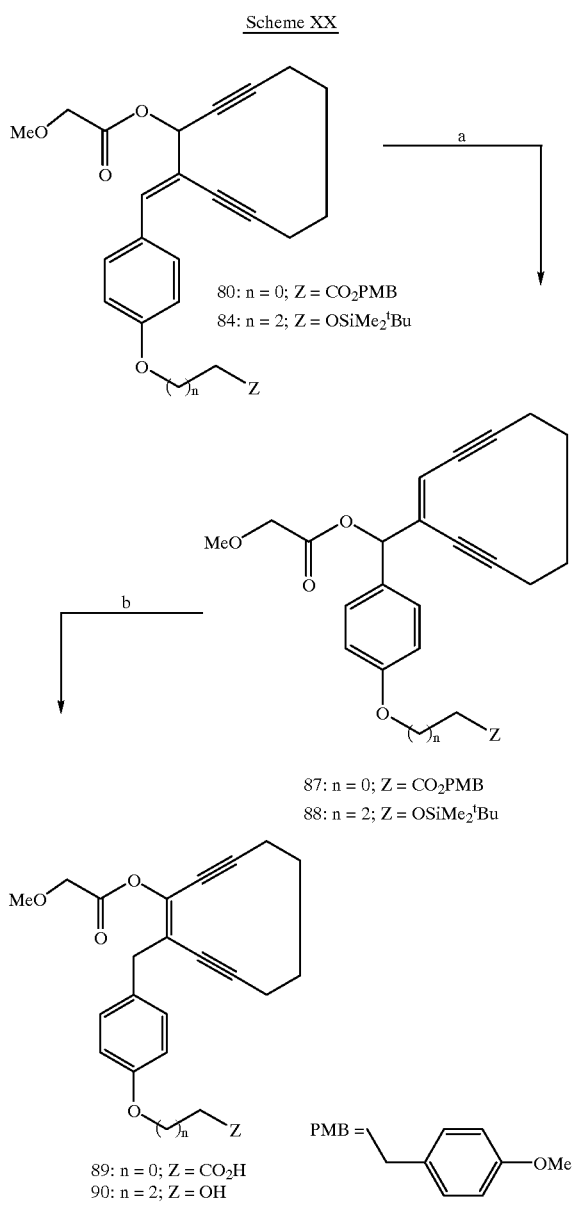

80: n = 0; Z = CO₂PMB
84: n = 2; Z = OSiMe₂ᵗBu

87: n = 0; Z = CO₂PMB
88: n = 2; Z = OSiMe₂ᵗBu

89: n = 0; Z = CO₂H
90: n = 2; Z = OH

PMB = $\text{–CH}_2\text{–C}_6\text{H}_4\text{–OMe}$

The above-mentioned Compounds 81, 82, 85, 86, 89, and 90 are suitable for preparation of drug conjugates by attachment through an ester or amide linkage. Preferably, a molecule that can recognize a specific DNA sequence, such as distamycin, is conjugated with the enediynes and enediyne prodrugs to achieve selective damage to DNA.

The invention also provides a pharmaceutical composition which comprises a carrier and, as active ingredient, a compound of the general formula A, B, IA or IB as defined above or a salt thereof. Such compositions may be prepared by bringing the active ingredient into association with the carrier.

A carrier may be any material with which the active ingredient is formulated to facilitate administration. When used for therapeutic purposes, the carrier must be pharmaceutically acceptable in the sense that it is compatible with the other ingredients of the composition and will not have any deletorius effect on the recipient of the composition. A carrier may be a solid or a liquid, including a material which is normally gaseous but which has been compressed to form a liquid, and any of the carriers normally used in formulating pharmaceutical compositions may be used. Preferably, compositions according to the invention contain 0.5 to 95% by weight of active ingredient.

The compounds of general formula I can be formulated as, for example, tablets, capsules, suppositories or solutions. These formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

Compounds of the invention are present in such pharmaceutical compositions in an amount effective to achieve the desired result as will be discussed below.

The invention also provides methods of using compounds of the general formula A, B, IA or IB or salts thereof or pharmaceutical compositions containing such compounds as DNA cleaving agents, protein-degrading or protein-modulating agents, antimicrobial and cytotoxic (antitumor) agents. Compounds of the invention thus exhibit similar types of biological activity to the known compounds calicheamicin and neocarzinostatin.

Specifically, methods for cleaving DNA and for degrading or modulating a protein are provided which comprise contacting DNA, target cells or a protein with a compound of the general formula IA or IB or a salt thereof as defined above or a pharmaceutical composition as defined above. Where the method is carried out in vitro, contact is made by admixing the DNA, target cells or protein with the active compounds or composition and maintaining them together under appropriate conditions of temperature for cell growth to occur. Where the method is carried out in vivo, contact between the active compound and the target cells or protein is made by administering the active compound, preferably in the form of a suitable pharmaceutical composition, to the subject by any of the conventional routes for administration of a pharmaceutical. Thus, contact in vivo is achieved via the blood or lymph systems.

Methods for inhibiting tumor growth, treating cancer and inhibiting microbial growth are also provided which comprise administering to a patient a therapeutically effective amount of a compound of the general formula A, B, IA or IB or a salt thereof as defined above or, preferably, a pharmaceutical composition as defined above. Again, administration may be by any of the conventional routes for administration of a pharmaceutical.

Where in vitro DNA cleavage is the desired result, a compound of the invention can be utilised in an amount sufficient to provide a concentration of about 1.0 to about 5000 µM with a DNA concentration of about 0.02 µg/ml. Where a compound is to be used as a cytotoxic (antitumor) agent, an effective amount is about 0.05 to about 50 mg compound per kilogram, preferably about 0.1 to about 15 mg per kilogram, of body weight or an amount sufficient to provide a concentration of about 0.01 to about 50 µg/ml to the bloodstream. For antimicrobial activity, concentrations of about 0.01 mg to about 50 µg/ml may be used. However, the above concentrations will of course vary according to the particular compound of the invention which is utilised as well as the target selected, that is, DNA, tumor or microbe.

Typical concentrations for in vitro cytotoxity studies also vary with the cells to be killed. However, typical $IC_{50}$ values range from $1\times10^{-7}$M to $1\times10^{-3}$M, especially $1\times10^{-6}$ to $1\times10^{-4}$M. Typical in vivo dosages are about 1 to about 100 mg/kg body weight of the recipient. Typical concentrations useful for in vitro cleavage of DNA range from about 0.1 to about 500 µM, preferably about 1 to about 200 µM.

Although a single admixture and the resultant contact is generally sufficient to maintain the required contact and obtain the desired result in vitro, multiple administrations may be required in vivo in order to counteract the breakdown and excretion pathways of the body. Typically, repeated administrations of an active ingredient may be required over a period of time such as days, weeks, months or more, depending on the target cells. Lower dosages are generally preferred when multiple doses are required.

The invention is further illustrated by the following examples.

EXAMPLE 1

(E)-2-(Phenylmethylidene)deca-3,9-diyn-1-al
(Compound 2)

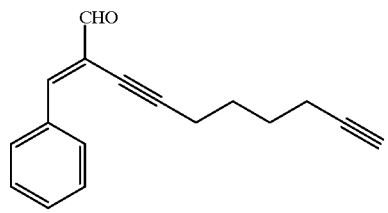

2

To a solution of $Pd(PPh_3)_4$ (0.55 g, 0.24 mmol) and α-bromocinnamaldehyde Compound 1 (2.08 g, 4.74 mmol) in degassed THF (170 mL) cooled in an ice-water bath was added a solution of 1,7-octadiyne (2.23 g, 9.48 mmol), triethylamine (15 mL), and CuI (0.36 g, 0.95 mmol) in degassed THF (30 mL) via a syringe under a nitrogen atmosphere. The reaction flask was then covered by a sheet of aluminum foil. After stirring at room temperature for 8 hours the reaction was quenched with saturated aqueous $NH_4Cl$ (50 mL) and diluted with EtOAc (100 mL). The organic layer was washed with brine, dried over anhydrous $MgSO_4$, filtered, and concentrated in vacuo. The residue was purified by flash column chromatography (silica gel, 10 percent EtOAc in hexane) to give 2.13 g (91 percent) of Compound 2: yellow oil; $R_f$=0.50 (15 percent EtOAc in hexane); IR (neat) 3294, 2944, 2230, 2116, 1692, 1598, 1450, 1324, 1180 $cm^{-1}$; $^1$H NMR (300 MHz, $CDCl_3$) δ9.56 (s, 1H), 8.11–8.07 (m, 2H), 7.48–7.43 (m, 3H), 7.43 (s, 1H), 2.60 (t, J=6.65 Hz, 2H), 2.27 (td, J=6.78, 2.64 Hz, 2H), 1.97 (t, J=2.64 Hz, 1H), 1.86–1.69 (m, 4H); $^{13}$C NMR (75 MHz, $CDCl_3$) δ192.4, 151.8, 134.9, 132.0, 131.1, 129.4, 124.1, 103.4, 84.6, 75.4, 69.4, 28.2, 28.0, 20.3, 18.7; MS (+FAB) m/z (relative intensity) 237 ($M+H^+$, 100).

EXAMPLE 2

(E)-2-(Phenylmethylidene)deca-3,9-diyn-1-ol
(Compound 3)

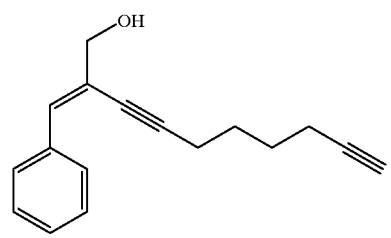

3

To a solution of Compound 2 (502 mg, 2.13 mmol) in methanol (20 mL) was added a solution of $NaBH_4$ (80.4 mg, 2.13 mmol) in aqueous NaOH (0.5 N, 5 mL) followed by stirring at room temperature for 30 minutes. The reaction was then quenched with saturated aqueous $NH_4Cl$ (50 mL) and extracted with EtOAc (50 mL×2). The combined organic layer was washed with brine, dried over anhydrous $MgSO_4$, filtered, and concentrated in vacuo. The residue was purified by flash column chromatography (silica gel, 20 percent EtOAc in hexane) to give 462.3 mg (91.4 percent) of Compound 3: yellow oil; $R_f$=0.19 (17 percent EtOAc in hexane); IR (neat) 3400 (br), 3296, 2942, 2862, 2210, 2116, 1072 $cm^{-1}$; $^1$H NMR (300 MHz, $CDCl_3$) δ7.84–7.81 (m, 2H), 7.37–7.26 (m, 3H), 6.71 (s, 1H), 4.25 (s, 2H), 2.49 (t, J=6.65 Hz, 2H), 2.24 (td, J=6.78, 2.37 Hz, 2H), 2.17 (br s, 1H), 1.98 (t, J=2.64 Hz, 1H), 1.79–1.60 (m, 4H); $^{13}$C NMR (75 MHz, $CDCl_3$) δ136.7, 133.3, 129.1, 128.8, 128.7, 122.5, 98.8, 84.7, 79.3, 69.3, 68.1, 28.2, 28.1, 20.0, 18.6; MS (+CI) m/z (relative intensity) 239 ($M+H^+$, 15), 221 (100); HRMS (+EI) calcd for $C_{17}H_{18}O$ 238.1358 ($M^+$), found 238.1316.

EXAMPLE 3

(E)-10-Iodo-2-(phenylmethylidene)deca-3,9-diyn-1-ol (Compound 4)

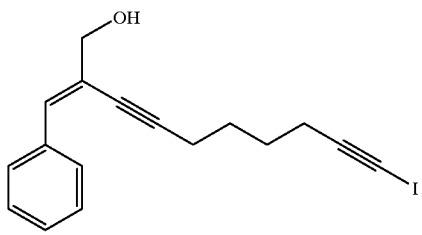

4

To a solution of iodine (1.479 g, 5.83 mmol) in toluene (80 mL) was added morpholine (1.354 g, 15.54 mmol) followed by heating at 60° C. for 30 minutes. To the resultant mixture was added a solution of Compound 3 (462.3 mg, 1.94 mmol) in toluene (10 mL) and the mixture was heated at the same temperature for 6 hours. The reaction mixture was then allowed to cool down to room temperature and purified, without aqueous work up, by flash column chromatography (silica gel, 100 percent hexane and then 17 percent EtOAc in hexane) to give 630.3 mg (89 percent) of Compound 4: yellow oil; $R_f$=0.17 (17 percent EtOAc in hexane); IR (neat) 3362 (br), 2942, 2860, 2210, 1446, 1072 cm$^{-1}$; $^1$H NMR (300 MHz, CDCl$_3$) δ7.83–7.79 (m, 2H), 7.37–7.24 (m, 3H), 6.71 (s, 1H), 4.26 (d, J=1.20 Hz, 2H), 2.51–2.39 (m, 4H), 1.95 (br s, 1H), 1.76–1.62 (m, 4H); $^{13}$C NMR (75 MHz, CDCl$_3$) δ136.7, 133.5, 129.1, 128.9, 128.8, 122.5, 98.7, 94.7, 79.4, 68.2, 28.3, 28.1, 21.0, 20.1, −5.9; MS (+CI) m/z (relative intensity) 365 (M+H$^+$, 10), 220 (100); HRMS (+EI) calcd for C$_{17}$H$_{17}$IO 364.0324 (M$^+$), found 364.0299.

EXAMPLE 4

(E)-10-Iodo-2-(phenylmethylidene)deca-3,9-diyn-1-al (Compound 5)

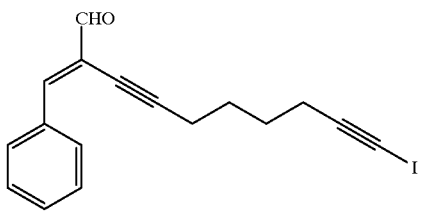

5

To a solution of Compound 4 (399.4 mg, 1.10 mmol) in dry CH$_2$Cl$_2$ (50 mL) cooled at 0° C. in an ice-water bath was added PCC (591.3 mg, 2.74 mmol) followed by stirring at room temperature for 2 hours. The reaction mixture was diluted with Et$_2$O and filtered through a short silica gel plug with rinsing by EtOAc. The filtrate was concentrated under reduced pressure and the residue was purified by flash column chromatography (silica gel, 17 percent EtOAc in hexane) to give 296.6 mg (75 percent) of Compound 5: pale yellow oil; $R_f$=0.36 (17 percent EtOAc in hexane); IR (neat) 2942, 2230, 1690, 1596, 1450, 1324, 1180 cm$^{-1}$; $^1$H NMR (300 MHz, CDCl$_3$) δ9.55 (s, 1H), 8.10–8.04 (m, 2H), 7.48–7.44 (m, 3H), 7.42 (s, 1H), 2.60 (td, J=6.66, 2.46 Hz, 2H), 2.44 (t, J=6.75, 2H), 1.83–1.66 (m, 4H); $^{13}$C NMR (75 MHz, CDCl$_3$) δ192.4, 151.9, 134.8, 132.1, 131.0, 129.4, 124.0, 103.3, 94.7, 75.4, 28.3, 28.0, 21.1, 20.3, −5.9; MS (+CI) m/z (relative intensity) 363 (M+H$^+$, 40), 207 (100); HRMS (+EI) calcd for C$_{17}$H$_{15}$IO 362.0168 (M$^+$), found 362.0107.

EXAMPLE 5

(E)-4-(Phenylmethylidene)cyclodeca-1,5-diyn-3-ol (Compound 6)

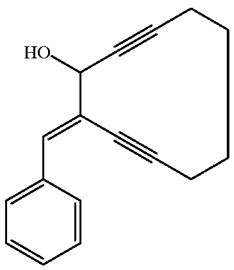

6

Method A

A suspension of anhydrous CrCl$_2$ (181.9 mg, 1.41 mmol) and NiCl$_2$ (60.7 mg, 0.47 mmol) in dry THF (120 mL) was stirred at room temperature for 3 hours. To this mixture was added a solution of Compound 5 (169.7 mg, 0.47 mmol) in dry THF (5 mL) followed by stirring at room temperature for 8 hours. The reaction was quenched with saturated aqueous NH$_4$Cl (50 mL) and the resultant mixture was concentrated under reduced pressure to a volume of about 80 mL that was then extracted with EtOAc (50 mL×3). The combined organic layer was washed with brine, dried over anhydrous MgSO$_4$, filtered, and concentrated in vacuo. The residue was purified by flash column chromatography (silica gel, 9 percent EtOAc in hexane) to give 32.4 mg (29 percent) of Compound 6.

Method B

To a suspension of Pd(PPh$_3$)$_4$ (45.7 mg, 3.96×10$^{-2}$ mmol) and CuI (15.2 mg, 7.92×10$^{-2}$ mmol) in a degassed mixed solvent containing 18 percent diethylamine in acetonitrile (20 mL) was added a solution of Compound 7 (126.1 mg, 0.40 mmol) in degassed acetonitrile (2 mL) followed by stirring at 80–85° C. (oil bath) for 1.5 hours. The reaction mixture was then concentrated in vacuo. The residue was diluted with EtOAc (20 mL) and filtered through a short plug of silica gel with rinsing by EtOAc. The filtrate was concentrated under reduced pressure and the residue was purified by flash column chromatography (silica gel, 20 percent EtOAc in hexane) to give 39.8 mg (42.5 percent) of Compound 6: pale yellow oil, $R_f$=0.36 (20 percent EtOAc in hexane); IR (neat) 3388 (br), 2928, 2210, 1448, 1022 cm$^{-1}$; $^1$H NMR (300 MHz, CDCl$_3$) δ7.90–7.86 (m, 2H), 7.38–7.24 (m, 3H), 6.72 (s, 1H), 4.96 (d, J=7.17 Hz, 1H), 2.52–2.46 (m, 2H), 2.28–2.24 (m, 2H), 2.17 (d, J=6.39 Hz, 1H, exchangeable with D$_2$O), 1.89–1.65 (m, 4H); $^{13}$C NMR (75 MHz, CDCl$_3$) δ136.5, 133.5, 129.2, 129.1, 128.9, 125.3, 104.7, 92.3, 82.6, 81.2, 69.1, 28.4, 28.2, 22.6, 21.3; MS (+CI) m/z (relative intensity) 237 (M+H$^+$, 14), 219 (100); HRMS (+FAB) calcd for C$_{17}$H$_{17}$O 237.1279 (M+H$^+$), found 237.1360.

EXAMPLE 6

(Z)-2-Bromo-1-phenylundeca-1-en-4,10-diyn-3-ol (Compound 7)

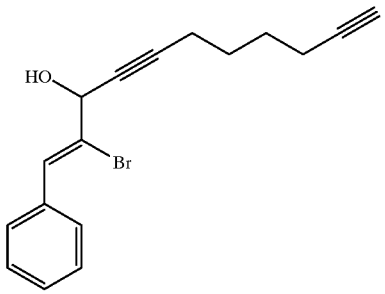

To a solution of 1,7-octadiyne (254.4 mg, 2.4 mmol) in dry THF (50 mL) cooled at −78° C. was added "BuLi (1.6 M in hexanes, 1.5 mL, 2.0 mmol) followed by stirring at the same temperature for 10 minutes. To the previously prepared lithium acetylide solution was added a solution of α-bromocinnamaldehyde Compound 1 (422.0 mg, 2.0 mmol) in dry THF (5 mL) and the resultant mixture was stirred at −78° C. for 15 minutes. The reaction was then quenched with saturated aqueous $NH_4Cl$ (20 mL) and extracted with EtOAc (50 mL×2). The combined organic layer was washed with brine, dried over anhydrous $MgSO_4$, filtered, and concentrated under reduced pressure. The residue was purified by flash column chromatography (silica gel, 14 percent EtOAc in hexane) to give 613.1 mg (97 percent) of Compound 7: pale yellow oil; $R_f$=0.33 (14 percent EtOAc in hexane); IR (neat) 3397 (br), 3294, 2944, 2864, 2232, 2116, 1492, 1430, 1064 $cm^{-1}$; $^1H$ NMR (300 MHz, $CDCl_3$) δ7.65–7.61 (m, 2H), 7.40–7.29 (m, 3H), 7.24 (s, 1H), 5.07 (br s, 1H), 2.68 (d, J=6.18 Hz, 1H, exchangeable with $D_2O$), 2.34–2.27 (m, 2H), 2.26–2.19 (m, 2H), 1.96 (t, J=2.67 Hz, 1H), 1.74–1.62 (m, 4H); $^{13}C$ NMR (75 MHz, $CDCl_3$) δ135.4, 129.8, 129.1, 128.9, 126.8, 88.3, 84.8, 79.0, 69.4, 69.3, 61.2, 28.1, 27.9, 19.0, 18.6; MS (+CI) m/z (relative intensity) 318 ($M^+$, $^{81}Br$, 4), 316 ($M^+$, $^{79}Br$, 4), 220 (100).

EXAMPLE 7

(Z)-2-Bromo-3-methoxy-1-phenylundeca-1-en-4,10-diyne (Compound 8)

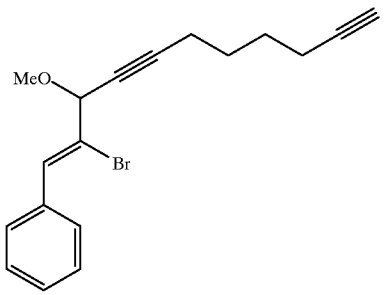

To a solution of Compound 7 (303.0 mg, 0.96 mmol) and KOH (214.1 mg, 3.82 mmol) in DMSO (20 mL) was added MeI (271.3 mg, 1.91 mmol) followed by stirring at room temperature for 5 hours. The reaction was then quenched with saturated aqueous $NH_4Cl$ (20 mL) and extracted with EtOAc (50 mL×2). The combined organic layer was washed with brine, dried over anhydrous $MgSO_4$, filtered, and concentrated under reduced pressure. The residue was purified by flash column chromatography (silica gel, 20 percent EtOAc in hexane) to give 214.3 mg (68 percent) of Compound 8: pale yellow oil; $R_f$=0.56 (20 percent EtOAc in hexane); IR (neat) 3296, 2940, 2232, 2116, 1446, 1078 $cm^{-1}$; $^1H$ NMR (300 MHz, $CDCl_3$) δ7.68–7.65 (m, 2H), 7.38–7.25 (m, 3H), 7.29 (s, 1H), 4.76 (s, 1H), 3.42 (s, 3H), 2.36–2.31 (m, 2H), 2.26–2.21 (m, 2H), 1.95 (t, J=2.67 Hz, 1H), 1.74–1.65 (m, 4H); $^{13}C$ NMR (75 MHz, $CDCl_3$) δ135.4, 131.4, 129.8, 129.1, 128.8, 123.9, 89.2, 84.6, 77.5, 76.8, 69.3, 56.0, 28.1, 27.9, 19.0, 18.5; MS (+CI) m/z (relative intensity) 333 ($M+H^+$, $^{81}Br$, 10), 331 ($M+H^+$, $^{79}Br$, 12), 251 (100); HRMS (+EI) calcd for $C_{18}H_{19}BrO$ 330.0619 ($M^+$), found 330.0606.

EXAMPLE 8

(E)-3-Methoxy-4-(phenylmethylidene)cyclodeca-1,5-diyne (Compound 9)

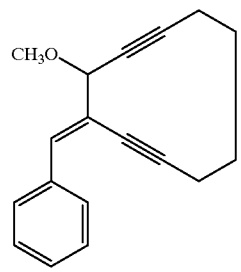

A suspension of Compound 8 (102.3 mg, 0.31 mmol), $Pd(PPh_3)_4$ (71.4 mg, 6.18×$10^{-2}$ mmol) and CuI (11.8 mg, 6.18×$10^{-2}$ mmol) in degassed diethylamine (30 mL) under a nitrogen atmosphere was heated at 50–60° C. for one and a half hours. The reaction mixture was concentrated under reduced pressure. To the residue was added saturated aqueous $NH_4Cl$ (20 mL) and extracted with EtOAc (20 mL×3). The combined organic layer was washed with brine, dried over anhydrous $MgSO_4$, filtrated, and concentrated in vacuo. The residue was purified by flash column chromatography (silica gel, 6 percent EtOAc in hexane) to give 9.5 mg (12 percent) of Compound 8: pale yellow oil; $R_f$=0.33 (6 percent EtOAc in hexane); IR (neat) 2932, 2234, 2118, 1448, 1076 $cm^{-1}$; $^1H$ NMR (300 MHz, $CDCl_3$) δ7.90 (d, J=7.38 Hz, 2H), 7.37–7.26 (m, 3H), 6.67 (s, 1H), 4.72 (s, 1H), 3.43 (s, 3H), 2.57–2.20 (m, 4H), 1.95–1.67 (m, 4H); $^{13}C$ NMR (75 MHz, $CDCl_3$) δ136.5, 134.5, 129.3, 129.0, 128.9, 122.3, 104.5, 93.0, 81.7, 80.3, 76.8, 55.9, 28.4, 28.2, 22.7, 21.3; MS (+CI) m/z (relative intensity) 251 ($M+H^+$, 50), 219 (100); HRMS (+EI) calcd for $C_{18}H_{18}O$ ($M^+$) 250.1358, found 250.1339.

EXAMPLE 9

Methyl (E)- and (Z)-2-[(4'-Methoxyphenyl)methylidene]deca-3,9-diynoate (Compound 16a)

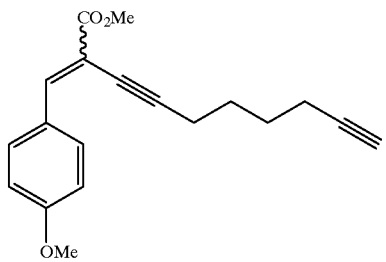

16a

To a suspension of Pd(PPh$_3$)$_4$ (92.1 mg, 0.08 mmol) and CuI (30.4 mg, 0.16 mmol) in degassed acetonitrile (2.3 mL) maintained at 0° C. in an ice-water bath was added a solution of Compound 15a (E:Z=75:25, 216.0 mg, 0.80 mmol), 1,7-octadiyne (0.26 mL, 2.00 mmol), and 1-ethylpiperidine (0.70 mL) in degassed acetonitrile (4 mL) via a syringe. The reaction flask was covered against light by a sheet of aluminum foil, and the mixture was stirred at room temperature for 5 hours. The reaction was quenched with saturated aqueous NH$_4$Cl (10 mL) and extracted with EtOAc (20 mL×2). The organic layer was washed with brine (10 mL), dried over anhydrous MgSO$_4$, filtered, and concentrated under reduced pressure. The residue was purified by flash column chromatography (silica gel, 5 percent EtOAc in hexane) to give 162.0 mg (69 percent) of Compound 16a as an inseparable mixture (E:Z=25:75): pale yellow oil; R$_f$=0.26 (10 percent EtOAc in hexane); IR (neat) 3296, 2950, 2220, 2216, 1728, 1716, 1606, 1512, 1258, 1178 cm$^{-1}$; signals assigned for (E)-16a (minor): $^1$H NMR (300 MHz, CDCl$_3$) δ8.50–7.98 (AA'BB', 2H), 7.80 (s, 1H), 6.97–6.88 (AA'BB', 2H), 3.84 (s, 3H), 3.83 (s, 3H), 2.56 (t, J=6.48 Hz, 2H), 1.98–1.95 (m, 2H), 1.82–1.72 (m, 2H); $^{13}$C NMR (75 MHz, CDCl$_3$) δ166.9, 161.3, 144.3, 132.1, 129.5, 127.3, 113.8, 110.4, 98.7, 78.9, 68.6, 55.2, 52.3, 52.5, 27.5, 27.3, 19.5, 17.9; signals assigned for (Z)-16a (major): $^1$H NMR (300 MHz, CDCl$_3$) δ7.37–7.27 (AA'BB', 2H), 7.06 (s, 1H), 6.88–6.79 (AA'BB', 2H), 3.80 (s, 3H), 3.76 (s, 3H), 2.41 (t, J=6.41 Hz, 2H), 2.30–2.19 (m, 2H), 1.73–1.62 (m, 2H); $^{13}$C NMR (75 MHz, CDCl$_3$) δ166.7, 160.2, 143.0, 130.6, 127.2, 114.0, 113.7, 91.5, 84.1, 78.9, 68.5, 55.2, 52.3, 27.5, 27.4, 19.0, 17.9; MS (+CI) m/z (relative intensity) 297 (M+H$^+$, 82), 237 (100); HRMS (+EI) calcd for C$_{19}$H$_{20}$O$_3$ (M$^+$) 296.1412, found 296.1388.

EXAMPLE 10

Methyl (E)- and (Z)-2-(1'-Naphthylmethylidene)deca-3,9-diynoate (Compound 16b)

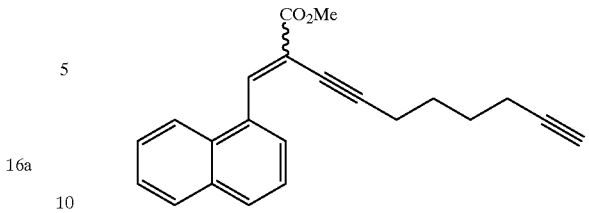

16b

To a suspension of Pd(PPh3)$_4$ (874 mg, 0.76 mmol) and CuI (288 mg, 1.51 mmol) in degassed acetonitrile (25 mL) cooled in an ice-water bath was added a solution of Compound 15b (as a 50:50 mixture, 2.20 g, 7.56 mmol), 1,7-octadiyne (2.51 mL, 18.9 mmol), and 1-ethylpiperidine (6 mL) in degassed acetonitrile (30 mL) via a syringe under a nitrogen atmosphere. The reaction flask was covered against light by a sheet of aluminum foil, and the mixture was stirred at room temperature for 4 hours. The reaction was quenched with saturated aqueous NH$_4$Cl (60 mL) and extracted with EtOAc (100 mL×2). The combined organic layer was washed with brine (30 mL), dried over anhydrous MgSO$_4$, filtered, and concentrated under reduced pressure. The residue was purified by flash column chromatography (silica gel, 5 percent EtOAc in hexane) to give 1.57 g (66 percent) of Compound 16b as an inseparable mixture (E:Z=48:52): yellow oil; R$_f$=0.23 (5 percent EtOAc in hexane); IR (neat) 3294, 2948, 2222, 2116, 1732, 1594, 1240 cm$^{-1}$; $^1$H NMR (300 MHz, CDCl$_3$, recorded as a mixture) δ8.63 (s, 1H, (E)-16b), 8.38 (d, J=7.32 Hz, 1H), 8.10 (br d, J=7.59 Hz, 1H), 7.96–7.79 (m, 5H), 7.75 (s, 1H, (Z)-16b), 7.50–7.48 (s, 5H), 7.45–7.36 (m, 2H), 3.92 (s, 3H, (E)-16b), 3.56 (s, 3H, (Z)-16b), 2.54–2.43 (m, 4H), 2.28 (td, J=6.68, 2.61 Hz, 2H, (Z)-16b), 2.19 (td, J=6.61, 2.64 Hz, 2H, (E)-16b), 1.98 (t, J=2.61 Hz, 1H, (Z)-16b), 1.95 (t, J=2.64 Hz, 1H, (E)-16b), 1.78–1.62 (m, 8H); $^{13}$C NMR (75 MHz, CDCl$_3$, recorded as a mixture) δ166.4, 166.0, 142.3, 124.2, 133.5, 133.3, 132.8, 131.7, 131.1, 131.0, 130.4, 129.0, 128.7, 128.5, 127.3, 126.7, 126.4, 126.1, 125.1, 125.0, 124.4, 123.6, 119.0, 115.6, 98.0, 92.7, 84.1, 84.0, 78.2, 76.3, 68.6, 68.5, 52.8, 52.2, 27.6, 27.4 (×2), 27.2, 19.3, 19.1, 18.0, 17.9; MS (+CI) m/z (relative intensity) 317 (M+H$^+$, 94), 257 (100); HRMS (+EI) calcd for C$_{22}$H$_{20}$O$_2$ (M$^+$) 316.1463, found 316.1438.

EXAMPLE 11

Methyl (E)- and (Z)-2-(2'-Naphthylmethylidene)deca-3,9-diynoate (Compound 16c)

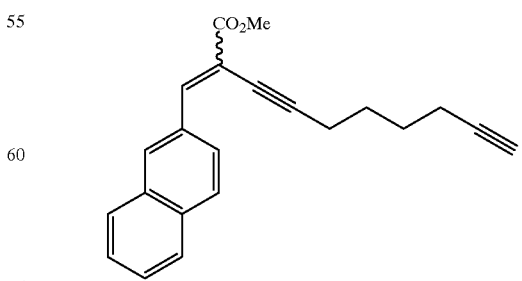

16c

53

Compound (E)-16c. To a suspension of Pd(PPh$_3$)$_4$ (81.6 mg, 0.07 mmol) and CuI (26.9 mg, 0.14 mmol) in degassed acetonitrile (2.4 mL) maintained at 0° C. in an ice-water bath was added a solution of Compound (E)-15c (205 mg, 0.71 mmol), 1,7-octadiyne (0.23 mL, 1.73 mmol), and 1-ethylpiperidine (0.6 mL) in degassed acetonitrile (3.0 mL) via a syringe. The reaction flask was covered against light by a sheet of aluminum foil, and the mixture was stirred at room temperature for 5 hours. The reaction was quenched with saturated aqueous NH$_4$Cl (10 mL) and extracted with EtOAc (15 mL×2). The organic layer was washed with brine (5 mL), dried over anhydrous MgSO$_4$, filtered, and concentrated under reduced pressure. The residue was purified by flash column chromatography (silica gel, 5 percent EtOAc in hexane) to give 150 mg (67 percent) of Compound (E)-16c: pale yellow solid; R$_f$=0.21 (5 percent EtOAc in hexane); IR (KBr) 3302, 2942, 2218, 2116, 1724, 1588, 1264, 1246 cm$^{-1}$; $^1$H NMR (300 MHz, CDCl$_3$) δ8.46 (s, 1H), 8.18 (dd, J=8.66, 1.67 Hz, 1H), 8.01 (s, 1H), 7.90–7.79 (m, 3H), 7.57–7.45 (m, 2H), 3.89 (s, 3H), 2.61 (t, J=6.66 Hz, 2H), 2.28 (td, J=6.74, 2.64 Hz, 2H), 1.98 (t, J=2.64 Hz, 1H), 1.91–1.70 (m, 4H); $^{13}$C NMR (75 MHz, CDCl$_3$) δ166.6, 144.7, 134.1, 132.9, 132.1, 131.0, 128.8, 127.9, 127.6, 127.4, 126.5, 126.4, 113.3, 99.5, 84.0, 76.9, 68.6, 52.7, 27.6, 19.6, 18.0; MS (+CI) m/z (relative intensity) 317 (M+H$^+$, 100); HRMS (+EI) calcd for C$_{22}$H$_{20}$O$_2$ (M$^+$) 316.1463, found 316.1456.

Compound (Z)-16c. To a suspension of Pd(PPh$_3$)$_4$ (61.7 mg, 0.05 mmol) and CuI (20.3 mg, 0.11 mmol) in degassed acetonitrile (2.0 mL) maintained at 0° C. in an ice-water bath was added a solution of Compound (Z)-15c (155 mg, 0.53 mmol), 1,7-octadiyne (0.18 mL, 1.36 mmol), and 1-ethylpiperidine (0.5 mL) in degassed acetonitrile (2.5 mL) via a syringe. The reaction flask was covered against light by a sheet of aluminum foil, and the mixture was stirred at room temperature for 1.5 hours. The reaction was quenched with saturated aqueous NH$_4$Cl (10 mL) and extracted with EtOAc (15 mL×2). The organic layer was washed with brine (5 mL), dried over anhydrous MgSO$_4$, filtered, and concentrated under reduced pressure. The residue was purified by flash column chromatography (silica gel, 5 percent EtOAc in hexane) to give 123 mg (73 percent) of Compound (Z)-16c: pale yellow oil; R$_f$=0.22 (5 percent EtOAc in hexane); IR (neat) 3294, 2948, 2220, 2116, 1732, 1600, 1434, 1236, 1202, 1160 cm$^{-1}$; $^1$H NMR (300 MHz, CDCl$_3$)δ7.83–7.73 (m, 4H), 7.52–7.44 (m, 2H), 7.41 (dd, J=8.57, 1.67 Hz, 1H), 7.29 (s, 1H), 3.77 (s, 3H), 2.46 (t, J=6.48 Hz, 2H), 2.27 (td, J=6.54, 2.67 Hz, 2H), 1.99 (t, J=2.67 Hz, 1H), 1.80–1.64 (m, 4H); $^{13}$C NMR (75 MHz, CDCl$_3$) δ166.6, 142.7, 133.2, 133.0, 132.2, 128.7, 128.3, 127.8, 127.6, 126.8, 126.4, 125.6, 116.7, 92.8, 84.0, 78.6, 68.6, 52.4, 27.5, 27.4, 19.1, 17.9; MS (+CI) m/z (relative intensity) 317 (M+H$^+$, 100); HRMS (+EI) calcd for C$_{22}$H$_{20}$O$_2$(M$^+$) 316.1463, found 316.1454.

54

EXAMPLE 12

(E)- and (Z)-2-[(4'-Methoxyphenyl)methylidene] deca-3,9-diyn-1-ol (Compound 17a)

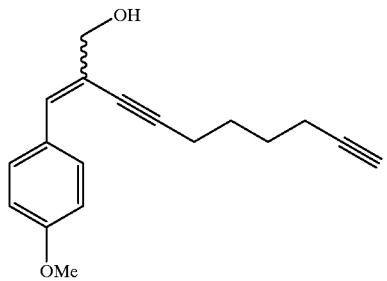

17a

To a solution of Compound 16a (E:Z=25:75, 1.90 g, 6.42 mmol) in dry toluene (80 mL) cooled in a dry ice-acetone bath (−78° C.) was added DIBAL (1 M in CH$_2$Cl$_2$, 16.0 mL, 16.0 mmol) followed by stirring at the same temperature for 1 hour. The reaction was quenched by MeOH (15 mL) at −78° C. and stirred for 30 minutes. Five percent aqueous HCl (100 mL) was added, and the mixture was stirred at room temperature for another 40 minutes. The mixture was extracted with EtOAc (100 mL×2), the organic layer was washed with brine (50 mL), dried over anhydrous MgSO$_4$, filtered, and concentrated under reduced pressure. The residue was purified by flash column chromatography (silica gel, 20 percent EtOAc in hexane) to give 1.62 g (94 percent) of Compound 17a as (E)- and (Z)-isomers (E:Z=26:74).

Compound (E)-16a (minor): colorless oil; R$_f$=0.18 (20 percent EtOAc in hexane); IR (neat) 3384 (br), 3294, 2936, 2208, 2116, 1606, 1512, 1302, 1254, 1178, 1034 cm$^{-1}$; $^1$H NMR (300 MHz, CDCl$_3$) δ7.82–7.76 (AA'BB', 2H), 6.91–6.84 (AA'BB ', 2H), 6.63 (s, 1H), 4.22 (s, 2H), 3.81 (s, 3H), 2.49 (t, J=6.51 Hz, 2H), 2.25 (td, J=6.63, 2.62 Hz, 2H), 2.10–1.96 (br s, 1H), 1.98 (t, J=2.62 Hz, 1H), 1.81–1.63 (m, 4H); $^{13}$C NMR (75 MHz, CDCl$_3$) δ159.3, 132.5, 129.8, 128.9, 119.4, 113.5, 97.6, 84.0, 79.0, 68.6, 67.7, 55.2, 27.6, 27.5, 19.4, 17.9; MS (+CI) m/z (relative intensity) 268 (M$^+$, 42), 251 (100); HRMS (+EI) calcd for C$_{18}$H$_{20}$O$_2$ (M$^+$) 268.1463, found 268.1467.

Compound (Z)-16a (major): pale yellow oil; R$_f$=0.23 (20 percent EtOAc in hexane); IR (neat) 3424 (br), 3294, 2940, 2214, 2116, 1606, 1510, 1252, 1178, 1032 cm$^{-1}$; $^1$H NMR (300 MHz, CDCl$_3$) δ7.21–7.15 (AA'BB', 2H), 6.90–6.85 (m, 2H), 6.85 (s, 1H), 4.33 (s, 2H), 3.81 (s, 3H), 2.42 (t, J=6.44 Hz, 2H), 2.25 (td, J=6.55, 2.64 Hz, 2H), 2.10–1.92 (br s, 1H), 1.97 (t, J=2.64 Hz, 1H), 1.77–1.60 (m, 4H); $^{13}$C NMR (75 MHz, CDCl$_3$) δ159.2, 136.3, 130.3, 128.4, 122.6, 113.8, 91.4, 84.1, 81.1, 68.6, 61.2, 55.2, 27.7, 27.6, 19.0, 18.0; MS (+CI) m/z (relative intensity) 269 (M+H$^+$, 26), 251 (100); HRMS (+EI) calcd for C$_{18}$H$_{20}$O$_2$ (M$^+$) 268.1463, found 268.1455.

EXAMPLE 13

(E)- and (Z)-2-(1'-Naphthylmethylidene)deca-3,9-diyn-1-ol (Compound 17b)

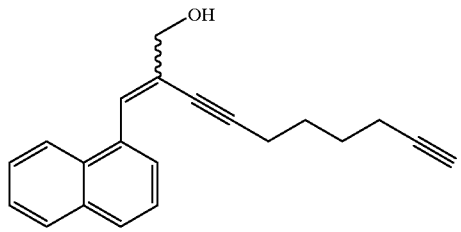

17b

To a solution of Compound 16b (a 48:52 mixture, 1.55 g, 4.91 mmol) in dry toluene (65 mL) cooled in a dry ice-acetone bath (−78° C.) was added DIBAL (1M in $CH_2Cl_2$, 12.3 mL, 12.3 mmol) followed by stirring at the same temperature for 1 hour. The reaction was quenched by MeOH (10 mL) at −78° C. and stirred for 30 minutes. Five percent aqueous HCl (80 mL) was added, and the mixture was stirred at room temperature for another 35 minutes. The mixture was extracted with EtOAc (75 mL×2), the organic layer was washed with brine (50 mL), dried over anhydrous $MgSO_4$, filtered, and concentrated under reduced pressure. The residue was purified by flash column chromatography (silica gel, 15 percent EtOAc in hexane) to give 1.32 g of Compound 17b (93 percent) as a 45:55 mixture. Analytic samples of (E)-17b and (Z)-17b were obtained by repeat column chromatographic separation.

Compound (E)-17b: pale yellow oil; $R_f$=0.28 (20 percent EtOAc in hexane); IR (neat) 3405 (br), 3296, 2942, 2212, 2116, 1430, 1078, 1020 $cm^{-1}$; $^1H$ NMR (300 MHz, $CDCl_3$) δ8.11 (d, J=7.20 Hz, 1H), 8.08–8.04 (m, 1H), 7.87–7.83 (m, 1H), 7.80 (d, J=8.22 Hz, 1H), 7.53–7.46 (m, 3H), 7.42 (s, 1H), 4.39 (s, 2H), 2.35 (t, J=6.39 Hz, 2H), 2.15 (td, J=6.75, 2.16 Hz, 2H), 2.18–2.00 (br s, 1H), 1.96 (t, J=2.64 Hz, 1H), 1.65–1.49 (m, 4H); $^{13}C$ NMR (75 MHz, $CDCl_3$) δ133.5, 132.9, 131.5, 130.2, 128.5, 128.2, 126.3, 126.0, 125.7, 125.1, 124.6, 123.8, 96.6, 84.0, 78.3, 68.5, 67.1, 27.3, 27.2, 19.1, 17.8; MS (+CI) m/z (relative intensity) 289 (M+H$^+$, 13), 271 (100); HRMS (+EI) calcd for $C_{21}H_{20}O$ (M$^+$) 288.1514, found 288.1513.

Compound (Z)-17b: pale yellow oil; $R_f$=0.35 (20 percent EtOAc in hexane); IR (neat) 3418 (br), 3296, 2942, 2216, 2116, 1428, 1394, 1246, 1016 $cm^{-1}$; $^1H$ NMR (300 MHz, $CDCl_3$) δ7.99–7.94 (m, 1H), 7.88–7.84 (m, 1H), 7.81 (d, J=8.28 Hz, 1H), 7.54–7.47 (m, 3H), 7.44 (d, J=8.10 Hz, 1H), 7.40 (s, 1H), 7.31 (d, J=7.08 Hz, 1H), 4.23 (d, J=3.78 Hz, 2H), 2.49 (d, J=6.57 Hz, 2H), 2.28 (td, J=6.75, 2.64 Hz, 2H), 1.99 (t, J=2.64 Hz, 1H), 1.95–1.84 (br s, 1H), 1.82–1.68 (m, 4H); $^{13}C$ NMR (75 MHz, $CDCl_3$) δ134.5, 133.4, 132.7, 131.5, 128.4, 128.4, 126.8, 126.3, 126.2, 126.0, 125.2, 124.8, 92.1, 84.1, 80.5, 68.6, 61.4, 27.7, 27.6, 19.1, 18.0; MS (+CI) m/z (relative intensity) 289 (M+H$^+$, 23), 271 (100); HRMS (+EI) calcd for $C_{21}H_{20}O$ (M$^+$) 288.1514, found 288.1501.

EXAMPLE 14

(E)- and (Z)-2-(2'-Naphthylmethylidene)deca-3,9-diyn-1-ol (Compound 17c)

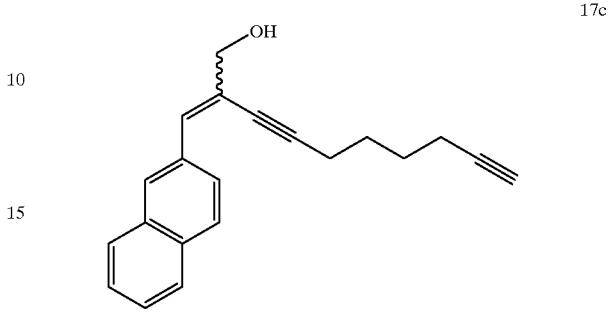

17c

Compound (Z)-17c. To a solution of Compound (Z)-17c (115.0 mg, 0.36 mmol) in dry toluene (5 mL) cooled in a dry ice-acetone bath (−78° C.) was added DIBAL (1 M in $CH_2Cl_2$, 0.91 mL, 0.91 mmol) followed by stirring at the same temperature for 1 hour. The reaction was quenched by MeOH (1 mL) at −78° C. and stirred for 30 minutes. Five percent aqueous HCl (8 mL) was added, and the mixture was stirred at room temperature for another 40 minutes. The mixture was extracted with EtOAc (10 mL×2), the organic layer was washed with brine (10 mL), dried over anhydrous $MgSO_4$, filtered, and concentrated under reduced pressure. The residue was purified by flash column chromatography (silica gel, 15 percent EtOAc in hexane) to give 97.0 mg (93 percent) of Compound (Z)-17c: colorless oil; $R_f$=0.23 (15 percent EtOAc in hexane); IR (neat) 3400 (br), 3296, 2944, 2214, 2116, 1018 $cm^{-1}$; $^1H$ NMR (300 MHz, $CDCl_3$) δ7.86–7.77 (m, 3H), 7.69 (s, 1H), 7.52–7.44 (m, 2H), 7.37 (dd, J=8.46, 0.96 Hz, 1H), 7.06 (s, 1H), 4.44 (s, 2H), 2.46 (t, J=6.44 Hz, 2H), 2.28 (td, J=6.46, 2.54 Hz, 2H), 2.13–1.97(br s, 1H), 1.99 (t, J=2.54 Hz, 1H), 1.82–1.64 (m, 4H); $^{13}C$ NMR (75 MHz, $CDCl_3$) δ136.6, 133.2, 133.1, 132.6, 128.1, 128.0, 127.9, 127.6, 126.7, 126.3, 124.8, 92.2, 84.1, 80.1, 68.6, 61.2, 27.6, 27.5, 19.1, 18.0; MS (+CI) m/z (relative intensity) 289 (M+H$^+$, 85), 271 (100); HRMS (+EI) calcd for $C_{21}H_{20}O$ (M$^+$) 288.1514, found 288.1510.

Compound (E)-17c. Prepared from Compound (E)-16c in 92 percent yield after purification by flash column chromatography (silica gel, 15 percent EtOAc in hexane). Colorless oil; $R_f$=0.15 (15 percent EtOAc in hexane); IR (neat) 3370 (br), 3298, 2944, 2210, 2116, 1078 $cm^{-1}$; $^1H$ NMR (300 MHz, $CDCl_3$) δ8.24 (s, 1H), 8.08 (dd, J=8.64, 1.59 Hz, 1H), 7.86–7.77 (m, 3H), 7.50–7.42 (m, 2H), 6.87 (s, 1H), 4.31 (d, J=5.55 Hz, 2H), 2.54 (t, J=6.65 Hz, 2H), 2.26 (td, J=6.67, 2.60 Hz, 2H), 2.05 (t, J=6.32 Hz, 1H), 1.99 (t, J=2.60 Hz, 1H), 1.85–1.66 (m, 4H); $^{13}C$ NMR (75 MHz, $CDCl_3$) δ133.6, 133.2, 133.1, 132.8, 128.2, 127.9, 127.6, 127.5, 126.1, 126.0, 122.2, 98.3, 84.0, 78.8, 68.7, 67.6, 27.6, 27.5, 19.5, 18.0; MS (+CI) m/z (relative intensity) 289 (M+H$^+$, 15), 271 (100); HRMS (+EI) calcd for $C_{21}H_{20}O$ (M$^+$) 288.1514, found 288.1515.

EXAMPLE 15

(E)- and (Z)-10-Iodo-2-[(4'-methoxyphenyl)methylidene]deca-3,9-diyn-1-ol (Compound 18a)

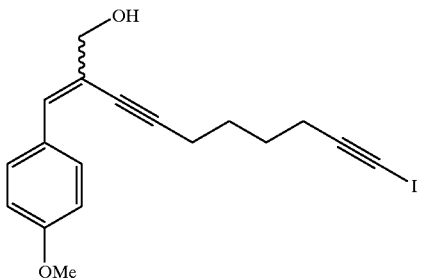

Compound (Z)-18a. To a solution of iodine (2.98 g, 11.70 mmol) in dry toluene (120 mL) was added morpholine (2.73 mL, 31.30 mmol) followed by stirring at room temperature for 15 minutes. To the resultant mixture was added Compound (Z)-17a (1.05 g, 3.92 mmol) in dry toluene (30 mL) followed by stirring at 45–50° C. for 24 hours. The reaction mixture was allowed to cool down to room temperature, and purified, without aqueous workup, by flash column chromatography directly (silica gel, 100 percent hexane and then 20 percent EtOAc in hexane) to give 1.17 g (76 percent) of Compound (Z)-18a: pale yellow oil; $R_f$=0.19 (20 percent EtOAc in hexane); IR (neat) 3418 (br), 2936, 2214, 1606, 1510, 1252, 1178, 1032 cm$^{-1}$; $^1$H NMR (300 MHz, CDCl$_3$) δ7.21–7.17 (AA'BB', 2H), 6.92–6.83 (m, 3H), 4.33 (d, J=5.70 Hz, 2H), 3.81 (s, 3H), 2.50–2.37 (m, 4H), 2.01–1.98 (br m, 1H), 1.75–1.62 (m, 4H); $^{13}$C NMR (75 MHz, CDCl$_3$) δ159.2, 136.4, 130.3, 128.4, 122.6, 113.8, 94.1, 91.3, 81.1, 61.2, 55.3, 27.7, 27.6, 20.4, 19.0, −6.8; MS (+CI) m/z (relative intensity) 395 (M+H$^+$, 25), 377 (100); HRMS (+EI) calcd for C$_{18}$H$_{19}$IO$_2$ (M$^+$) 394.0430, found 394.0448.

Compound (E)-18a. Prepared similarly from Compound (E)-17a in 90% yield after purification by flash column chromatography (silica gel, 100 percent hexane and then 20 percent EtOAc in hexane): pale yellow oil; $R_f$=0.36 (30 percent EtOAc in hexane); IR (neat) 3382 (br), 2934, 2208, 1606, 1510, 1252, 1178, 1034 cm$^{-1}$; $^1$H NMR (300 MHz, CDCl$_3$) δ7.83–7.75 (AA'BB', 2H), 6.91–6.83 (AA'BB', 2H), 6.64 (s, 1H), 4.23 (s, 2H), 3.83 (s, 3H), 2.49 (d, J=6.32 Hz, 2H), 2.43 (d, J=6.30 Hz, 2H), 1.95–1.81 (br s, 1H), 1.80–1.60 (m, 4H); $^{13}$C NMR (75 MHz, CDCl$_3$) δ159.4, 132.7, 129.8, 128.9, 119.3, 113.6, 97.5, 94.1, 79.0, 67.8, 55.3, 27.6, 27.5, 20.4, 19.4, −6.7; MS (+CI) m/z (relative intensity) 394 (M$^+$, 13), 377 (100); HRMS (+EI) calcd for C$_{18}$H$_{19}$IO$_2$ (M$^+$) 394.0430, found 394.0512.

EXAMPLE 16

(E)- and (Z)-10-Iodo-2-(1'-naphthylmethylidene)deca-3,9-diyn-1-ol (Compound 18b)

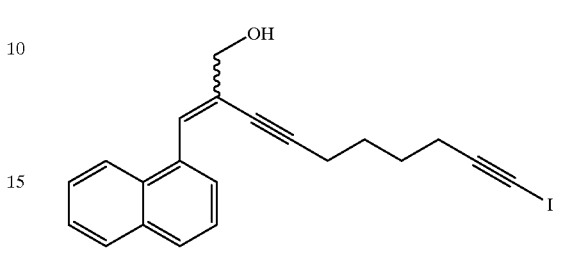

Compound (E)-18b. To a solution of iodine (1.56 g, 6.15 mmol) in dry toluene (64 mL) was added morpholine (1.43 mL, 16.4 mmol) followed by stirring at room temperature for 15 minutes. To the resultant mixture was added Compound (E)-17b (591 mg, 2.05 mmol) in dry toluene (16 mL) followed by stirring at 45–50° C. for 24 hours. The reaction mixture was allowed to cool down to room temperature, and purified, without aqueous workup, by flash column chromatography (silica gel, 100 percent hexane and then 20 percent EtOAc in hexane) to give 776 mg (91 percent) of Compound (E)-18b: yellow oil; $R_f$=0.26 (20 percent EtOAc in hexane); IR (neat) 3364 (br), 2928, 2212, 1426, 1328, 1078, 1020 cm$^{-1}$; $^1$H NMR (300 MHz, CDCl$_3$) δ8.08 (d, J=7.20 Hz, 1H), 8.06–8.02 (m, 1H), 7.87–7.84 (m, 1H), 7.81 (d, J=8.19 Hz, 1H), 7.53–7.46 (m, 3H), 7.41 (s, 1H), 4.39 (s, 2H), 2.34 (t, J=6.39 Hz, 2H), 2.31 (t, J=6.54 Hz, 2H), 2.04–1.93 (br s, 1H), 1.67–1.45 (m, 4H); $^{13}$C NMR (75 MHz, CDCl$_3$) δ133.5, 132.9, 131.5, 130.3, 128.5, 128.3, 126.4, 126.0, 125.7, 125.2, 124.6, 123.9, 96.5, 94.1, 78.3, 67.2, 27.4, 27.3, 20.3, 19.1, −6.9; MS (+CI) m/z (relative intensity) 415 (M+H$^+$, 25), 397 (100); HRMS (+EI) calcd for C$_{21}$H$_{19}$IO (M$^+$) 414.0481, found 414.0478.

Compound (Z)-18b. Prepared similarly as described for Compound (E)-18b in 84 percent yield; yellow oil; $R_f$=0.30 (20 percent EtOAc in hexane); IR (neat) 3406 (br), 2940, 2216, 1428, 1246, 1016 cm$^{-1}$; $^1$H NMR (300 MHz, CDCl$_3$) δ7.99–7.93 (m, 1H), 7.88–7.83 (m, 1H), 7.81 (d, J=8.25 Hz, 1H), 7.55–7.46 (m, 2H), 7.44 (d, J=8.07 Hz, 1H), 7.40 (s, 1H), 7.32 (d, J=7.02 Hz, 1H), 4.23 (s, 2H), 2.56–2.41 (m, 4H), 1.98–1.88 (br s, 1H), 1.82–1.62 (m, 4H); $^{13}$C NMR (75 MHz, CDCl$_3$) δ134.5, 133.4, 132.7, 131.5, 128.4, 126.8, 126.3, 126.1, 126.0, 125.2, 124.7, 94.1, 92.0, 80.5, 61.4, 27.7, 27.6, 20.4, 19.1, −6.7; MS (+CI) m/z (relative intensity) 415 (M+H$^+$, 17), 271 (100); HRMS (+EI) calcd for C$_{21}$H$_{19}$IO (M$^+$) 414.0481, found 414.0466.

EXAMPLE 17

(E)- and (Z)-10-Iodo-2-(2'-naphthylmethylidene)deca-3,9-diyn-1-ol (Compound 18c)

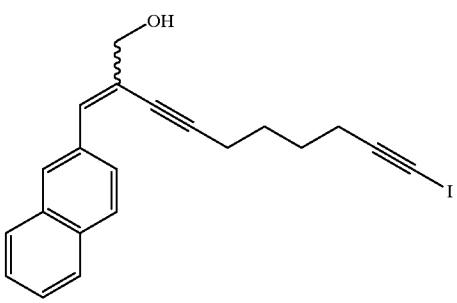

Compound (Z)-18c. To a solution of iodine (187.0 mg, 0.74 mmol) in dry toluene (8 mL) was added morpholine (1.19 mL, 13.7 mmol) followed by stirring at room temperature for 15 minutes. To the resultant mixture was added Compound (Z)-17c (70.6 mg, 0.25 mmol) in dry toluene (3 mL) followed by stirring at 45–50° C. for 24 hours. The reaction mixture was allowed to cool down to room temperature, and purified, without aqueous workup, by flash column chromatography directly (silica gel, 100 percent hexane and then 20 percent EtOAc in hexane) to give 88.4 mg (87 percent) of Compound (Z)-18c: pale yellow solid; $R_f$=0.31 (20 percent EtOAc in hexane); IR (KBr) 3406 (br), 2940, 2212, 1014 cm$^{-1}$; $^1$H NMR (300 MHz, CDCl$_3$) δ7.87–7.78 (m, 3H), 7.70 (s, 1H), 7.52–7.44 (m, 2H), 7.37 (d, J=8.55 Hz, 1H), 7.06 (s, 1H), 4.44 (s, 2H), 2.51–2.40 (m, 4H), 2.04–1.94 (br s, 1H), 1.79–1.65 (m, 4H); $^{13}$C NMR (75 MHz, CDCl$_3$) δ136.6, 133.2, 133.1, 132.6, 128.2, 128.1, 127.9, 127.6, 126.7, 126.3, 124.8, 94.1, 92.2, 80.9, 61.2, 27.7, 27.6, 20.4, 19.1, −6.7; MS (+CI) m/z (relative intensity) 415 (M+H$^+$, 50), 287 (100); HRMS (+EI) calcd for C$_{21}$H$_{19}$IO (M$^+$) 414.0481, found 414.0463.

Compound (E)-18c. Prepared from Compound (E)-17c in 92 percent yield after purification by flash column chromatography (silica gel, 100 percent hexane then 20 percent EtOAc in hexane). Pale yellow oil; $R_f$=0.20 (20 percent EtOAc in hexane); IR (neat) 3354 (br), 2942, 2210, 1076 cm$^{-1}$; $^1$H NMR (300 MHz, CDCl$_3$) δ8.22 (s, 1H), 8.05 (dd, J=8.63, 1.58 Hz, 1H), 7.86–7.77 (m, 3H), 7.52–7.43 (m, 2H), 6.88 (s, 1H), 4.31 (s, 2H), 2.53 (t, J=6.54 Hz, 2H), 2.43 (t, J=6.60 Hz, 2H), 2.06–1.93 (br s, 1H), 1.82–1.63 (m, 4H); $^{13}$C NMR (75 MHz, CDCl$_3$) δ133.6, 133.2, 133.1, 132.9, 128.2, 127.9, 127.6, 127.6, 126.2, 126.1, 122.2, 98.2, 94.0, 78.9, 67.6, 27.6, 27.5, 20.4, 19.5, −6.6; MS (+CI) m/z (relative intensity) 415 (M+H$^+$, 9), 207 (100); HRMS (+EI) calcd for C$_{21}$H$_{19}$IO (M$^+$) 414.0481, found 414.0470.

EXAMPLE 18

(E)-10-Iodo-2-[(4'-methoxyphenyl)methylidene]deca-3,9-diynal (Compound 19a)

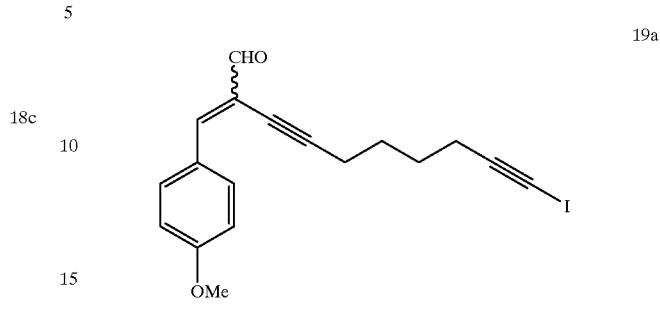

Method A

To a suspension of PCC (759 mg, 3.52 mmol) in dry CH$_2$Cl$_2$ (40 mL) was added Compound (Z)-18a (556 mg, 1.41 mmol) in CH$_2$Cl$_2$ (40 mL) followed by stirring at room temperature for 2.5 hours. The reaction mixture was diluted with EtOAc (80 mL), filtered through a short silica gel pad with rinsing by EtOAc. The filtrate was evaporated under reduced pressure and the residue was purified by flash column chromatography (silica gel, 15 percent EtOAc in hexane) to give 365 mg (66 percent) of Compound (E)-19a.

Method B

To a suspension of PCC (93.5 mg, 0.43 mmol) in dry CH$_2$Cl$_2$ (6 mL) was added Compound (E)-18a (68.5 mg, 0.17 mmol) in CH$_2$Cl$_2$ (6 mL) followed by stirring at room temperature for 2 hours. The reaction mixture was diluted with EtOAc (10 mL), filtered through a short silica gel pad with rinsing by EtOAc. The filtrate was evaporated under reduced pressure and the residue was purified by flash column chromatography (silica gel, 15 percent EtOAc in hexane) to give 54.9 mg (80 percent) of Compound (E)-19a: yellow oil; $R_f$=0.33 (20 percent EtOAc in hexane); IR (neat) 2934, 2234, 1682, 1600, 1324, 1258, 1172, 1028 cm$^{-1}$; $^1$H NMR (300 MHz, CDCl$_3$) δ9.51 (s, 1H), 8.10–8.03 (AA'BB', 2H), 7.36 (s, 1H), 7.00–6.93 (AA'BB', 2H), 3.88 (s, 3H), 2.60 (t, J=6.50 Hz, 2H), 2.45 (t, J=6.44 Hz, 2H), 1.83–1.67 (m, 4H); $^{13}$C NMR (75 MHz, CDCl$_3$) δ191.9, 162.2, 151.3, 132.5, 127.1, 121.0, 114.2, 101.8, 94.1, 74.9, 55.5, 27.6, 27.4, 20.4, 19.6, −6.7; MS (+CI) m/z (relative intensity) 393 (M+H$^+$, 100); HRMS (+EI) calcd for C$_{18}$H$_{17}$IO$_2$ (M$^+$) 392.0273, found 392.0226.

EXAMPLE 19

(E)- and (Z)-10-Iodo-2-(1'-naphthylmethylidene)deca-3,9-diynal (Compound 19b)

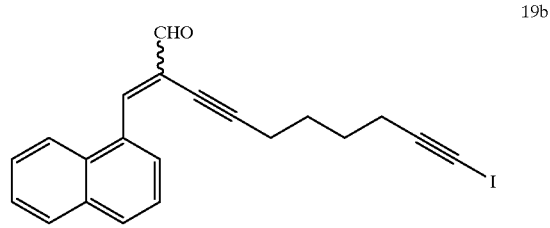

Method A

To a suspension of PCC (90.9 mg, 0.42 mmol) in dry CH$_2$Cl$_2$ was added Compound (E)-18b (70.0 mg, 0.17 mmol) in CH$_2$Cl$_2$ followed by stirring at room temperature for 2 hours. The reaction mixture was diluted with EtOAc, filtered through a short silica gel pad with rinsing by EtOAc. The filtrate was concentrated under reduced pressure and the residue was purified by flash column chromatography (silica gel, 5 percent EtOAc in hexane) to give 61.3 mg (88 percent) of Compound (E)-19b.

Method B

To a suspension of PCC (1.87 g, 4.52 mmol) in dry CH$_2$Cl$_2$ (90 mL) was added Compound (Z)-18b (1.87 g, 4.52 mmol) in CH$_2$Cl$_2$ (15 mL) followed by stirring at room temperature for 2.5 hours. The reaction mixture was diluted with EtOAc (50 mL), filtered through short a silica gel pad with rinsing by EtOAc. The filtrate was concentrated under reduced pressure and the residue was purified by flash column chromatography (silica gel, 5 percent EtOAc in hexane) to give 653 mg (35%) of Compound (Z)-19b and 997 mg (54 percent) of Compound (E)-19b. Alternatively, Compound (Z)-19b was completed isomerized into Compound (E)-19b under the PCC oxidation after prolonged time.

Compound (E)-19b: yellow oil; R$_f$=0.44 (20 percent EtOAc in hexane); IR (neat) 2944, 2222, 1688, 1594, 1570, 1340, 1250, 1186 cm$^{-1}$; $^1$H NMR (300 MHz CDCl$_3$) δ9.72 (s, 1H), 8.61 (d, J=7.29 Hz, 1H), 8.26 (s, 1H), 8.13 (d, J=8.16 Hz, 1H), 7.97 (d, J=8.22 Hz, 1H), 7.93–7.89 (m, 1H), 7.63–7.53 (m, 3H), 2.52 (t, J=6.57 Hz, H), 2.38 (t, J=6.54 Hz, 2H), 1.60–1.75 (m, 4H); $^{13}$C NMR (75 MHz, CDCl$_3$) δ191.5, 147.7, 133.5, 131.6, 131.5, 130.3, 129.0, 127.8, 127.1, 126.2, 125.1, 122.8, 110.6, 94.0, 74.6, 27.5, 27.2, 20.3, 19.4, −6.6; MS (+CI) m/z (relative intensity) 413 (M+H$^+$, 94), 286 (100); HRMS (+EI) calcd for C$_{21}$H$_{17}$IO (M$^+$) 412.0324, found 412.0322.

Compound (Z)-19b: yellow solid; R$_f$=0.50 (20 percent EtOAc in hexane); IR (KBr) 2948, 2226, 1676, 1506, 1312 cm$^1$; $^1$H NMR (300 MHz, CDCl$_3$) δ9.68 (s, 1H), 8.49 (s, 1H), 8.02–7.86 (m, 3H), 7.67–7.53 (m, 3H), 7.48 (t, J=7.62 Hz, 1H), 7.37 (d, J=6.93 Hz, 2H), 2.50 (t, J=6.48 Hz, 2H), 2.44 (t, J=6.42 Hz, 2H), 1.85–1.67 (m, 4H); $^{13}$C NMR (75 MHz, CDCl$_3$) δ189.7, 149.9, 133.4, 131.2, 130.7, 130.2, 129.8, 128.7, 127.6, 127.2, 126.7, 125.0, 124.8, 95.9, 94.1, 75.9, 27.6, 27.5, 20.4, 19.2, −6.8; MS (+CI) m/z (relative intensity) 413 (M+H$^+$, 78), 287 (100); HRMS (+EI) calcd for C$_{21}$H$_{17}$IO (M$^+$) 412.0324, found 412.02989.

EXAMPLE 20

(E)-10-Iodo-2-(2'-naphthylmethylidene)deca-3,9-diynal (Compound 19c)

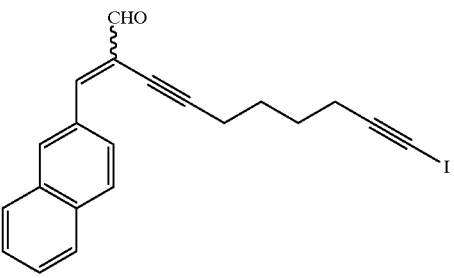

19c

Method A

To a suspension of PCC (125.0 mg, 0.58 mmol) in dry CH$_2$Cl$_2$ (6 mL) was added Compound (E)-18c (96.1 mg, 0.23 mmol) in CH$_2$Cl$_2$ (6 mL) followed by stirring at room temperature for 2 hours. The reaction mixture was diluted with EtOAc (10 mL), filtered through a short silica gel pad with rinsing by EtOAc. The filtrate was evaporated under reduced pressure and the residue was purified by flash column chromatography (silica gel, 10 percent EtOAc in hexane) to give 76.4 mg (80 percent) of Compound (E)-19c.

Method B

To a suspension of PCC (362.0 mg, 1.68 mmol) in dry CH$_2$Cl$_2$ (20 mL) was added Compound (Z)-18c (279.0 mg, 0.67 mmol) in CH$_2$Cl$_2$ (20 mL) followed by stirring at room temperature for 2.5 hours. The reaction mixture was diluted with EtOAc (30 mL), filtered through a short silica gel pad with rinsing by EtOAc. The filtrate was evaporated under reduced pressure and the residue was purified by flash column chromatography (silica gel, 10 percent EtOAc in hexane) to give 207.0 mg (74 percent) of Compound (E)-19c: yellow oil; R$_f$=0.42 (20 percent EtOAc in hexane); IR (neat) 2944, 2222, 1694, 1602, 1188, cm$^{-1}$; $^1$H NMR (300 MHz, CDCl$_3$) δ9.58 (s, 1H), 8.46 (s, 1H), 8.18 (dd, J=8.67, 1.62 Hz, 1H), 7.95–7.80 (m, 3H), 7.61–7.48 (m, 3H), 2.63 (t, J=6.65 Hz, 2H), 2.45 (t, J=6.65 Hz, 2H), 1.93–1.68 (m, 4H); $^{13}$C NMR (75 MHz, CDCl$_3$) δ191.6, 151.2, 134.5, 132.8, 131.7, 131.5, 128.9, 128.2, 127.9, 127.7, 126.7, 126.2, 123.3, 102.6, 93.9, 74.8, 27.6, 27.3, 20.3, 19.6, −6.4; MS (+CI) m/z (relative intensity) 413 (M+H$^+$, 97), 287 (100); HRMS (+EI) calcd for C$_{21}$H$_{17}$IO (M$^+$) 412.0324, found 412.0317.

EXAMPLE 21

(E)-4-[(4'-Methoxyphenyl)methylidene]cyclodeca-1,5-diyn-3-ol

(Compound 20a)

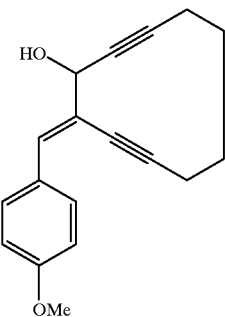

A suspension of $CrCl_2$ (175.4 mg, 1.43 mmol) and $NiCl_2$ (61.5 mg, 0.48 mmol) in dry THF (150 mL) was stirred at room temperature for 3 hours. To this mixture was added a solution of Compound 19a (186.5 mg, 0.48 mmol) in dry THF (10 mL) followed by stirring at room temperature for 8 hours. The reaction was quenched with saturated aqueous $NH_4Cl$ (50 mL) and the resultant mixture was concentrated under reduced pressure to a volume of about 100 mL that was then extracted with EtOAc (50 mL×3). The combined organic layer was washed with brine, dried over anhydrous $MgSO_4$, filtered, and concentrated in vacuo. The residue was purified by flash column chromatography (silica gel, 20 percent EtOAc in hexane) to give 31.7 mg (25 percent) of Compound 20a: pale yellow oil; $R_f$=0.30 (20 percent EtOAc in hexane); IR (neat) 3422 (br), 2934, 2212, 1604, 1510, 1252, 1178, 1030 $cm^{-1}$; $^1H$ NMR (300 MHz, $CDCl_3$) δ7.86 (d, J=8.82, Hz, 2H), 6.88 (d, J=8.82 Hz, 2H), 6.65 (s, 1H), 4.93 (d, J=6.36 Hz, 1H), 3.82 (s, 3H), 2.57–2.41 (m, 2H), 2.35–2.20 (m, 3H), 1.88–1.65 (m, 4H); $^{13}C$ NMR (75 MHz, $CDCl_3$) δ160.3, 133.3, 130.7, 129.4, 122.9, 114.4, 104.0, 92.2, 82.8, 81.3, 69.1, 55.9, 28.4, 28.2, 22.6, 21.3; MS (+CI) m/z (relative intensity) 267 (M+H$^+$, 57), 249 (100); HRMS (+EI) calcd for $C_{18}H_{18}O_2$ (M$^+$) 266.1307, found 266.1290.

EXAMPLE 22

(E)-4-(1'-Naphthylmethylidene)cyclodeca-1,5-diyn-3-ol (Compound 20b)

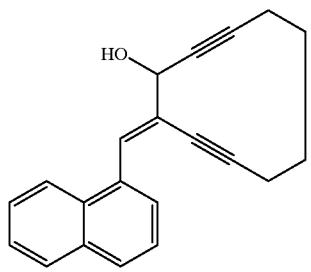

A suspension of $CrCl_2$ (240.3 mg, 1.96 mmol) and $NiCl_2$ (84.5 mg, 0.65 mmol) in dry THF (150 mL) was stirred at room temperature for 3 hours. To this mixture was added a solution of Compound 19b (268.5 mg, 0.65 mmol) in dry THF (10 mL) followed by stirring at room temperature for 8 hours. The reaction was quenched with saturated aqueous $NH_4Cl$ (50 mL) and the resultant mixture was concentrated under reduced pressure to a volume of about 80 mL that was then extracted with EtOAc (50 mL×3). The combined organic layer was washed with brine, dried over anhydrous $MgSO_4$, filtered, and concentrated in vacuo. The residue was purified by flash column chromatography (silica gel, 20 percent EtOAc in hexane) to give 46.6 mg (25 percent) of Compound 20b: pale yellow oil; $R_f$=0.30 (20 percent EtOAc in hexane); IR (neat) 3364 (br), 2930, 2229, 1428, 1024 $cm^{-1}$; $^1H$ NMR (300 MHz, $CDCl_3$) 8.29 (d, J=6.99 Hz, 1H), 8.11–8.03 (m, 1H), 7.88–7.77 (m, 2H), 7.57–7.43 (m, 4H), 5.14 (s, 1H), 2.62–2.20 (m, 5H), 2.00–1.65 (m, 4H); $^{13}C$ NMR (75 MHz, $CDCl_3$) δ134.2, 133.3, 132.2, 130.1, 129.3, 129.2, 127.8, 126.9, 126.8, 126.4, 126.0, 124.2, 103.2, 92.2, 82.7, 81.0, 68.7, 28.3, 28.2, 22.5, 21.3; MS (+CI) m/z (relative intensity) 287 (M+H$^+$, 40), 269 (100); HRMS (+EI) calcd for $C_{21}H_{18}O$ (M$^+$) 286.1358, found 286.1342.

EXAMPLE 23

(E)-4-(2'-Naphthylmethylidene)cyclodeca-1,5-diyn-3-ol (Compound 20c)

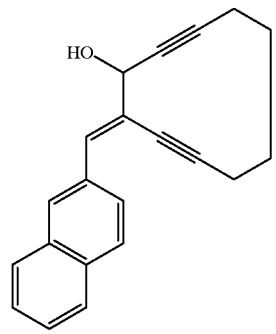

A suspension of $CrCl_2$ (232.5 mg, 1.89 mmol) and $NiCl_2$ (81.7 mg, 0.63 mmol) in dry THF (150 mL) was stirred at room temperature for 3 hours. To this mixture was added a solution of Compound 19c (259.8 mg, 0.63 mmol) in dry THF (10 mL) followed by stirring at room temperature for 8 hours. The reaction was quenched with saturated aqueous $NH_4Cl$ (50 mL) and the resultant mixture was concentrated under reduced pressure to a volume of about 100 mL that was then extracted with EtOAc (50 mL×3). The combined organic layer was washed with brine, dried over anhydrous $MgSO_4$, filtered, and concentrated in vacuo. The residue was purified by flash column chromatography (silica gel, 25 percent EtOAc in hexane) to give 31.3 mg (17 percent) of Compound 20c: pale yellow oil; $R_f$=0.34 (25 percent EtOAc in hexane); IR (neat) 3358 (br), 2934, 2200, 1428, 1022 $cm^{-1}$; $^1H$ NMR (300 MHz, $CDCl_3$) δ8.24–8.17 (m, 2H), 7.88–7.78 (m, 3H), 7.52–7.44 (m, 2H), 6.88 (s, 1H), 5.02 (d, J=6.57 Hz, 1H), 2.62–2.48 (m, 2H), 2.32–2.25 (m, 2H), 1.97–1.75 (m, 5H); $^{13}$C NMR (75 MHz, CDCl$_3$) δ134.2, 133.9, 133.6, 129.1, 129.0, 128.5, 128.3, 127.0, 126.8, 126.4, 125.6, 104.8, 92.3, 82.6, 81.3, 69.1, 28.4, 28.2, 22.7, 21.3; MS (+CI) m/z (relative intensity) 287 (M+H$^+$, 72), 269 (100); HRMS (+EI) calcd for C$_{21}$H$_{18}$O (M$^+$) 286.1358, found 286.1353.

EXAMPLE 24

Methyl (E)- and (Z)-2-[2'-((((tert-butyldimethyl)silyloxy)methyl)phenyl)methylidene]-3,9-diyn-decanoate (Compound 24)

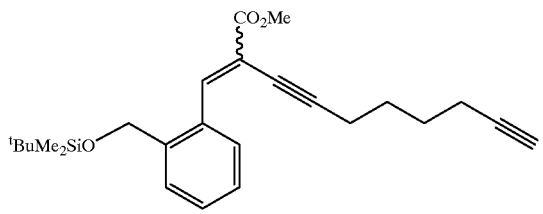

To a suspension of Pd(PPh$_3$)$_4$ (573.0 mg, 0.50 mmol) and CuI (378.0 mg, 1.98 mmol) in degassed THF (250 mL) cooled in an ice-water bath (0° C.) was added a solution of Compound 23 (E:Z=60:40, 3.82 g, 9.91 mmol), 1,7-octadiyne (1.58 g, 14.87 mmol), and triethylamine (2.76 mL, 19.83 mmol) in degassed THF (50 mL) via a syringe. The reaction flask was covered against light by a sheet of aluminum foil, and the mixture was stirred at room temperature for 20 hours. The reaction was quenched with saturated aqueous NH$_4$Cl (200 mL) and extracted with EtOAc (200 mL×2). The organic layer was washed with brine, dried over anhydrous MgSO$_4$, filtered, and concentrated under reduced pressure. The residue was purified by flash column chromatography (silica gel, 5 percent EtOAc in hexane) to give 1.62 g (40 percent) of Compound 24 as a 65:35 mixture of E:Z isomers: yellow oil; R$_f$=0.62 (20 percent EtOAc in hexane); IR (neat) 3308, 2952, 1724, 1254, 1076 cm$^{-1}$; signals assigned for Compound (E)-24 (major): $^1$H NMR (400 MHz, CDCl$_3$) δ7.46–7.30 (m, 5H), 4.70 (s, 2H), 3.62 (s, 3H), 2.46–2.44 (m, 2H), 2.26–2.21 (m, 2H), 1.96 (t, J=2.40 Hz, 1H), 1.71–1.57 (m, 4H), 0.94 (s, 9H), 0.11 (s, 6H); signals assigned for Compound (Z)-24 (minor): $^{-1}$H NMR (400 MHz, CDCl$_3$) δ8.23 (d, J=7.82 Hz, 1H), 8.11 (s, 1H), 7.46–7.30 (m, 1H), 7.19 (t, J=7.60 Hz, 1H), 7.13 (d, J=7.2 Hz, 1H), 4.78 (s, 2H), 3.86 (s, 2H), 2.46–2.44 (m, 2H), 2.26–2.21 (m, 2H), 1.96 (t, J=2.40 Hz, 1H), 1.71–1.57 (m, 4H), 0.92 (s, 9H), 0.10 (s, 6H); $^{13}$C NMR (100 MHz, CDCl$_3$, recorded as a mixture) δ166.2, 165.8, 142.3, 142.1, 140.4, 138.6, 133.3, 132.7, 129.7, 128.8, 128.5, 127.9, 127.1, 126.7, 126.6, 117.8, 114.7, 92.3, 84.0, 78.1, 77.2, 68.6, 63.4, 63.2, 52.7, 52.2, 27.6, 27.5, 27.5, 27.3, 26.0, 25.9, 19.5, 19.2, 18.5, 18.2, 18.1, 18.0, −5.2; MS (+CI) m/z (relative intensity) 411 (M+H$^+$, 14), 169 (100); HRMS (+EI) calcd for C$_{25}$H$_{34}$O$_3$Si (M$^+$) 410.2277, found 410.2216.

EXAMPLE 25

(E)- and (Z)-2-[2'-((((tert-butyldimethyl)silyloxy)methyl)phenyl)methylidene]deca-3,9-diyn-1-ol (Compound 25)

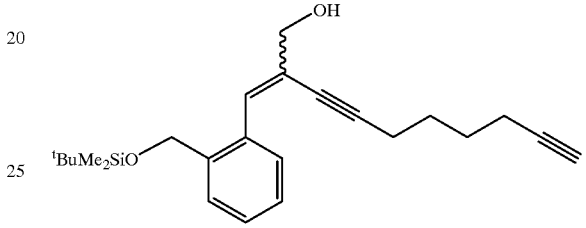

To a solution of Compound 24 (E:Z=65:35, 1.62 g, 3.96 mmol) in dry CH$_2$Cl$_2$ (50 mL) cooled in a dry ice-acetone bath (−78° C.) was added DIBAL (1 M in CH$_2$Cl$_2$, 7.91 mL, 7.91 mmol) followed by stirring at −78° C. for 1 hour. The reaction was then quenched with MeOH (25 mL) at −78° C. followed by 10 percent HCl (20 mL) at room temperature. The resultant mixture was stirred at room temperature for 30 minutes and extracted with CH$_2$Cl$_2$ (30×3 mL). The combined organic layer was washed with brine, dried over anhydrous MgSO$_4$, filtered, and concentrated under reduced pressure. The residue was purified by flash column chromatography (silica gel, 20 percent EtOAc in hexane) to give 1.16 g (77 percent) of Compound 25 as a 65:35 mixture of E:Z isomers: colorless oil; R$_f$=0.34 (20 percent EtOAc in hexane); IR (neat) 3410 (br), 3308, 2930, 1256, 1076 cm$^{-1}$; signals assigned for Compound (E)-25 (major): $^1$H NMR (400 MHz, CDCl$_3$) δ7.46 (d, J=7.60 Hz, 1H), 7.32–7.22 (m, 2H), 7.11 (d, J=7.20 Hz, 1H), 6.94 (s, 1H), 4.67 (s, 2H), 4.16 (s, 2H), 2.44 (t, J=6.80 Hz, 2H), 2.27 (td, J=6.80, 2.4 Hz, 2H), 1.98–1.95 (m, 1H), 1.75–1.59 (m, 4H), 0.94 (s, 9H), 0.12 (s, 6H); signals assigned for Compound (Z)-25 (minor): $^1$H NMR (400 MHz, CDCl$_3$) δ8.03–8.01 (m, 1H), 7.44–7.42 (m, 1H), 7.32–7.22 (m, 2H), 6.91 (s, 1H), 4.73 (s, 2H), 4.27 (d, J=1.20 Hz, 2H), 2.39 (t, J=6.80 Hz, 2H), 2.20 (td, J=6.80, 2.40 Hz, 2H), 1.98–1.95 (m, 1H), 1.75–1.59 (m, 4H), 0.93 (s, 9H), 0.08 (s, 6H); $^{13}$C NMR (100 MHz, CDCl$_3$, recorded as a mixture) δ138.9, 134.2, 133.7, 133.3, 130.0, 128.9, 128.3, 128.1, 127.9, 127.8, 126.8, 126.8, 126.6, 126.5, 125.3, 123.5, 109.4, 96.8, 91.7, 84.1, 80.5, 78.3, 68.6, 68.5, 67.3, 63.2, 63.2, 61.2, 27.7, 27.7, 27.5, 27.4, 26.0, 26.0, 19.3, 19.2, 18.5, 18.4, 18.1, 18.0, −5.1, −5.1; MS (+CI) m/z (relative intensity) 383 (M+H$^+$, 25), 329 (100); HRMS (+EI) calcd for C$_{24}$H$_{34}$O$_2$Si (M$^+$) 382.2328, found 382.2312.

EXAMPLE 26

(E)- and (Z)-2-[2'-((((tert-butyldimethyl)silyloxy)methyl)phenyl)methylidene]-10-iododeca-3,9-diyn-1-ol (Compound 26)

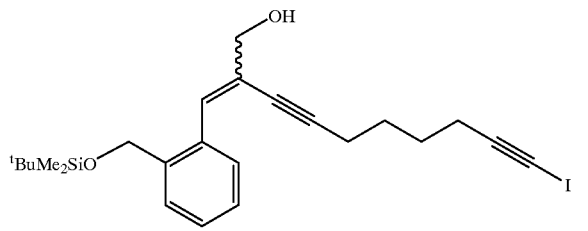

To a solution of iodine (2.31 g, 9.10 mmol) in toluene (50 mL) was added morpholine (2.12 mL, 24.26 mmol) and the resultant mixture was heated at 60° C. for 30 minutes. To this mixture was added a solution of Compound 25 (E:Z=65:35, 1.16 g, 3.03 mmol) in toluene (50 mL) followed by heating at the same temperature for 18 hours. The reaction mixture was allowed to cool down to room temperature, and purified, without aqueous workup, by flash column chromatography directly (silica gel, 100 percent hexane and then 10 percent EtOAc in hexane) to give 1.31 g (85 percent) of Compound 26 as a 67:33 mixture of E:Z isomers: yellow oil; $R_f$=0.34 (20 percent EtOAc in hexane); IR (neat) 3402 (br), 2928, 1256, 1076 cm$^{-1}$; signals assigned for Compound (E)-26 (major): $^1$H NMR (400 MHz, CDCl$_3$) δ7.46 (d, J=7.60 Hz, 1H), 7.32–7.22 (m, 2H), 7.11 (d, J=7.20 Hz, 1H), 6.94 (s, 1H), 4.67 (s, 2H), 4.16 (s, 2H), 2.45–2.34 (m, 4H), 1.72–1.60 (m, 4H), 0.95 (s, 9H), 0.12 (s, 6H); signals assigned for Compound (Z)-26 (minor): $^1$H NMR (400 MHz, CDCl$_3$) δ8.00 (d, J=6.80 Hz, 1H), 7.45–7.43 (m, 1H), 7.32–7.22 (m, 2H), 6.91 (s, 1H), 4.73 (s, 2H), 4.27 (s, 2H), 2.45–2.34 (m, 4H), 1.72–1.60 (m, 4H), 0.93 (s, 9H), 0.08 (s, 6H); $^{13}$C NMR (100 MHz, CDCl$_3$, recorded as a mixture) δ138.9, 138.8, 134.2, 133.7, 133.4, 130.1, 128.9, 128.1, 127.9, 127.8, 126.8, 126.8, 126.6, 126.5, 125.3, 123.5, 96.6, 94.1, 91.6, 80.5, 78.3, 77.2, 67.3, 63.2, 63.2, 63.2, 63.1, 61.2, 27.8, 27.7, 27.6, 27.5, 26.0, 26.0, 20.5, 20.4, 19.3, 19.2, 18.5, 18.4, −5.1, −5.1, −6.6, −6.6; MS (+CI) m/z (relative intensity) 509 (M+H$^+$, 40), 232 (100); HRMS (+EI) calcd for C$_{24}$H$_{33}$IO$_2$Si (M$^+$) 508.1295, found 508.1239.

EXAMPLE 27

(E)-2-[2'-((((tert-butyldimethyl)silyloxy)methyl)phenyl)methylidene]-10-iododeca-3,9-diyn-1-al (Compound 27)

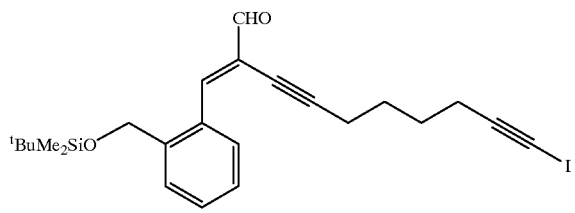

To a solution of Compound 26 (E:Z=67:33, 988.0 mg, 1.00 mmol) and powdered 4 Å molecular sieves in dry CH$_2$Cl$_2$ (30 mL) cooled at 0° C. in an ice-water bath was added PCC (419.0 mg, 1.00 mmol) followed by stirring at room temperature for 2 days. The reaction mixture was diluted with EtOAc (30 mL), filtered through a short silica gel pad with rinsing by EtOAc. The filtrate was concentrated under reduced pressure and the residue was purified by flash column chromatography (silica gel, 5 percent EtOAc in hexane) to give 866.0 mg (88 percent) of Compound 27 as a single isomer; pale yellow oil; $R_f$=0.63 (20 percent EtOAc in hexane); IR (neat) 2930, 2230, 1694, 1592, 1254, 1078 cm$^{-1}$; $^1$H NMR (400 MHz, CDCl$_3$) δ9.58 (s, 1H), 8.49 (d, J=7.60 Hz, 1H), 7.85 (s, 1H), 7.46–7.35 (m, 3H), 4.83 (s, 2H), 2.53 (t, J=6.80 Hz, 2H), 2.40 (t, J=6.80 Hz, 2H), 1.74–1.65 (m, 4H), 0.90 (s, 9H), 0.08 (s, 6H); $^{13}$C NMR (100 MHz, CDCl$_3$) δ191.5, 148.6, 140.5, 132.2, 130.8, 128.8, 127.8, 127.3, 124.3, 101.5, 94.0, 77.2, 74.5, 63.7, 27.6, 27.4, 25.9, 20.5, 19.6, 18.4, −5.1; MS (+CI) m/z (relative intensity) 507 (M+H$^+$45), 248 (100); HRMS (+EI) calcd for C$_{24}$H$_{31}$IO$_2$Si (M$^+$) 506.1138, found 506.1146.

EXAMPLE 28

(E)-4-[2'-((((tert-butyldimethyl)silyloxy)methyl)phenyl)methylidene]cyclodeca-1,5-diyn-3-ol (Compound 28)

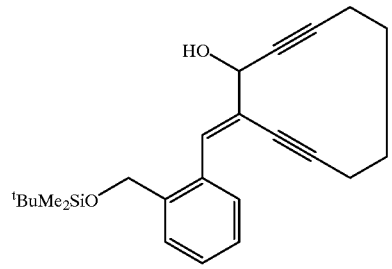

A suspension of CrCl$_2$ (152.1 mg, 1.24 mmol) and NiCl$_2$ (53.5 mg, 0.41 mmol) in dry THF (200 mL) was stirred at room temperature for 3 hours. To this mixture was added a solution of Compound 27 (208.8 mg, 0.41 mmol) in dry THF (5 mL) followed by stirring at room temperature for 8 hours. The reaction was quenched with saturated aqueous NH$_4$Cl (50 mL) and the resultant mixture was concentrated under reduced pressure to a volume of about 100 mL that was then extracted with EtOAc (50 mL×3). The combined organic layer was washed with brine, dried over anhydrous MgSO$_4$, filtered, and concentrated in vacuo. The residue was purified by flash column chromatography (silica gel, 20 percent EtOAc in hexane) to give 40.4 mg (25.8 percent) of Compound 28: colorless oil; $R_f$=0.36 (20 percent EtOAc in hexane); IR (neat) 3408 (br), 2930, 2216, 1074 cm$^{-1}$; $^1$H NMR (300 MHz, CDCl$_3$) δ8.22–8.18 (m, 1H), 7.45–7.42 (m, 1H), 7.31–7.26 (m, 2H), 6.94 (s, 1H), 4.97 (d, J=7.29 Hz, 1H), 4.76 (s, 2H), 2.46–2.37 (m, 2H), 2.30–2.23 (m, 2H), 2.19 (d, J=8.01 Hz, 1H), 1.90–1.70 (m, 4H), 0.93 (s, 9H), 0.09 (s, 6H); $^{13}$C NMR (75 MHz, CDCl$_3$) δ139.7, 134.3, 130.2, 129.5, 128.9, 128.6, 127.5, 126.9, 103.3, 92.2, 82.7, 81.0, 68.9, 63.9, 28.4, 28.2, 26.6, 22.6, 21.3, 19.0, −4.5; MS (+CI) m/z (relative intensity) 381 (M+H$^+$, 8), 363 (100); HRMS (+EI) calcd for C$_{24}$H$_{32}$O$_2$Si (M$^+$) 380.2172, found 380.2187.

EXAMPLE 29

(E)-3-Acetoxy-4-(phenylmethylidene)cyclodeca-1,5-diyne (Compound 29)

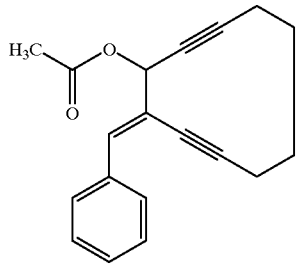

29

To a solution of Compound 6 (23.6 mg, 0.10 mmol) and triethylamine (1 mL) in dry $CH_2Cl_2$ (4 mL) was added acetic anhydride (20.4 mg, 0.20 mmol) followed by stirring at room temperature for 2 hours. The reaction was then quenched with saturated aqueous $NH_4Cl$ and extracted with $CH_2Cl_2$, washed with brine, dried over anhydrous $MgSO_4$, filtered, and concentrated under reduced pressure. The residue was purified by flash column chromatography (silica gel, 10 percent EtOAc in hexane) to give 20.5 mg (74 percent) of Compound 29: pale yellow oil; $R_f$=0.29 (10 percent EtOAc in hexane); IR (neat) 2934, 2234, 2210, 1736, 1448, 1226 $cm^{-1}$; $^1H$ NMR (300 MHz, $CDCl_3$) δ7.91–7.88 (m, 2H), 7.38–7.27 (m, 3H), 6.69 (s, 1H), 6.05 (t, J=1.05 Hz, 1H), 2.60–2.20 (m, 4H), 2.12 (s, 3H), 2.00–1.71 (m, 4H); $^{13}C$ NMR (75 MHz, $CDCl_3$) δ170.1, 135.4, 135.3, 128.7, 128.7, 128.2, 120.4, 104.0, 93.0, 80.4, 78.6, 69.2, 27.6, 27.5, 22.0, 21.4, 20.8; MS (+CI) m/z (relative intensity) 279 (M+H$^+$, 15), 219 (100); HRMS (+EI) calcd for $C_{19}H_{19}O_2$ (M$^+$) 278.1307, found 278.1298.

EXAMPLE 30

(E)-3-Acetoxy-4-[(4'-methoxyphenyl)methylidene]cyclodeca-1,5-diyne (Compound 30a)

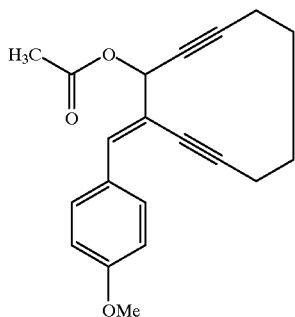

30a

To a solution of Compound 20a (15.5 mg, 5.83×10$^{-2}$ mmol) and DMAP (71.2 mg, 0.58 mmol) in dry $Ch_2Cl_2$ (8 mL) was added acetic anhydride (36 mg, 0.35 mmol) followed by stirring at room temperature for 2 hours. The reaction was then quenched with saturated aqueous $NH_4Cl$ and extracted with $CH_2Cl_2$, washed with brine, dried over anhydrous $MgSO_4$, filtered, and concentrated under reduced pressure. The residue was purified by flash column chromatography (silica gel, 20 percent EtOAc in hexane) to give 7.7 mg (44 percent) of Compound 30a: pale yellow oil; $R_f$=0.44 (20 percent EtOAc in hexane); IR (neat) 2934, 2198, 1738, 1606, 1512, 1232, 1176, 1030 $cm^{-1}$; $^1H$ NMR (300 MHz, acetone-$d_6$) δ8.10–8.06 (AA'BB', 2H), 7.12–7.07 (AA'B', 2H), 6.86 (s, 1H), 6.12 (s, 1H), 3.98 (s, 3H), 2.68–2.36 (m, 4H), 2.21 (s, 3H), 2.10–1.75 (m, 4H); $^{13}C$ NMR (75 MHz, acetone-$d_6$) δ169.2, 160.0, 134.3, 130.0, 128.4, 118.4, 113.5, 103.3, 92.2, 80.4, 78.8, 68.6, 54.6, 27.4, 27.3, 21.1, 20.9, 19.9; MS (+CI) m/z (relative intensity) 309 (M+H$^+$, 8), 249 (100); IRS (+EI) calcd for $C_{20}H_{20}O_3$ (M$^+$) 308.1412, found 308.1405.

EXAMPLE 31

(E)-3-Acetoxy-4-(1'-naphthylmethylidene)cyclodeca-1,5-diyne (Compound 30b)

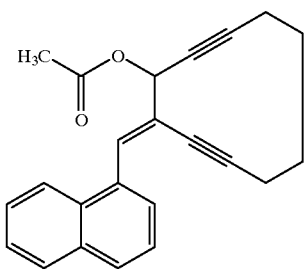

30b

To a solution of Compound 20b (11.4 mg, 3.99×10$^{-2}$ mmol) and DMAP (48.7 mg, 0.40 mmol) in dry $CH_2Cl_2$ (5 mL) was added acetic anhydride (20.3 mg, 0.20 mmol) followed by stirring at room temperature for 2.5 hours. The reaction was then quenched with saturated aqueous $NH_4Cl$ and extracted with $CH_2Cl_2$, washed with brine, dried over anhydrous $MgSO_4$, filtered, and concentrated under reduced pressure. The residue was purified by flash column chromatography (silica gel, 14 percent EtOAc in hexane) to give 9.4 mg (67 percent) of Compound 20b: pale yellow oil; $R_f$=0.34 (14 percent EtOAc in hexane); IR (neat) 2934, 2239, 2229, 1740, 1226, 1012 $cm^{-1}$; $^1H$ NMR (300 MHz, $CDCl_3$) δ8.23 (d, J=7.17 Hz, 1H), 8.02 (d, J=7.65 Hz, 1H), 7.83 (t, J=7.74 Hz, 2H), 7.55–7.48 (m, 3H), 7.46 (s, 1H), 6.22 (s, 1H), 2.55–2.23 (m, 4H), 2.18 (s, 3H), 1.98–1.67 (m, 4H); $^{13}C$ NMR (75 MHz, $CDCl_3$) δ171.0, 134.2, 132.9, 132.2, 129.7, 129.3, 127.0, 126.5, 125.9, 124.1, 123.6, 103.3, 93.8, 80.9, 79.4, 69.7, 28.2, 28.1, 22.5, 22.0, 21.4; MS (+CI) m/z (relative intensity) 329 (M+H$^+$, 20), 269 (100); HRMS (+EI) calcd for $C_{23}H_{20}O_2$ (M$^+$) 328.1463, found 328.1461.

EXAMPLE 32

(E)-3-Acetoxy-4-(2'-naphthylmethylidene)cyclodeca-1,5-diyne (Compound 30c)

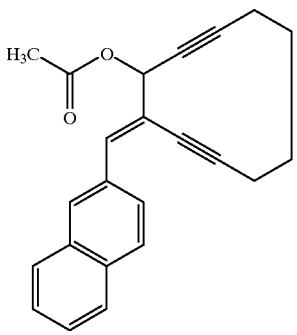

30c

To a solution of Compound 20c (20.1 mg, 7.03×10$^{-2}$ mmol) and DMAP (85.8 mg, 0.70 mmol) in dry $CH_2Cl_2$ (8 mL) was added acetic anhydride (36 mg, 0.35 mmol) followed by stirring at room temperature for 3 hours. The reaction was then quenched with saturated aqueous $NH_4Cl$ and extracted with $CH_2Cl_2$, washed with brine, dried over anhydrous $MgSO_4$, filtered, and concentrated under reduced pressure. The residue was purified by flash column chromatography (silica gel, 25 percent EtOAc in hexane) to give 15.6 mg (68 percent) of Compound 30c: pale yellow oil; $R_f$=0.52 (25 percent EtOAc in hexane); IR (neat) 2934, 2239, 2229, 1740, 1224, 1012 cm$^{-1}$; $^1$H NMR (300 MHz, CDCl$_3$) δ8.23–8.19 (m, 2H), 7.85–7.79 (m, 3H), 7.53–7.43 (m, 2H), 6.86 (s, 1H), 6.11 (s, 1H), 2.65–2.42 (m, 2H), 2.39–2.25 (m, 2H), 2.15 (s, 3H), 2.00–1.67 (m, 4H); $^{13}$C NMR (75 MHz, CDCl$_3$) δ171.0, 136.2, 134.1, 133.9, 133.8, 129.6, 129.1, 128.5, 128.3, 127.2, 126.8, 126.4, 121.5, 104.8, 93.7, 81.2, 79.3, 70.0, 28.2, 28.1, 22.6, 22.0, 21.4; MS (+CI) m/z (relative intensity) 329 (M+H$^+$, 23), 269 (100); HRMS (+EI) calcd for $C_{23}H_{20}O_2$ (M$^+$) 328.1463, found 328.1468.

EXAMPLE 33

(E)-3-Methoxyacetoxy4-(phenylmethylidene)cyclodeca-1,5-diyne (Compound 31)

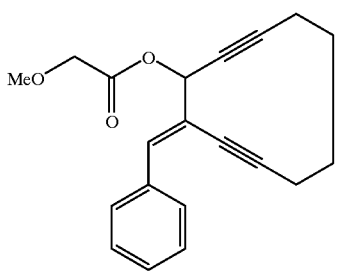

31

To a solution of Compound 6 (50 mg, 0.216 mmol), DCC (446 mg, 2.16 mmol) and DMAP (264 mg, 2.16 mmol) in dry $CH_2Cl_2$ (10 mL) cooled in an ice-water bath was added methoxyacetic acid (194.6 mg, 2.16 mmol) followed by stirring at room temperature for 12 hours. The reaction mixture was filtered through a short plug of Celite with rinsing by EtOAc. The filtrate was concentrated under reduced pressure and the residue was purified by flash column chromatography (silica gel, 20 percent EtOAc in hexane) to give 43.2 mg (66 percent) of Compound 31: pale yellow oil; $R_f$=0.40 (20 percent EtOAc-hexane); IR (neat) 2932, 2234, 2210, 1754, 1182, 1124cm$^{-1}$; $^1$H NMR (300 MHz, CDCl$_3$) δ7.89 (d, J=7.08 Hz, 2H), 7.39–7.26 (m, 3H), 6.72 (s, 1H), 6.16 (d, J=0.93 Hz, 1H), 4.12 (s, 2H), 3.45 (s, 3H), 2.60–2.25 (m, 4H), 1.94–1.66 (m, 4H); $^{13}$C NMR (75 MHz, CDCl$_3$) δ170.2, 136.5, 136.0, 129.5, 129.4, 129.0, 120.9, 104.8, 94.3, 80.9, 78.8, 70.4, 70.3, 60.1, 28.1, 28.0, 22.5, 21.3; MS (+CI) m/z (relative intensity) 309 (M+H$^+$, 20); HRMS (+EI) calcd for $C_{20}H_{20}O_3$ (M$^+$) 308.1412, found 308.1403.

EXAMPLE 34

(E)-3-Methoxyacetoxy-4-[(4'-methoxyphenyl)methylidene]cyclodeca-1,5-diyne (Compound 32a)

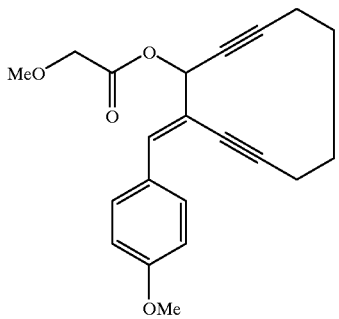

32a

To a solution of Compound 20a (20.4 mg, 7.67×10$^{-2}$ mmol), DCC (15.8 mg, 7.67×10$^{-2}$ mmol), and DMAP (93.6 mg, 0.77 mmol) in dry $CH_2Cl_2$ (10 mL) cooled in an ice-water bath was added methoxyacetic acid (69 mg, 0.77 mmol) followed by stirring at room temperature for 6 hours. The reaction mixture was filtered through a short plug of Celite with rinsing by EtOAc. The filtrate was concentrated under reduced pressure to give the crude Compound 32a that was converted into Compound 33 over silica gel during flash column chromatographic purification.

EXAMPLE 35

(E)-3-Methoxyacetoxy-4-(1'-naphthylmethylidene)cyclodeca-1,5-diyne (Compound 32b)

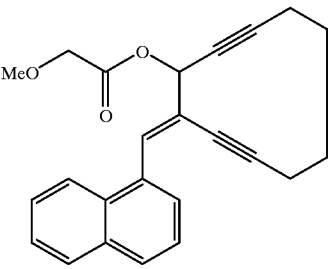

32b

To a solution of Compound 20b (37 mg, 0.13 mmol), DCC (26.7 mg, 0.13 mmol), and DMAP (31.6 mg, 0.26 mmol) in dry $CH_2Cl_2$ (20 mL) cooled in an ice-water bath was added methoxyacetic acid (17.5 mg, 0.19 mmol) followed by stirring at room temperature for 2 hours. The reaction mixture was filtered through a short plug of Celite with rinsing by EtOAc. The filtrate was concentrated under reduced pressure and the residue was purified by flash column chromatography (silica gel, 20 percent EtOAc in hexane) to give 30.1 mg (65 percent) of Compound 30b: pale yellow oil; $R_f$=0.38 (20 percent EtOAc in hexane); IR (neat) 2932, 2239,2229, 1756, 1182, 1126 cm$^{-1}$; $^1$H NMR (300 MHz, CDCl$_3$) δ8.32 (d, J=7.29 Hz, 1H), 8.14–8.00 (m, 1H), 7.92–7.81 (m, 2H), 7.58–7.44 (m, 3H), 7.50 (s, 1H), 6.33 (t, J=1.05 Hz, 1H), 4.15 and 4.13 (AB q, J=16.50 Hz, 2H), 3.48 (s, 3H), 2.55–2.20 (m, 4H), 2.00–1.60 (m, 4H); $^{13}$C NMR (75 MHz, CDCl$_3$) δ170.4, 134.2, 133.4, 132.8, 132.2, 129.8, 129.3, 127.1, 127.0, 126.5, 125.9, 124.1, 123.3, 103.5, 94.4, 80.8, 79.0, 70.6, 70.2, 60.1, 28.2, 28.1, 22.5, 21.4; MS (+CI) m/z (relative intensity) 359 (M+H$^+$, 4), 269 (100); HRMS (+EI) calcd for C$_{24}$H$_{22}$O$_3$ (M$^+$) 358.1569, found 358.1574.

EXAMPLE 36

(E)-3-Methoxyacetoxy-4-(2'-naphthylmethylidene) cyclodeca-1,5-diyne (Compound 32c)

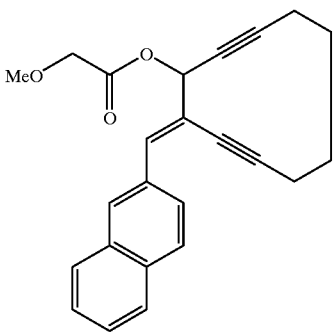

32c

To a solution of Compound 20c (30 mg, 0.10 mmol), DCC (21.6 mg, 0.10 mmol), and DMAP (128 mg, 1.05 mmol) in dry CH$_2$Cl$_2$ (10 mL) cooled in an ice-water bath was added methoxyacetic acid (18.8 mg, 0.21 mmol) followed by stirring at room temperature for 6 hours. The reaction mixture was filtered through a short plug of Celite with rinsing by EtOAc. The filtrate was concentrated under reduced pressure and the residue was purified by flash column chromatography (silica gel, 25 percent EtOAc in hexane) to give 24.4 mg (65 percent) of Compound 32c: pale yellow oil; $R_f$=0.50 (25 percent EtOAc in hexane); IR (neat) 2932, 2222, 2212, 1754, 1182, 1124 cm$^{-1}$; $^1$H NMR (300 MHz, CDCl$_3$) δ8.25–8.19 (m, 2H), 7.95–7.77 (m, 3H), 7.57–7.45 (m, 2H), 6.90 (s, 1H), 6.23 (s, 1H), 4.13 (s, 2H), 3.47 (s, 3H), 2.68–2.20 (m, 4H), 2.03–1.67 (m, 4H); $^{13}$C NMR (75 MHz, CDCl$_3$) δ170.3, 136.7, 134.2, 133.8, 133.7, 129.7, 129.1, 128.5, 128.3, 127.2, 126.9, 126.4, 121.2, 104.9, 94.4, 81.1, 78.9, 76.2, 70.5, 60.1, 28.2, 28.1, 22.6, 21.4; MS (+CI) m/z (relative intensity) 359 (M+H$^+$, 18), 269 (100); HRMS (+EI) calcd for C$_{24}$H$_{22}$O$_3$ (M$^+$) 358.1569, found 358.1594.

EXAMPLE 37

3-[1'-Hydroxy-1'-(4''-methoxyphenyl)methyl] cyclodeca-3-en-1,5-diyne (Compound 33)

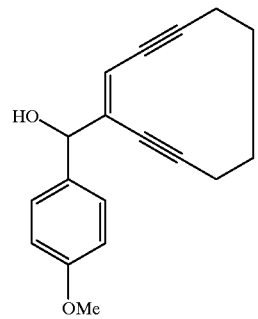

33

Obtained from crude Compound 32a after purification by flash column chromatography (silica gel, 20 percent EtOAc in hexane) (in 43 percent yield calculated from Compound 20a). Compound 32a: pale yellow oil; $R_f$=0.37 (20 percent EtOAc in hexane); IR (neat) 3426 (br), 2934, 2194, 1610, 1512, 1248, 1174, 1032 cm$^{-1}$; $^1$H NMR (300 MHz, CDCl$_3$) δ7.37–7.32 (AA'BB', 2H), 6.92–6.87 (AA'BB', 2H), 5.88 (s, 1H), 5.20 (br s, 1H), 3.80 (s, 3H), 2.42–2.30 (m, 4H), 2.11 (d, J=3.66 Hz, 1H), 1.94–1.85 (m, 4H); $^{13}$C NMR (75 MHz, CDCl$_3$) δ160.1, 142.4, 134.2, 128.7, 118.5, 114.6, 106.5, 103.4, 83.5, 81.9, 75.1, 56.0, 29.5, 29.3, 22.5, 22.4; MS (+CI) m/z (relative intensity) 267 (M+H$^+$, 58), 249 (100); HRMS (+EI) calcd for C$_{18}$H$_{18}$O$_2$ (M$^+$) 266.1307, found 266.1300.

EXAMPLE 38

(E)-3-Acetoxy-4-[2'-((((tert-butyldimethyl)silyloxy) methyl)phenyl)methylidene]cyclodeca-1,5-diyne (Compound 34a)

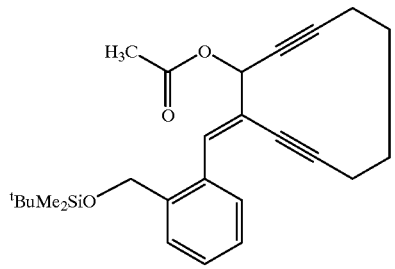

34a

To a solution of Compound 28 (40.4 mg, 0.11 mmol) and DMAP (64.9 mg, 0.53 mmol) in dry CH$_2$Cl$_2$ (4 mL) was added acetic anhydride (54.2 mg, 0.53 mmol) followed by stirring at room temperature for 15 minutes. The reaction was then quenched with saturated aqueous NH$_4$Cl and extracted with CH$_2$Cl$_2$, washed with brine, dried over anhydrous MgSO$_4$, filtered, and concentrated under reduced pressure. The residue was purified by flash column chromatography (silica gel, 20 percent EtOAc in hexane) to give 36.8 mg (82 percent) of Compound 34a: pale yellow oil; $R_f$=0.57 (20 percent EtOAc in hexane); IR (neat) 2930, 2236, 1740, 1224, 1076 cm$^{-1}$; $^1$H NMR (300 MHz, CDCl$_3$) δ8.15–8.12 (m, 1H), 7.39–7.36 (m, 1H), 7.25–7.20 (m, 2H), 6.86 (s, 1H), 5.96 (s, 1H), 4.67 (s, 2H), 2.41–2.20 (m, 4H), 2.07 (s, 3H), 1.86–1.78 (m, 4H), 0.87 (s, 9H), 0.03 (s, 6H); $^{13}$C NMR (75 MHz, CDCl$_3$) δ170.8, 140.0, 134.0, 132.8, 129.2, 128.6, 127.6, 127.5, 122.8, 103.3, 93.6, 80.9, 79.4, 69.7, 63.8, 28.2, 28.1, 26.6, 22.5, 21.9, 21.4, 19.0, −4.6; MS (+CI) m/z (relative intensity) 423 (M+H$^+$, 25), 363 (100); HRMS (+EI) calcd for C$_{26}$H$_{34}$O$_3$Si (M$^+$) 422.2277, found 422.2268.

EXAMPLE 39

(E)-4-[2'-((((tert-butyldimethyl)silyloxy)methyl)phenyl)methylidene]-3-(methoxyacetoxy)cyclodeca-1,5-diyne (Compound 34b)

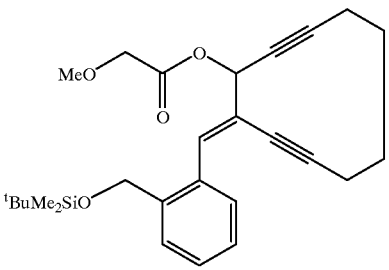

34b

To a solution of Compound 28 (27.0 mg, 0.07 mmol), DCC (29.3 mg, 0.14 mmol) and DMAP (17.3 mg, 0.14 mmol) in dry CH$_2$Cl$_2$ cooled in an ice-water bath was added methoxyacetic acid (12.8 mg, 0.14 mmol) followed by stirring at room temperature for 4 hours. The reaction mixture was filtered through a short plug of Celite with rinsing by EtOAc. The filtrate was concentrated under reduced pressure and the residue was purified by flash column chromatography (silica gel, 14 percent EtOAc in hexane) to give 24.6 mg (77 percent) of Compound 34b: pale yellow oil; R$_f$ 0.39 (14 percent EtOAc in hexane); IR (neat) 2932, 2234, 1758, 1254, 1182, 1124, 1076 cm$^{-1}$; $^1$H NMR (300 MHz, CDCl$_3$) δ8.20–8.17 (m, 1H), 7.44–7.42 (m, 1H), 7.31–7.27 (m, 2H), 6.93 (s, 1H), 6.13 (s, 1H), 4.73 (s, 2H), 4.11 and 4.06 (AB q, J=13.65 Hz, 2H), 3.46 (s, 3H), 2.48–2.25 (m, 4H), 1.92–1.71 (m, 4H), 0.92 (s, 9H), 0.09 (s, 3H), 0.08 (s, 3H); $^{13}$C NMR (75 MHz, CDCl$_3$) δ170.2, 140.1, 133.8, 133.2, 129.3, 128.6, 127.5, 122.5, 103.3, 94.2, 80.7, 79.0, 70.5, 70.2, 63.7, 60.1, 28.2, 28.1, 26.6, 22.5, 21.4, 19.0, −4.6; MS (+CI) m/z (relative intensity) 453 (M+H$^+$, 15), 363 (100); HRMS (+EI) calcd for C$_{27}$H$_{36}$O$_4$Si (M$^+$) 452.2383, found 452.2392.

EXAMPLE 40

(E)-3-Acetoxy-4-[2'-((hydroxymethyl)phenyl)methylidene]cyclodeca-1,5-diyne (Compound 35a)

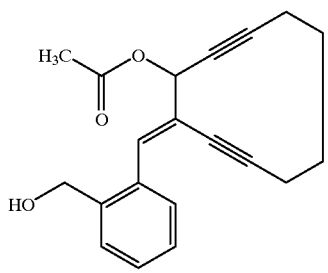

35a

To a solution of Compound 34a (24.5 mg, 5.8×10$^{-2}$ mmol) in methanol (2 mL) was added PPTS (2.92 mg, 1.2×10$^{-2}$ mmol) followed by stirring at room temperature for 16 hours. The reaction mixture was then concentrated under reduced pressure, the residue was purified by flash column chromatography (silica gel, 20 percent EtOAc in hexane) to give 14.8 mg (83 percent) of Compound 35a: colorless oil; R$_f$=0.14 (20 percent EtOAc in hexane); IR (neat) 3422 (br), 2932, 2234, 1736, 1226, 1014 cm$^{-1}$; $^1$H NMR (300 MHz, CDCl$_3$) δ8.24–8.21 (m, 1H), 7.40–7.27 (m, 3H), 7.03 (s, 1H), 6.07 (t, J=1.09 Hz, 1H), 4.75 and 4.69 (AB q, J=12.75 Hz, 2H), 2.47–2.27 (m, 4H), 2.13 (s, 3H), 1.93–1.61 (m, 5H); $^{13}$C NMR (75 MHz, CDCl$_3$) δ171.1, 139.5, 134.8, 132.8, 129.4, 129.0, 128.9, 128.4, 123.4, 103.7, 93.8, 80.7, 79.3, 69.8, 64.0, 28.2, 28.1, 22.5, 22.0, 21.4; MS (+CI) m/z (relative intensity) 309 (M+H$^+$, 11), 249 (100); HRMS (+EI) calcd for C$_{20}$H$_{20}$O$_3$ (M$^+$) 308.1412, found 308.1408.

EXAMPLE 41

(E)-4-[2'-(Hydroxymethyl)phenyl]methylidene]-3-(methoxyacetoxy)cyclodeca-1,5-diyne (Compound 35a)

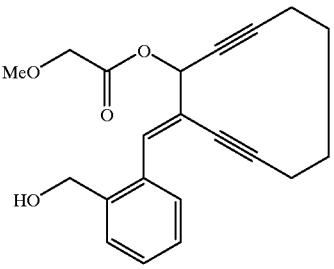

35b

To a solution of Compound 34b (24.6 mg, 5.44×10$^{-2}$ mmol) in methanol (2 mL) was added PPTS (2.73 mg, 1.09×10$^{-2}$ mmol) followed by stirring at room temperature for 17 hours. The reaction mixture was then concentrated under reduced pressure, the residue was purified by flash column chromatography (silica gel, 33 percent EtOAc in hexane) to give 7.4 mg (40 percent) of Compound 35b: pale yellow oil; $R_f$=0.14 (33 percent EtOAc in hexane); IR (neat) 3448 (br), 2932, 2234, 1752, 1186, 1124 cm$^{-1}$; $^1$H NMR (300 MHz, CDCl$_3$) δ8.24– 8.20 (m, 1H), 7.40–7.27 (m, 3H), 7.06 (s, 1H), 6.17 (s, 1H), 4.72 and 4.69 (AB q, J=12.99 Hz, 2H), 4.11 and 4.07 (AB q, J=16.23 Hz, 2H), 3.46 (s, 3H), 2.53–2.26 (m, 4H), 1.93–1.61 (m, 5H); $^{13}$C NMR (75 MHz, CDCl$_3$) δ170.4, 139.5, 134.7, 133.2, 129.5, 129.0, 128.9, 128.4, 123.0, 103.9, 94.4, 80.6, 78.8, 70.5, 70.2, 64.0, 60.1, 28.2, 28.1, 22.5, 21.4; MS (+CI) m/z (relative intensity) 338 (M+H$^+$20), 249 (100); HRMS (+EI) calcd for C$_{21}$H$_{22}$O$_4$ (M$^+$) 338.1518, found 338.1523.

EXAMPLE 42

(E)-4-(1'-Naphthylmethylidene)-3-(propanoyloxy) cyclodeca-1,5-diyne (Compound 36)

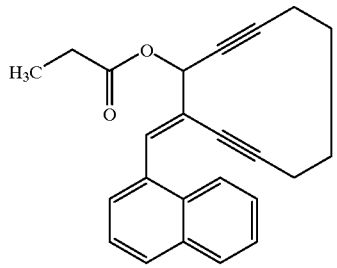

To a solution of Compound 20b (10.0 mg, 3.50×10$^{-2}$ mmol), DCC (7.2 mg, 3.50×10$^{-2}$ mmol), and DMAP (8.5 mg, 6.99×10$^{-2}$ mmol) in dry CH$_2$Cl$_2$ (4 mL) cooled in an ice-water bath was added propionic acid (3.8 mg, 5.24×10$^{-2}$ mmol) followed by stirring at room temperature for 4 hours. The reaction mixture was filtered through a short plug of Celite with rinsing by EtOAc. The filtrate was concentrated under reduced pressure and the residue was purified by flash column chromatography (silica gel, 20 percent EtOAc in hexane) to give 8.3 mg (69 percent) of Compound 36: pale yellow oil; $R_f$=0.43 (20 percent EtOAc in hexane); IR (neat) 2958, 2235, 1726, 1189, 1067 cm$^{-1}$; $^1$H NMR (300 MHz, CDCl$_3$) δ8.31 (d, J=7.23 Hz, 1H), 8.01 (d, J=7.56 Hz, 1H), 7.83 (t, J=8.01 Hz, 2H), 7.54–7.46 (m, 3H), 7.45 (s, 1H), 6.24 (s, 1H), 2.52–2.24 (m, 6H), 1.96–1.67 (m, 4H), 1.20 (t, J=7.56 Hz, 3H); $^{13}$C NMR (75 MHz, CDCl$_3$) δ174.5, 134.2, 133.0, 132.7, 132.2, 129.7, 129.3, 127.0, 127.0, 126.5, 126.0, 124.2, 123.8, 103.3, 93.6, 81.0, 79.5, 69.4, 28.5, 28.3, 28.2, 22.6, 21.5, 9.8; MS (+CI) m/z (relative intensity) 342 (M$^+$, 5), 269 (100).

EXAMPLE 43

(E)-4-(1'-Naphthylmethylidene)-3-(octanoyloxy) cyclodeca-1,5-diyne (Compound 37)

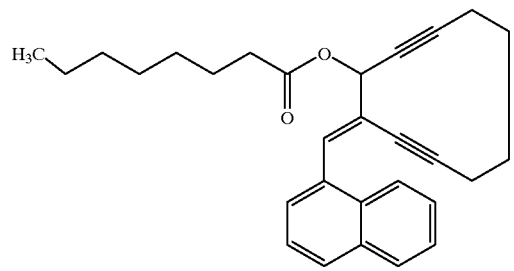

To a solution of Compound 20b (10.0 mg, 3.50×10$^{-2}$ mmol), DCC (7.2 mg, 3.50×10$^{-2}$ mmol), and DMAP (8.5 mg, 6.99×10$^{-2}$ mmol) in dry Ch$_2$Cl$_2$ (4 mL) cooled in an ice-water bath was added n-octanoic acid (7.5 mg, 5.24×10$^{-2}$ mmol) followed by stirring at room temperature for 4 hours. The reaction mixture was filtered through a short plug of Celite with rinsing by EtOAc. The filtrate was concentrated under reduced pressure and the residue was purified by flash column chromatography (silica gel, 20 percent EtOAc in hexane) to give 11.2 mg (78 percent) of Compound 37: pale yellow oil; $R_f$=0.65 (20 percent EtOAc in hexane); IR (neat) 2932, 1724, 1177, 1037 cm$^{-1}$; $^1$H NMR (300 MHz, CDCl$_3$) δ8.31 (d, J=7.26 Hz, 1H), 8.01 (d, J=7.41 Hz, 1H), 7.86–7.78 (m, 2H), 7.56–7.46 (m, 3H), 7.44 (s, 1H), 6.24 (s, 1H), 2.54–2.22 (m, 4H), 2.42 (t, J=7.53 Hz, 2H), 1.97–1.60 (m, 6H), 1.40–1.16 (m, 8H), 0.84 (t, J=7.02 Hz, 3H); $^{13}$C NMR (75 MHz, CDCl$_3$) δ173.9, 134.2, 133.0, 132.7, 132.2, 129.6, 129.3, 127.0, 127.0, 126.5, 126.0, 124.2, 123.8, 103.2, 93.6, 80.9, 79.5, 69.2, 35.2, 32.3, 29.7, 29.6, 28.3, 28.2, 25.7, 23.3, 22.6, 21.4, 14.7; MS (+CI) m/z (relative intensity) 413 (M+, 6), 269 (100).

EXAMPLE 44

(E)-3-(Benzyloxy)acetoxy4-(1'-naphthylmethylidene)cyclodeca-1,5-diyne (Compound 38)

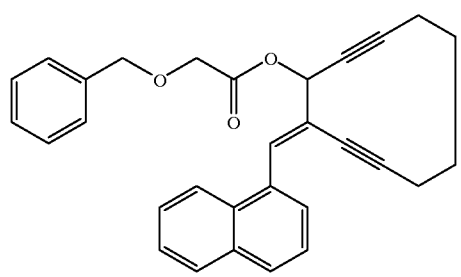

To a solution of Compound 20b (12.1 mg, 4.37×10$^{-2}$ mmol) and DMAP (57.5 mg, 0.44 mmol) in dry Ch$_2$Cl$_2$ (5 mL) cooled in an ice-water bath was added benzyloxyacetyl chloride (16.1 mg, 8.74×10$^{-2}$ mmol) followed by stirring at room temperature for 4 hours. The reaction mixture was concentrated under reduced pressure and the residue was purified by flash column chromatography (silica gel, 20 percent EtOAc in hexane) to give 13.5 mg (73 percent) of Compound 38: pale yellow oil; $R_f$=0.52 (20 percent EtOAc in hexane); IR (neat) 2956, 2212, 1755, 1188, 1069 cm$^{-1}$; $^1$H NMR (300 MHz, CDCl$_3$) δ8.32 (d, J=7.44 Hz, 1H), 8.09–8.00 (m, 1H), 7.92–7.79 (m, 2H), 7.58–7.46 (m, 3H), 7.44–7.28 (m, 6H), 6.33 (t, J=1.35 Hz, 1H), 4.68 (s, 2H), 4.24 and 4.18 (AB q, J=16.59 Hz, 2H), 2.52–2.22 (m, 4H), 1.98–1.66 (m, 4H); $^{13}$C NMR (75 MHz, CDCl$_3$) δ170.5, 134.2, 133.4, 132.6, 131.9, 129.8, 129.3, 129.2, 128.9, 128.7, 127.1, 127.0, 126.5, 125.9, 124.1, 123.4, 121.3, 103.4, 94.5, 80.8, 79.0, 74.1, 70.2, 68.0, 28.2, 28.1, 22.5, 21.4; MS (+CI) m/z (relative intensity) 435 (M$^+$, 1), 271 (100).

EXAMPLE 45

(E)-3-[(4'-Methoxybenzyl)oxy]acetoxy-4-(1''-naphthylmethylidene)cyclodeca-1,5-diyne (Compound 39)

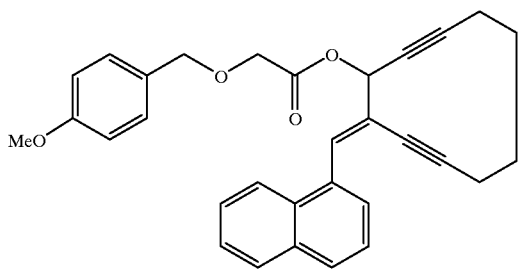

39

To a solution of Compound 20b (14.2 mg, 4.97×10$^{-2}$ mmol), DCC (10$_{-2}$ mg, 4.97×10$_{-2}$ mmol), and DMAP (12.1 mg, 9.93×10$^{-2}$ mmol) in dry CH$_2$Cl$_2$ (5 mL) cooled in an ice-water bath was added p-methoxybenzyloxyacetic acid (13.4 mg, 7.45×10$^{-2}$ mmol) followed by stirring at room temperature for 15 hours. The reaction mixture was filtered through a short plug of Celite with rinsing by EtOAc. The filtrate was concentrated under reduced pressure and the residue was purified by flash column chromatography (silica gel, 14 percent EtOAc in hexane) to give 16.3 mg (71 percent) of Compound 39: pale yellow oil; $R_f$=0.44 (14 percent EtOAc in hexane); IR (neat) 2935, 2213, 1755, 1514, 1250, 1181, 1118 cm$^{-1}$; $^1$H NMR (300 MHz, CDCl$_3$) δ8.31 (d, J=7.26 Hz, 1H), 8.04–7.98 (m, 1H), 7.88–7.79 (m, 2H), 7.56–7.45 (m, 4H), 7.35–7.27 (AA'BB', 2H), 6.91–6.83 (AA'BB', 2H), 6.32 (s, 1H), 4.60 (s, 2H), 4.20 and 4.14 (AB q, J=16.68 Hz, 2H), 3.78 (s, 3H), 2.52–2.20 (m, 4H), 1.97–1.66 (m, 4 H); $^{13}$C NMR (75 MHz, CDCl$_3$) δ170.6, 160.2, 134.2, 133.4, 132.8, 132.2, 131.0, 130.6, 129.8, 129.3, 127.3, 127.1, 127.0, 126.6, 125.9, 124.2, 123.4, 114.6, 103.4, 94.4, 80.8, 79.0, 73.7, 70.2, 67.6, 56.0, 28.2, 28.1, 22.5, 21.4; MS (+CI) m/z (relative intensity) 465 (M$^+$, 0.1), 120 (100).

EXAMPLE 46

(E)-4-(1'-Naphthylmethylidene)-3-((2'',5''-dimethoxybenzoyl)oxy)cyclodeca-1,5-diyne (Compound 40)

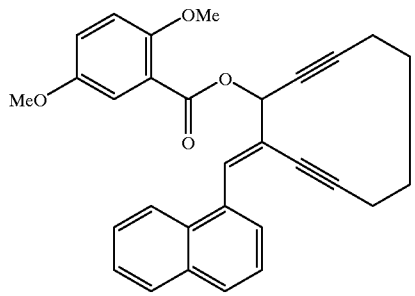

40

To a solution of Compound 20b (18.6 mg, 6.50×10$^{-2}$ mmol), DCC (13.4 mg, 6.50×10$^{31\ 2}$ mmol), and DMAP (15.8 mg, 0.13 mmol) in dry CH$_2$Cl$_2$ (4 mL) cooled in an ice-water bath was added 2,5-dimethoxybenzoic acid (17.8 mg, 9.76×10$^{-2}$ mmol) followed by stirring at room temperature for 24 hours. The reaction mixture was filtered through a short plug of Celite with rinsing by EtOAc. The filtrate was concentrated under reduced pressure and the residue was purified by flash column chromatography (silica gel, 20 percent EtOAc in hexane) to give 21.7 mg (74 percent) of Compound 40: pale yellow oil; $R_f$ 0.33 (20 percent EtOAc in hexane); IR (neat) 2958, 2235, 1721, 1640, 1189, 1064 cm$^{-1}$; $^1$H NMR (300 MHz, CDCl$_3$) δ8.32 (d, J=7.26 Hz, 1H), 8.08–8.04 (m, 1H), 7.88–7.78 (m, 2H), 7.60 (s, 1H), 7.54–7.42 (m, 4H), 7.03 (dd, J=9.03 and 3.39 Hz, 1H), 6.92 (d, J=9.03 Hz, 1H), 6.45 (s, 1 H), 3.84 (s, 3H), 3.80 (s, 3H), 2.46–2.25 (m, 4H), 1.95–1.70 (m, 4H); $^{13}$C NMR (75 MHz, CDCl$_3$) δ169.9, 154.5, 153.7, 134.2, 133.3, 132.2, 129.5, 129.2, 127.0, 126.9, 126.4, 126.0, 124.3, 123.7, 120.3, 117.1, 114.6, 103.1, 93.5, 81.0, 79.5, 69.6, 57.6, 56.6, 28.3, 28.1, 22.6, 21.5; MS (+CI) m/z (relative intensity) 451 (M$^+$, 3), 164 (100).

EXAMPLE 47

(E)-3-[(1'-Anthracenecarbonyl)oxy]-4-(1''-naphthylmethylidene)cyclodeca-1,5-diyne (Compound 41)

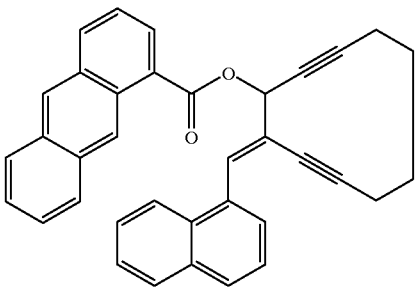

41

To a solution of Compound 20b (18.6 mg, 6.50×10$^{-2}$ mmol), DCC (13.4 mg, 6.50×10$^{-2}$ mmol), and DMAP (15.8 mg, 0.13 mmol) in dry CH$_2$Cl$_2$ (4 mL) cooled in an ice-water bath was added 1-anthracenecarboxylic acid (21.7 mg, 9.76×10⁻² mmol) followed by stirring at room temperature for 24 hours. The reaction mixture was filtered through a short plug of Celite with rinsing by EtOAc. The filtrate was concentrated under reduced pressure and the residue was purified by flash column chromatography (silica gel, 20 percent EtOAc in hexane) to give 23.0 mg (72 percent) of Compound 41: pale yellow oil; $R_f$=0.48 (20 percent EtOAc in hexane); IR (neat) 2933, 2196, 1714, 1263, 1217, 1108 cm⁻¹; MS (+CI) m/z (relative intensity) 491 (M⁺, 3).

EXAMPLE 48

3-[(1'-Methoxyacetoxy-1'-phenyl)methyl]cyclodeca-3-en-1,5-diyne (Compound 42)

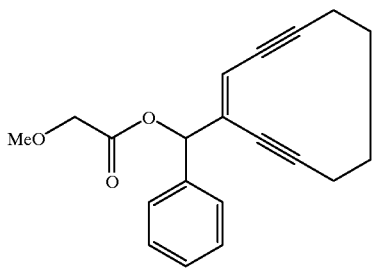

Method A

To a solution of Compound 31 (64.0 mg, 2.08×10⁻¹ mmol) in CHCl₃ (5 mL) was added Eu(fod)₃ (21.5 mg, 2.08×10⁻² mmol) followed by stirring at room temperature for 48 hours. The reaction mixture was then concentrated under reduced pressure and the residue was purified by flash column chromatography (silica gel, 20 percent EtOAc in hexane) to give 50.6 mg (79 percent) of Compound 42: colorless oil; $R_f$=0.43 (20 percent EtOAc in hexane); IR (neat) 2932, 2194, 1758, 1182, 1126 cm⁻¹; ¹H NMR (300 MHz, CDCl₃) δ7.42–7.29 (m, 5 H), 6.39 (s, 1H), 5.85 (s, 1H), 4.15 and 4.07 (AB q, J=16.50 Hz, 2H), 3.45 (s, 3H), 2.40–2.32 (m, 4H), 1.93–1.83 (m, 4H); ¹³C NMR (75 MHz, CDCl₃) δ169.8, 138.0, 137.8, 129.2, 128.0, 120.7, 106.4, 104.5, 83.1, 81.6, 77.9, 76.1, 70.5, 60.1, 29.4, 29.2, 22.4, 22.3; MS (+CI) m/z (relative intensity) 326 (M+NH₄⁺, 10), 219 (100); HRMS (+EI) calcd for C₂₀H₂₀O₃ (M⁺) 308.1412, found 308.1428.

Method B

In a similar procedure as described for Method A, except for using Pr(fod)₃ to replace Eu(fod)₃, Compound 42 was prepared from Compound 31 in 59 percent yield.

Method C

In a similar procedure as described for Method A, except for using Er(fod)₃ to replace Eu(fod)₃, Compound 42 was prepared from Compound 31 in 57 percent yield.

Method D

In a similar procedure as described for Method A, except for using Yb(fod)₃ to replace Eu(fod)₃, Compound 42 was prepared from Compound 31 in 58 percent yield.

EXAMPLE 49

3-[(1'-Methoxyacetoxy-1'-(1"-naphthyl))methyl]cyclodeca-3-en-1,5-diyne (Compound 43a)

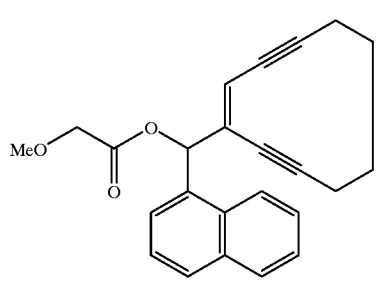

To a solution of Compound 32b (20.0 mg, 5.59×10⁻² mmol) in CHCl₃ (2 mL) was added Eu(fod)₃ (5.8 mg, 5.59×10⁻¹ mmol) followed by stirring at room temperature for 24 hours. The reaction mixture was then concentrated under reduced pressure and the residue was purified by flash column chromatography (silica gel, 20 percent EtOAc in hexane) to give 11.7 mg (59 percent) of Compound 43a: pale yellow oil; $R_f$=0.35 (14 percent EtOAc in hexane); IR (neat) 2932, 2194, 1758, 1182,1126cm⁻¹; ¹H NMR (300 MHz, CDCl₃) δ8.07 (d, J=8.01 Hz, 1H), 7.88–7.81 (m, 2H), 7.67 (d, J=7.02 Hz, 1H), 7.56–7.43 (m, 3H), 7.17 (s, 1H), 5.79 (s, 1H), 4.19 and 4.09 (AB q, J=16.47 Hz, 2H), 3.48 (s, 3H), 2.343–2.30 (m, 4 H), 1.97–1.84 (m, 4H); ¹³C NMR (75 MHz, CDCl₃) δ169.9, 137.7, 134.5, 133.5, 131.3, 130.1, 129.5, 127.3, 126.6, 126.5, 125.9, 124.2, 121.3, 106.4, 104.8, 83.2, 81.9, 73.2, 70.5, 60.1, 29.4, 29.2, 22.4, 22.4; MS (+CI) m/z (relative intensity) 359 (M+H⁺, 7), 271 (100); HRMS (+EI) calcd for C₂₄H₂₂O₃ (M⁺) 358.1569, found 358.1614.

EXAMPLE 50

3-[(1'-Methoxyacetoxy-1'-(2"-naphthyl))methyl]cyclodeca-3-en-1,5-diyne (Compound 43b)

To a solution of Compound 32c (12.6 mg, 3.52×10⁻² mmol) in CHCl₃ (2 mL) was added Eu(fod)₃ (3.6 mg, 3.52×10⁻³ mmol) followed by stirring at room temperature for 40 hours. The reaction mixture was then concentrated under reduced pressure and the residue was purified by flash column chromatography (silica gel, 20 percent EtOAc in hexane) to give 10.0 mg (79 percent) of Compound 43b: pale yellow oil; $R_f$=0.33 (20 percent EtOAc in hexane); IR (neat) 2932, 2194, 1760, 1184, 1124 cm⁻¹; ¹H NMR (300

MHz, CDCl₃) δ7.93–7.80 (m, 4H), 7.53–7.46 (m, 3H), 6.57 (s, 1H), 5.92 (s, 1H), 4.19 and 4.10 (AB q, J=16.50 Hz, 2H), 3.45 (s, 3H), 2.42–2.38 (m, 4H), 1.97–1.83 (m, 4H); $^{13}$C NMR (75 MHz, CDCl₃) δ169.8, 137.8, 135.4, 134.0, 133.8, 129.1, 128.9, 128.4, 127.4, 127.1, 127.0, 125.5, 120.8, 106.6, 104.6, 83.1, 81.6, 76.3, 70.5, 60.2, 29.4, 29.2, 22.5, 22.4; MS (+CI) m/z (relative intensity) 359 (M+H⁺, 36), 269 (100); HRMS (+EI) calcd for $C_{24}H_{22}O_3$ (M⁺) 358.1569, found 358.1591.

EXAMPLE 51

3-[1'-(2''-(((tert-Butyldimethyl)silyloxy)methyl)phenyl)-1'-(methoxyacetoxy)methyl]cyclodeca-3-en-1,5-diyne (Compound 45)

45

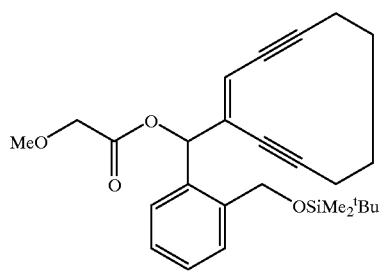

To a solution of Compound 34b (25.2 mg, 5.58×10⁻² mmol) in CHCl₃ (2 mL) was added Eu(fod)₃ (5.8 mg, 5.58×10⁻³ mmol) followed by stirring at room temperature for 40 hours. The reaction mixture was then concentrated under reduced pressure and the residue was purified by flash column chromatography (silica gel, 20 percent EtOAc in hexane) to give 15.7 mg (62 percent) of Compound 45: pale yellow oil; R$_f$=0.45 (20 percent EtOAc in hexane); IR (neat) $^1$H NMR (300 MHz, CDCl₃) δ7.49–7.44 (m, 2H), 7.35–7.28 (m, 2H), 6.62 (s, 1H), 5.72 (s, 1H), 4.86 (s, 2H), 4.14 and 4.04 (AB q, J=16.44 Hz, 2H), 3.43 (s, 3H), 2.45–2.30 (m, 4H), 1.96–1.85 (m, 4H), 0.93 (s, 9H), 0.12 (s, 3H), 0.11 (s, 3H); $^{13}$C NMR (75 MHz, CDCl₃) δ169.0, 138.8, 136.8, 134.5, 128.5, 127.4, 127.3, 127.0, 120.3, 105.4, 103.8, 82.5, 81.1, 71.6, 69.8, 62.6, 59.4, 28.8, 28.5, 26.0, 21.7, 21.7, 18.4, −5.3, −5.3; MS (+CI) m/z (relative intensity) 453 (M+H⁺, 6), 365 (100).

EXAMPLE 52

3-[(1'-(Benzyloxy)acetoxy-1'-(1''-naphthyl))methyl]cyclodeca-3-en-1,5-diyne (Compound 46)

46

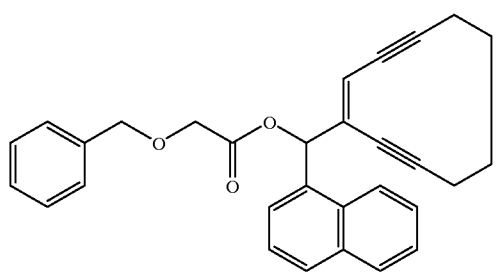

To a solution of Compound 38 (13.5 mg, 3.11×10⁻² mmol) in CHCl₃ (1 mL) was added Eu(fod)₃ (3.2 mg, 3.11×10⁻³ mmol) followed by stirring at room temperature for 24 hours. The reaction mixture was then concentrated under reduced pressure and the residue was purified by flash column chromatography (silica gel, 20 percent EtOAc in hexane) to give 8.1 mg (60 percent) of Compound 46: pale yellow oil; R$_f$=0.52 (20 percent EtOAc in hexane); IR (film) 2934, 2195, 1732, 1120 cm⁻¹; $^1$H NMR (300 MHz, CDCl₃) δ8.06 (d, J=8.00 Hz, 1 H), 7.88–7.84 (m, 2H), 7.67 (d, J=6.40 Hz, 1H), 7.55–7.46 (m, 3H), 7.38–7.27 (m, 5H), 7.17 (s, 1H), 5.78 (s, 1H), 4.65 and 4.61 (AB q, J=11.60 Hz, 2H), 4.26 and 4.17 (AB q, J=16.80 Hz, 2H), 2.40–2.30 (m, 4H), 1.95–1.85 (m, 4H); $^{13}$C NMR (75 MHz, CDCl₃) δ169.1, 136.9, 136.8, 133.6, 130.5, 129.3, 128.7, 128.3 (×2), 128.0, 127.9, 126.5, 125.9, 125.7, 125.1, 123.4, 120.5, 105.6, 104.0, 100.5, 81.2, 73.3, 72.6, 67.2, 28.8, 28.6, 21.8, 21.8; MS (+CI) m/z (relative intensity) 435 (M+H⁺, 1), 270 (100).

EXAMPLE 53

3-[(1'-((4'Methoxybenzyl)oxy)acetoxy-1'-(1''-naphthyl))methyl]cyclodeca-3-en-1,5-diyne (Compound 47)

47

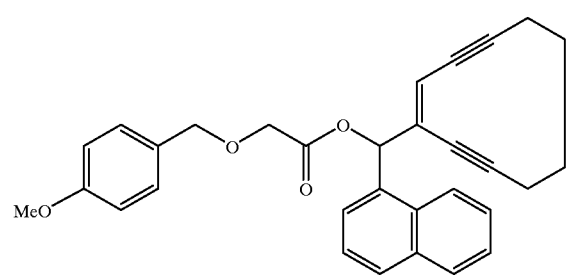

To a solution of Compound 39 (16.3 mg, 3.51×10⁻² mmol) in CHCl₃ (1 mL) was added Eu(fod)₃ (3.6 mg, 3.51×10⁻³ mmol) followed by stirring at room temperature for 24 hours. The reaction mixture was then concentrated under reduced pressure and the residue was purified by flash column chromatography (silica gel, 14 percent EtOAc in hexane) to give 9.4 mg (58 percent) of Compound 47: pale yellow oil; R$_f$=0.44 (14 percent EtOAc in hexane); IR (film) 2934, 2195, 1758, 1612, 1513, 1250, 1182, 1116, 1034 cm⁻¹; $^1$H NMR (300 MHz, CDCl₃) δ8.07 (d, J=8.00 Hz, 1H), 7.88–7.84 (m, 2H), 7.66 (d, J=6.80 Hz, 1H), 7.55–7.46 (m, 3H), 7.27–7.25 (m, 2H), 7.17 (s, 1H), 6.90–6.85 (AA'BB', 2H), 5.79 (s, 1H), 4.58 and 4.54 (AB q, J=11.60 Hz, 2H), 4.4.22 and 4.13 (AB q, J=16.80 Hz, 2H), 3.80 (s, 3H), 2.40–2.30 (m, 4H), 1.95–1.85 (m, 4H); $^{13}$C NMR (75 MHz, CDCl₃) δ169.2, 159.3, 136.8, 133.6, 132.6, 130.5, 129.7, 129.3, 129.0, 128.7, 126.5, 125.9, 125.7, 125.1, 123.4, 120.5, 113.8, 105.6, 104.0, 82.5, 81.2, 72.9, 72.6, 66.8, 55.3, 28.8, 28.6, 21.8, 21.8; MS (+CI) m/z (relative intensity) 465 (M+H⁺, 13).

EXAMPLE 54

3-[1'-(2''-Hydroxymethyl)phenyl]-1'-(methoxyacetoxy)methyl]cyclodeca-3-en-1,5-diyne (Compound 48)

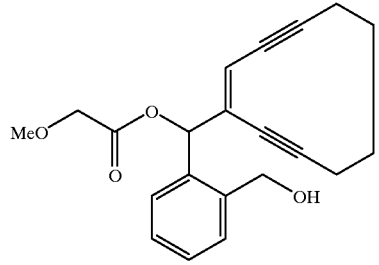

To a solution of Compound 45 (9.1 mg, 2.01×10⁻² mmol) in methanol (1 mL) was added PPTS (1.0 mg, 4.03×10⁻³ mmol) followed by stirring at room temperature for 22 hours. The reaction mixture was then concentrated under reduced pressure, the residue was purified by flash column chromatography (silica gel, 25 percent EtOAc in hexane) to give 4.9 mg (72 percent) of Compound 48: colorless oil; $R_f$=0.17 (25 percent EtOAc in hexane); $^1$H NMR (400 MHz, CDCl$_3$) δ7.49–7.46 (m, 1H), 7.41–7.38 (m, 1H), 7.36–7.32 (m, 2H), 6.66 (s, 1 H), 5.81 (s, 1H), 4.83 and 4.76 (AB q, J=12.40 Hz, 2H), 4.13 and 4.06 (AB q, J=16.40 Hz, 2H), 3.43 (s, 3H), 2.41–2.33 (m, 4H), 1.96–1.86 (m, 5H); $^{13}$C NMR (100 MHz, CDCl$_3$) δ169.2, 138.3, 136.6, 135.5, 129.6, 128.9, 128.3, 127.9, 119.9, 105.9, 104.0, 82.4, 77.2, 72.7, 69.9, 63.1, 59.5, 28.8, 28.6, 21.8, 21.8; MS (+CI) m/z (relative intensity) 338 (M⁺, 2), 249 (100).

EXAMPLE 55

3-[2',5'-Dihydrobenzofuran-2'-yl]cyclodeca-3-en-1,5-diyne (Compound 51)

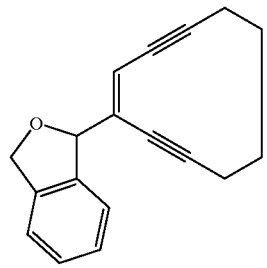

Method A

To a solution of Compound 34a (29.0 mg, 9.42×10⁻² mmol) in CHCl$_3$ (5 mL) was added Eu(fod)$_3$ (9.8 mg, 9.42×10⁻³ mmol) followed by stirring at room temperature for 72 hours. The reaction mixture was then concentrated under reduced pressure and the residue was purified by flash column chromatography (silica gel, 20 percent EtOAc in hexane) to give 21.0 mg (91 percent) of Compound 51.

EXAMPLE 56

4-((tert-Butyldimethylsilyl)oxy)benzaldehyde (Compound 64)

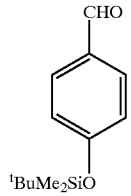

To a solution of 4-hydroxybenzaldehyde, Compound 63 (10.00 g, 81.89 mmol) and imidazole (16.72 g, 245.59 mmol) in dry DMF (30 mL) cooled in an ice-water bath (0° C.) was added a solution of t-butyldimethylsilyl chloride (18.55 g, 123.07 mmol) in dry DMF (50 mL) followed by stirring at room temperature for 1 hour. The reaction mixture was then quenched with brine (60 mL) and extracted with Et2O (60 mL×3). The combined organic layer was dried over anhydrous MgSO$_4$, filtered, and concentrated under reduced pressure. The residue was purified by flash column chromatography (silica gel, 5 percent EtOAc in hexane) to give Compound 64 (19.02 g, 98 percent): pale yellow oil; $R_f$=0.44 (10 percent EtOAc in hexane); IR (neat) 2956, 2931, 1698, 1598, 1273, 1156 cm⁻¹; $^1$H NMR (300 MHz, CDCl$_3$) δ9.89 (s, 1H), 7.81–7.77 (AA'BB', 2H), 6.96–6.92 (AA'BB', 2H), 0.98 (s, 9H), 0.25 (s, 6H); $^{13}$C NMR (75 MHz, CDCl$_3$) δ190.9, 161.5, 131.9, 130.4, 120.5, 25.5, 18.2, −4.4; MS (+CI) m/z (relative intensity) 237 (M+H⁺, 100).

EXAMPLE 57

Methyl (E)-4-((tert-Butyldimethylsilyl)oxy)cinnamate (Compound 65)

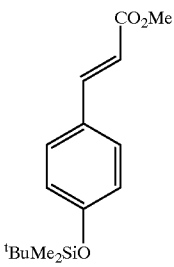

To a solution of trimethyl phosphonate, Compound 13 (14 mL, 86.49 mmol) in dry THF (150 mL) cooled in a dry ice-acetone bath (−78° C.) was added nBuLi (2.5 M in hexanes, 33 mL, 82.50 mmol) followed by stirring at the same temperature for 30 minutes. To the resultant mixture was then added a solution of Compound 64 (19.02 g, 80.45 mmol) in dry THF (80 mL) at −78° C. The resultant mixture was then warmed to room temperature and stirred for 20 hours at room temperature. The reaction mixture was then quenched with saturated aqueous NH$_4$Cl (100 mL) and extracted with EtOAc (100 mL×3). The combined organic layer was washed with brine, dried over anhydrous MgSO$_4$, filtered, and concentrated under reduced pressure. The residue was purified by flash column chromatography (silica gel, 5 percent EtOAc in hexane) to give Compound 65

(19.03 g, 81 percent): white powder; $R_f$=0.44 (10 percent EtOAc in hexane); IR (nujol) 2923, 1724, 1602, 1260, 1166 cm$^{-1}$; $^1$H NMR (300 MHz, CDCl$_3$) δ7.64 (d, J=15.96 Hz, 1H), 7.43–7.40 (AA'BB', 2H), 6.85–6.82 (AA'BB', 2H), 6.30 (d, J=15.93 Hz, 1H), 3.79 (s, 3H), 0.98 (s, 9H), 0.22 (s, 6H); $^{13}$C NMR (75 MHz, CDCl$_3$) δ167.7, 157.8, 144.5, 129.6, 127.6, 120.5, 115.4, 51.5, 25.6, 18.2, –4.4; MS (+CI) m/z (relative intensity) 293 (M+H$^+$, 100).

EXAMPLE 58

Methyl (E)- and (Z)-α-Bromo-4-((tert-butyldimethylsilyl)oxy)cinnamate (Compound 66)

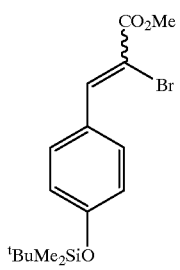

To a solution of Compound 65 (19.03 g, 65.07 mmol) in dry CH$_2$Cl$_2$ (300 mL) was added bromine (3.7 mL, 71.57 mmol) in dry CH$_2$Cl$_2$ (20 mL) through a dropping funnel followed by stirring at room temperature for 1 hour. Triethylamine (14 mL, 100.44 mmol) was added and the resultant mixture was stirred for 15 hours at room temperature. The reaction mixture was quenched with saturated NH$_4$Cl (100 mL) and extracted with CH$_2$Cl$_2$ (100 mL×3). The combined organic layer was washed with Na$_2$S$_{2l}$ $_{O3}$ (100 mL) and brine, dried over anhydrous MgSO$_4$, filtered, and concentrated under reduced pressure. The residue was purified by flash column chromatography (silica gel, 3 percent Et$_2$O-hexane) to give Compound 66 as a mixture of isomers (E:Z=72:28, 22.82 g, 94 percent).

Compound (E)-66 (major): yellow oil; $R_f$=0.42 (5 percent Et$_2$O in hexane); IR (neat) 2954, 2931, 1732, 1603, 1509, 1270, 1219, 1173 cm$^{-1}$; $^1$H NMR (400 MHz, CDCl$_3$) δ7.30 (s, 1H), 7.22–7.19 (AA'BB', 2H), 6.80–6.77 (AA'BB', 2H), 3.77 (s, 3H), 0.97 (s, 9H), 0.20 (s, 6H); $^{13}$C NMR (100 MHz, CDCl$_3$) δ164.9, 156.5, 140.1, 130.0, 127.6, 119.9, 108.6, 53.0, 25.7, 18.3, 4.2; MS (+CI) m/z (relative intensity) 373 (M$^+$, $^{81}$Br, 100), 371 (M$^+$, $^{79}$Br, 94).

Compound (Z)-66 (minor): white solid; $R_f$=0.28 (5 percent Et$_2$O in hexane); $^1$H NMR (400 MHz, CDCl$_3$) δ8.17 (s, 1H), 7.86–7.83 (AA'BB', 2H), 6.89–6.87 (AA'BB', 2H), 3.89 (s, 3H), 0.99 (s, 9H), 0.23 (s, 6H); $^{13}$C NMR (100 MHz, CDCl$_3$) δ164.0, 157.7, 140.5, 132.4, 126.5, 119.9, 109.6, 53.5, 25.7, 18.3, 4.2; MS (+CI) m/z (relative intensity) 373 (M$^+$, $^{81}$Br, 100), 371 (M$^+$, $^{79}$Br, 94).

EXAMPLE 59

Methyl (E)- and (Z-2-[(4'-((tert-Butyldimethylsilyl)oxy)phenyl)methylidene]deca-3,9-diynoate (Compound 67)

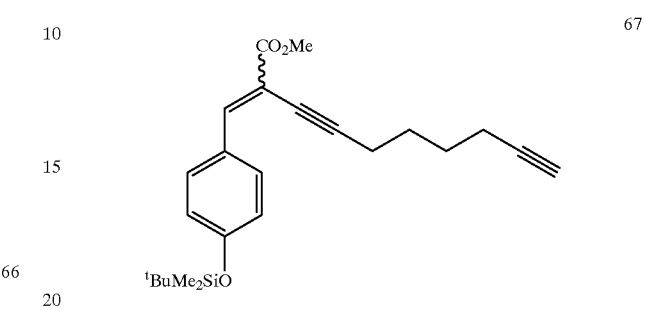

To a suspension of Pd(PPh$_3$)$_4$ (3.32 g, 2.87 mmol) and CuI (1.09 g, 5.72 mmol) in degassed acetonitrile (200 mL) cooled in an ice-water bath (0° C.) was added a solution of Compound 66 (E:Z=72:28, 10.67 g, 28.73 mmol), 1,7-octadiyne (9.5 mL, 71.58 mmol), and ethylpiperidine (30 mL) in degassed acetonitrile (100 mL) via a syringe. The reaction flask was covered against light by a sheet of aluminum foil, and the mixture was stirred at room temperature for 2 hours. The reaction was quenched with saturated aqueous NH$_4$Cl (100 mL), washed with successive portions of saturated aqueous NH$_4$Cl (100 mL×2) and extracted with EtOAc (100 mL×2). The combined organic layer was washed with brine, dried over anhydrous MgSO$_4$, filtered, and concentrated under reduced pressure. The residue was purified by flash column chromatography (silica gel, 3 percent EtOAc in hexane) to give Compound 67 as a mixture of isomers (E:Z=28:72, 8.45 g, 74 percent).

Compound (Z)-67 (major): yellow oil; $R_f$=0.28 (5 percent EtOAc in hexane); IR (neat) 3297, 2951, 2220, 2216, 1724, 1601, 1508, 1259, 1172cm$^{-1}$; $^1$H NMR(300 MHz, CDCl$_3$) δ7.29–7.22 (AA'BB', 2H), 7.04 (s, 1H), 6.80–6.74 (AA'BB', 2H), 3.76 (s, 3H), 2.42 (t, J=6.57 Hz, 2H), 2.26 (td, J=6.84, 2.58 Hz, 2H), 1.96 (t, J=2.61, 1H), 1.75–1.63 (m, 4H), 0.97 (s, 9H), 0.20 (s, 6H); $^{13}$C NMR (100 1Hz, CDCl$_3$) δ166.6, 156.5, 142.8, 130.5, 127.7, 119.8, 114.1, 91.6, 84.1, 78.9, 68.5, 52.3, 27.6, 27.6, 25.7, 19.2, 18.3, 18.1, –4.2; MS (+CI) m/z (relative intensity) 397 (M+H$^+$, 100).

Compound (E)-67 (minor): yellow oil; $R_f$=0.22 (5 percent EtOAc in hexane); $^1$H NMR (300 MHz, CDCl$_3$) δ7.98–7.93 (AA'BB', 2H), 7.79 (s, 1H), 6.88–6.83 (AA'BB', 2H), 3.84 (s, 3H), 2.57 (t, J=6.60 Hz, 2H), 2.27 (td, J=6.78, 2.61 Hz, 2H), 1.96 (t, J=2.61, 1H), 1.81–1.72 (m, 4H), 0.99 (s, 9H), 0.23 (s, 6H); $^{13}$C NMR (100 MHz, CDCl$_3$) δ144.3, 132.0, 127.8, 119.9, 119.8, 110.5, 98.8, 84.0, 68.6, 52.7, 27.7, 27.5, 25.7, 19.7, 18.3, 18.1, 4.2; MS (+CI) m/z (relative intensity) 397 (+H+, 100).

EXAMPLE 60

(E)- and (Z)-2-[(4'-((tert-Butdimethylsilyl)oxy)phenyl)methylidene]deca-3,9-diyn-1-ol (Compound 68)

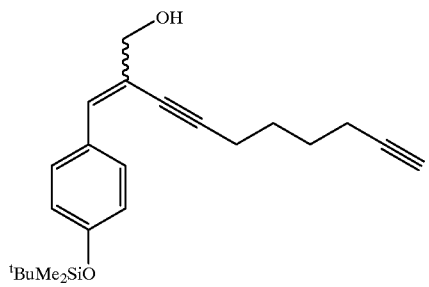

To a solution of Compound 67 (E:Z=28:72, 8.45 g, 21.31 mmol) in dry $CH_2Cl_2$ (50 mL) cooled in a dry ice-acetone bath (−78° C.) was added DIBAL (1 M in $CH_2Cl_2$, 42 mL, 42.00 mmol) followed by stirring at −78° C. for 1 hour. The reaction mixture was then quenched with MeOH (20 mL) at −78° C. and stirred for 30 minutes. Ten percent aqueous HCl (40 mL) was added, and the mixture was stirred at room temperature for another 30 minutes. The resultant mixture was extracted with $CH_2Cl_2$ (50 mL×3). The combined organic layer was washed with brine, dried over anhydrous $MgSO_4$, filtered, and concentrated under reduced pressure. The residue was purified by flash column chromatography (silica gel, 10 percent EtOAc in hexane) to give Compound 68 as a mixture of isomers (E:Z=28:72, 5.47 g, 70 percent).

Compound (Z)-68 (major): yellow oil; $R_f$=0.17 (10 percent EtOAc in hexane); IR (neat) 3400(br), 3307, 2931, 1603, 1508, 1266 $cm^{-1}$; $^1H$ NMR(400MHz,CDCl$_3$) $\delta$7.13–7.10 (AA'BB', 2H), 6.84 (s, 1H), 6.82–6.79 (AA'BB', 2H), 4.33 (s, 2H), 2.43 (t, J=6.39 Hz, 2 H), 2.25 (td, J=6.82, 2.56 Hz, 2H), 1.97 (t, J=2.79 Hz, 1H), 1.77–1.62 (m, 4H), 0.98 (s, 9 H), 0.20 (s, 6H); $^{13}C$ NMR (100 MHz, CDCl$_3$) $\delta$155.3, 136.3, 130.2, 128.9, 122.6, 119.9, 91.4, 84.1, 81.0, 68.6, 61.2, 27.8, 27.7, 25.7, 19.2, 18.3, 18.1, −4.2; MS (+CI) m/z (relative intensity) 369 (M+H$^+$, 36), 351 (M$^+$−OH, 100).

Compound (E)-68 (minor): yellow oil; $R_f$=0.06 (10 percent EtOAc in hexane); $^1H$ NMR (300 MHz, CDCl$_3$) $\delta$7.76–7.71 (AA'BB', 2H), 6.83–6.78 (AA'BB', 2H), 6.63 (s, 1H), 4.23 (s, 2H), 2.51 (t, J=6.57 Hz, 2H), 2.26 (td, J=6.81, 2.67 Hz, 2H), 1.97 (t, J=2.61, 1H), 1.81–1.66 (m, 4H), 0.98 (s, 9H), 0.21 (s, 6H); $^{13}C$ NMR (75 MHz, CDCl$_3$) $\delta$155.7, 132.8, 129.8, 129.4, 119.8, 119.4, 97.8, 84.0, 78.9, 68.6, 67.9, 27.6, 27.5, 25.6, 19.4, 18.2, 18.0, −4.4; MS (+CI) m/z (relative intensity) 369 (M+H$^+$, 36), 351 (M$^+$−OH, 100).

EXAMPLE 61

(E)- and (Z)-2-[(4'-((tert-Butyldimethylsilyl)oxy)phenyl)methylidene]-10-Iododeca-3,9-diyn-1-ol (Compound 69)

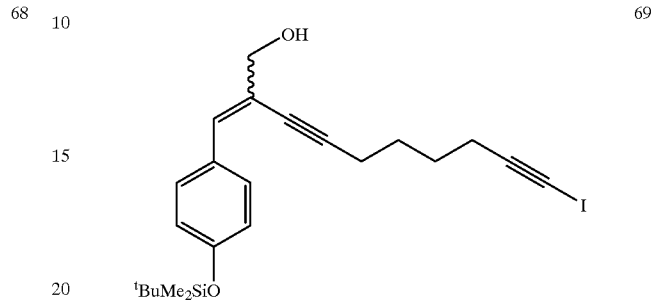

To a solution of iodine (11.46 g, 45.15 mmol) in toluene (100 mL) was added morpholine (10.5 mL, 120.40 mmol) followed by stirring at room temperature for 15 minutes. To the resultant mixture was added Compound 68 (E:Z=28:72, 5.47 g, 14.83 mmol) in toluene (25 mL) followed by heating at 60° C. for 14 hours. The reaction mixture was then allowed to cool down to room temperature, and purified, without aqueous workup, by flash column chromatography directly (silica gel, 100 percent hexane and then 10 percent EtOAc in hexane) to give Compound 69 as a mixture of isomers (E:Z=28:72, 5.59 g, 76 percent).

Compound (Z)-69 (major): yellow oil; $R_f$=0.14 (10 percent EtOAc in hexane); IR (neat) 3401, 2930, 1602, 1506, 1265 $cm^{-1}$; $^1H$ NMR (300 MHz, CDCl$_3$) $\delta$7.14–7.10 (AA'BB', 2H), 6.86 (s, 1H), 6.84–6.77 (AA'BB', 2H), 4.33 (d, J=5.37 Hz, 2H), 2.45–2.35 (m, 4H), 1.89 (t, J=5.97 Hz, 1H), 1.77–1.62 (m, 4H), 0.98 (s, 9H), 0.20 (s, 6H); $^{13}C$ NMR (100 MHz, CDCl$_3$) $\delta$155.5, 136.5, 130.3, 129.0, 122.7, 120.0, 94.2, 91.3, 81.1, 61.2 (×2), 27.7, 27.6, 25.6, 20.4, 19.1, 18.2, −4.4; MS (+CI) m/z (relative intensity) 495 (M+H$^+$, 24), 477 (M$^+$−OH, 77), 351 (M$^+$+HI, 100).

Compound (E)-69 (minor): yellow oil; $R_f$=0.06 (10% EtOAc-hexane); $^1H$ NMR (300 MHz, CDCl$_3$) $\delta$7.77–7.70 (AA'BB', 2H), 6.83–6.78 (AA'BB', 2H), 6.63 (s, 1H), 4.23 (s, 2 H), 2.51 (td, J=6.57, 2.55 Hz, 2H), 2.43 (t, J=6.75 Hz, 1H), 2.26 (td, J=6.75 Hz, 1H), 1.97 (t, J=2.61 Hz, 1H), 1.81–1.60 (m, 4H), 0.99 (s, 9H), 0.21 (s, 6H); $^{13}C$ NMR (100 MHz, CDCl$_3$) $\delta$155.5, 132.7, 129.7, 129.3, 119.7, 119.3, 97.7, 94.0, 78.9, 68.7, 67.9, 27.7, 27.6, 25.8, 20.5, 19.5, 18.3, −4.2; MS (+CI) m/z (relative intensity) 495 (M+H$^+$, 24), 477 (M$^+$−OH, 77), 351 (M$^+$+HI, 100).

EXAMPLE 62

(E)-2-[(4'-((tert-Butyldimethylsilyl)oxy)phenyl)methylidene]-10-Iododeca-3,9-diynal (Compound 70)

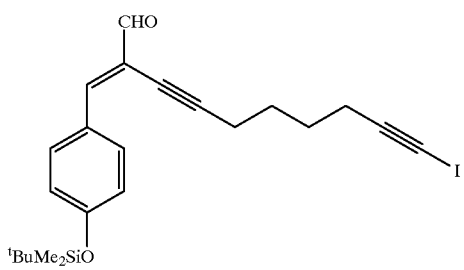

To a suspension of Compound 69 (E:Z=28:72, 5.59 g, 11.31 mmol) and powdered 4A molecular sieves in dry $CH_2Cl_2$ (100 mL) cooled in an ice-water bath (0° C.) was added PCC (4.88 g, 22.64 mmol) followed by stirring at room temperature for 2 hours. The reaction mixture was diluted with $Et_2O$ (20 mL), filtered through a short silica gel pad with rinsing by $Et_2O$. The filtrate was concentrated under reduced pressure and the residue was purified by flash column chromatography (silica gel, 10 percent EtOAc in hexane) to give Compound 70 (3.87 g, 70 percent): pale yellow solid; $R_f$=0.28 (10 percent EtOAc in hexane); IR (nujol) 2924, 2234, 1688, 1594, 1463, 1281 cm$^{-1}$; $^1$H NMR (300 MHz, CDCl$_3$) δ9.50 (s, 1H), 8.04–7.98 (AA'BB', 2H), 7.35 (s, 1H), 6.92–6.87 (AA'BB', 2H), 2.59 (t, J=6.63 Hz, 2H), 2.44 (t, J=6.75 Hz, 2H), 1.83–1.64 (m, 4H), 0.99 (s, 9H), 0.25 (s, 6H); $^{13}$C NMR (75 MHz), CDCl$_3$) δ191.9, 158.9, 151.3, 132.4, 127.7, 121.1, 120.3, 102.0, 94.0, 74.8, 50.0, 27.6, 27.4, 25.6, 20.4, 19.6, 18.3, −4.3; MS (+CI) m/z (relative intensity) 493 (M+H$^+$, 100).

EXAMPLE 63

(E)-2-[(4'-Hydroxyphenyl)methylidene]-10-Iododeca-3,9-diynal (Compound 71)

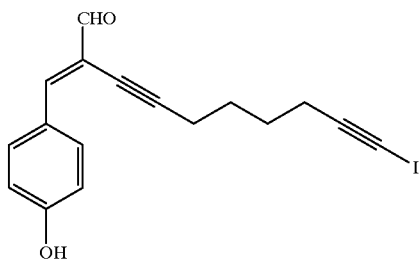

To a solution of Compound 70 (594 mg, 1.21 mmol) in THF (20 mL) cooled in an ice-water bath (0° C.) was added TBAF (1 M in THF, 2.42 mL, 2.42 mmol) followed by stirring at the same temperature for 10 minutes. The reaction was quenched by saturated aqueous NH$_4$Cl (20 mL×2) and extracted with EtOAc (20 mL×2). The combined organic layer was washed with brine, dried over anhydrous MgSO$_4$, filtered, and concentrated under reduced pressure. The residue was purified by flash column chromatography (silica gel, 30 percent EtOAc in hexane) to give Compound 71 (388 mg, 85 percent): pale yellow solid; $R_f$=0.25 (30 percent EtOAc in hexane); IR (nujol) 2923, 1658, 1591 cm$^{-1}$; $^1$H NMR (400 MHz, CDCl$_3$) δ9.51 (s, 1H), 8.06–8.02 (AA'BB', 2H), 7.36 (s, 1H), 6.94–6.90 (AA'BB', 2H), 5.76 (br s, 1H), 2.59 (t, J=6.80 Hz, 2H), 2.44 (t, J=6.80 Hz, 2H), 1.82–1.67 (m, 4H); $^{13}$C NMR (100 MHz, CDCl$_3$) δ191.9, 158.6, 151.3, 132.6, 127.1, 120.9, 115.7, 101.9, 94.1, 77.2, 74.8, 27.8, 27.5, 20.5, 19.7; MS (+CI) m/z (relative intensity) 379 (M+H$^+$, 32).

EXAMPLE 64

(E)-2-[(4'-((Trimethylacetyl)oxy)phenyl)methylidene]-10-Iododeca-3,9-diynal (Compound 73)

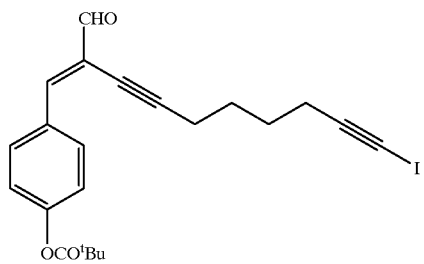

To a solution of Compound 71 (214.9 mg, 0.57 mmol) in dry THF (10 mL) cooled in an ice-water bath (0° C.) was added NaH (60 percent, 29.6 mg, 0.74 mmol) followed by stirring for 15 minutes. A yellow-colored solution of 3-(Trimethylacetyl)-1,3-thiazolidine-2-thione, Compound 72 (116.8 mg, 0.57 mmol) in dry THF (5 mL) was added, and the resultant mixture was stirred for 30 minutes at room temperature. The reaction mixture was quenched by water, extracted with EtOAc (15 mL×3). The combined organic layer was washed with brine, dried over anhydrous MgSO$_4$, filtered, and concentrated under reduced pressure. The residue was purified by flash column chromatography (silica gel, 10 percent EtOAc in hexane) to give Compound 73 (205.3 mg, 78 percent): pale yellow solid; $R_f$=0.39 (20 percent EtOAc in hexane); IR (nujol) 2973, 2223, 2117, 1755, 1694, 1599, 1133 cm$^{-1}$; $^1$H NMR (300 MHz, CDCl$_3$) δ9.54 (s, 1H), 8.13–8.09 (AA'BB', 2H), 7.40 (s, 1H), 7.19–7.15 (AA'BB', 2H), 2.58 (t, J=6.66 Hz, 2H), 2.44 (t, J=6.60 Hz, 2H), 1.80–1.67 (m, 4H); $^{13}$C NMR (100 MHz, CDCl$_3$) δ191.0, 176.1, 152.8, 149.5, 131.2, 122.7, 121.5, 121.5, 102.4, 93.7, 76.9, 74.3, 39.0, 27.4, 27.1, 26.9, 20.2, 19.4; MS (+CI) m/z (relative intensity) 463 (M+H$^+$, 86), 251 (100).

EXAMPLE 65

(E)4-[(4'-((Trimethylacetyl)oxy)phenyl)methylidene]cyclodeca-1,5-diyn-3-ol (Compound 74a)

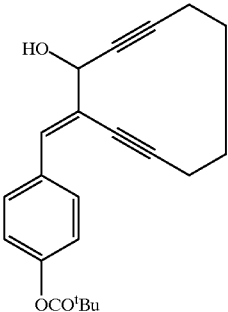

74a

Prepared in 30 percent yield from Compound 73 by the procedure described for Compound 20a. Compound 74a: white solid; $R_f$=0.17 (14 percent EtOAc in hexane); IR (nujol) 3413 (br), 2934, 2210, 1752, 1118 cm$^{-1}$; $^1$H NMR (300 MHz, CDCl$_3$) δ7.90–7.87 (AA'BB', 2H), 7.05–7.01 (AA'BB', 2H), 6.69 (s, 1H), 4.94 (s, 1H), 2.50–2.43 (m, 2H), 2.43–2.32 (br s, 1H), 2.28–2.21 (m, 2H), 1.90–1.75 (m, 4H), 1.35 (s, 9H); $^{13}$C NMR (100 MHz, CDCl$_3$) δ177.6, 151.5, 134.1, 132.4, 130.2, 125.3, 121.9, 104.7, 92.2, 82.6, 81.1, 68.8, 39.7, 28.3, 28.2, 27.8, 22.5, 21.2; MS (+CI) m/z (relative intensity) 337 (M+H$^+$, 52), 319 (100).

EXAMPLE 66

(E)-3-Acetoxy-4-[(4'-((trimethylacetyl)oxy)phenyl)methylidene]cyclodeca-1,5-diyne (Compound 75a)

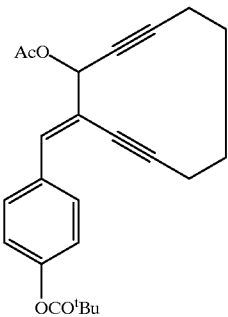

75a

Prepared in 72 percent yield from Compound 74 by the procedure described for Compound 30a. Compound 75: white solid; $R_f$=0.48 (17 percent EtOAc in hexane); IR (nujol) 2934, 2234, 2213, 1756, 1728, 1275 cm$^{-1}$; $^1$H NMR (300 MHz, CDCl$_3$) δ7.92–7.89 (AA'BB', 2H), 7.05–7.02 (AA'BB', 2H), 6.67 (s, 1H), 6.03 (s, 1H), 2.60–2.23 (m, 4H), 2.12 (s, 3H), 1.96–1.68 (m, 4H), 1.35 (s, 9H); $^{13}$C NMR (100 MHz, CDCl$_3$) δ177.6, 170.9, 151.8, 135.1, 133.7, 130.5, 122.0, 121.2, 104.7, 93.7, 81.0, 79.3, 69.8, 39.8, 28.2, 28.1, 27.8, 22.5, 22.0, 21.4; MS (+CI) m/z (relative intensity) 378 (M+H$^+$, 6), 319 (100).

EXAMPLE 67

(E)-2-[(4'-((((4"-Methoxybenzyl)oxy)carbonyl)methoxy)phenyl)methylidene]-10-Iododeca-3,9-diynal (Compound 77b)

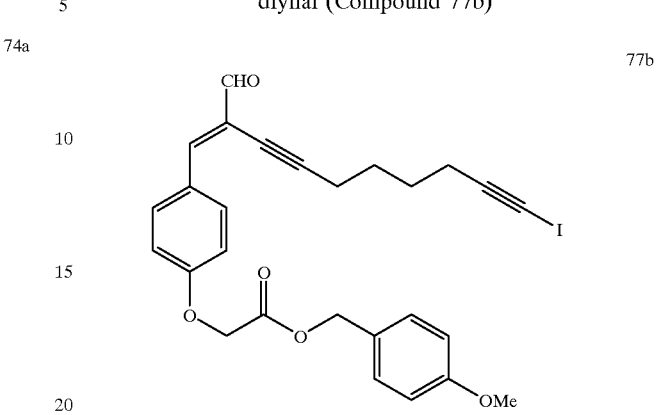

77b $R_f$=0.21 (20 percent EtOAc in hexane); IR (nujol) 2937, 2232, 1755, 1684, 1594, 1509, 1173 cm$^-$; $^1$H NMR (300 MHz, CDCl$_3$) δ9.50 (s, 1H), 8.07–8.02 (AA'BB', 2H), 7.34 (s, 1H), 7.30–7.25 (AA'BB', 2H), 6.96–6.84 (m, 4H), 5.18 (s, 2H), 4.70 (s, 2H), 3.80 (s, 3H), 2.56 (t, J=6.66 Hz, 2H), 2.43 (t, J=6.69 Hz, 2H), 1.82–1.66 (m, 4H); $^{13}$C NMR (100 MHz, CDCl$_3$) δ192.4, 168.9, 160.8, 160.5, 151.4, 133.0, 131.1, 128.7, 127.7, 122.2, 115.4, 114.7, 102.8, 94.7, 77.9, 75.5, 67.7, 65.9, 55.9, 28.3, 28.0, 21.0, 20.2; MS (+CI) m/z (relative intensity) 557 (M+H$^+$, 3), 431 (100).

EXAMPLE 68

(E)-4-[(4'-((((4"-Methoxybenzyl)oxy)carbonyl)methoxy)phenyl)methylidene]cyclodeca-1,5-diyn-3-ol (Compound 78b)

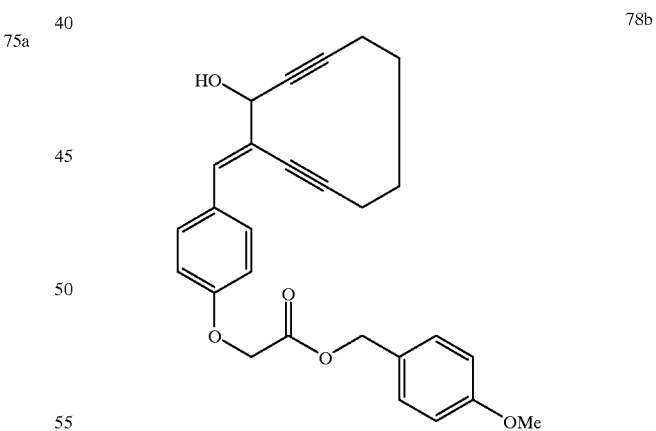

78b

Prepared in 41 percent yield from Compound 77 by the procedure described for Compound 20a. Compound 78: pale yellow oil; $R_f$=0.23 (33 percent EtOAc in hexane); IR (nujol)3481 (br), 2934, 2211, 1755, 1604, 1511, 1249, 1174 cm$^{-1}$; $^1$H NMR(300 MHz, CDCl$_3$) δ7.85–7.80 (AA'BB', 2H), 7.30–7.24 (AA'BB', 2H), 6.91–6.82 (m, 4H), 6.64 (s, 1H), 5.17 (s, 2H), 4.93 (br s, 1H), 4.64 (s, 2H), 3.81 (s, 3H), 2.55–2.45 (m, 2H), 2.40–2.33 (m, 1H), 2.28–2.20 (m, 2H), 1.93–1.68 (m, 4H); $^{13}$C NMR (100 MHz, CDCl$_3$) δ169.4, 160.5, 158.3, 132.8, 131.0, 130.6, 130.4, 127.9, 123.5, 115.1, 114.6, 104.3, 92.1, 82.7, 81.2, 69.0, 67.5, 66.0, 55.9, 28.3, 28.2, 22.6, 21.2; MS (+CI) m/z (relative intensity) 431 (M +H$^+$, 3), 430 (M$^+$, 6), 413 (M$^+$–OH, 7), 120 (100).

Method B

To a solution of Compound 34b (5.2 mg, 1.54×10$^{-2}$ mmol) in CHCl$_3$ (1 mL) was added Eu(fod)$_3$ (1.6 mg, 1.54×10$^{-3}$ mmol) followed by stirring at room temperature for 48 hours. The reaction mixture was then concentrated under reduced pressure and the residue was purified by flash column chromatography (silica gel, 20 percent EtOAc in hexane) to give 3.6 mg (95 percent) of Compound 51: colorless oil; R$_f$=0.55 (20 percent EtOAc in hexane); IR (neat) 2928, 2192, 1032 cm$^{-1}$; $^1$H NMR (300 MHz, CDCl$_3$) δ7.37–7.22 (m, 4H), 5.96 (s, 1H), 5.66 (s, 1 H, 5.26 (dd, J=12.30, 2.82 Hz, 1H), 5.12 (d, J=12.30 Hz, 1H), 2.43–2.30 (m, 4H), 1.96–1.85 (m, 4H); $^{13}$C NMR (75 MHz, CDCl$_3$) δ140.3, 140.2, 139.6, 128.6, 128. 123.0, 121.7, 118.7, 106.0, 103.6, 84.8, 83.4, 81.8, 74.0, 29.5, 29.3, 22.5, 22.4; MS (+CI) m/z (relative intensity) 249 (M$^+$, 2), 87 (100).

EXAMPLE 69

Biological Evaluation

DNA cleavage studies on the compounds of this invention were performed by using supercoiled, covalently closed, circular φX174 RFI (Form I) double stranded DNA. Thus, a 54.3 μM/bp (micromolar per base pair) solution of φX174 RFI DNA and a compound in the indicated concentration in TEA buffer (pH 8.5) containing 20% DMSO was incubated at 37° C. for 48–72 hours and analyzed by 1% agarose gel electrophoresis to separate the various forms of DNA. DNA cleavage was indicated by the formation of nicked relaxed circular DNA (Form II) or linearized DNA (Form III), which was visualized using ethidium bromide stain. A photo picture of the gel was taken over a 365 nanometer ultra-violet light transilluminator and the relative densities of DNA bands were quantitated by a GS-700 imaging densitometer (BIO-RAD). The percentage of net DNA cleavage was calculated by the following equation:

Net DNA Cleavage (%)={[(Form II)$_s$+2×(Form III)$_s$]/[(Form I)$_s$+ (Form II)$_s$+2×(Form III)$_s$]×100}−{(Form II)$_c$/[(Form I)$_c$+(Form II)$_c$]×100} wherein the subscripts "s" and "c" refer to as the samples and controls, respectively.

Cytotoxicity was assessed in P388 mice T cell leukemia cells by MTT [3-(4,5-dimethylthiazol-2-yl)-2,5-diphenyl-2H-tetrazolium bromide] assay. Cell suspension (1×10$^5$ cells/mL) was plated in 96 well microtiter plates at 50 μL/well and it was followed by 50 μL/well of the test compound in serially diluted concentrations. The cells were incubated at 37° C. in a humidified atmosphere containing 5% CO$_2$ in air for 72 hours at which time the tetrazolium dye, MTT, was added. After another 3 hours incubation, 100 μL/well of acidified 2-propanol (0.04 N HCl) was added. The optical densities of the plates were measured with a microplate reader (BIO-RAD) at 570 nm. The greater the absorbance the greater the number of live cells. The results are expressed as an IC$_{50}$ which is the drug concentration required to inhibit cell proliferation to 50% of that of untreated control cells. The detailed procedure is found in Mosman, *J. Immunol. Methods* 65:55 (1983); Ferrari et al., *Immunol. Methods* 131:165 (1990).

DNA cleavage results of the selected compounds of this invention are summarized in FIGS. 1–6. The results in FIG. 1 show that Compound 6 possessing a hydroxyl group is less potent compared to the corresponding acetate, Compound 29, at 100 μM concentration in the pH range of 7.0–8.5. Also, as illustrated in FIG. 1B, Compound 29 exhibits slightly higher DNA cleavage activity in the basic pHs. The negative bars for Compound 6 are due to slight decomposition of Form I DNA in the basic pHs. Therefore, the actual values for Compound 29 in the basic pHs should be higher than the data showed.

Figure 2:
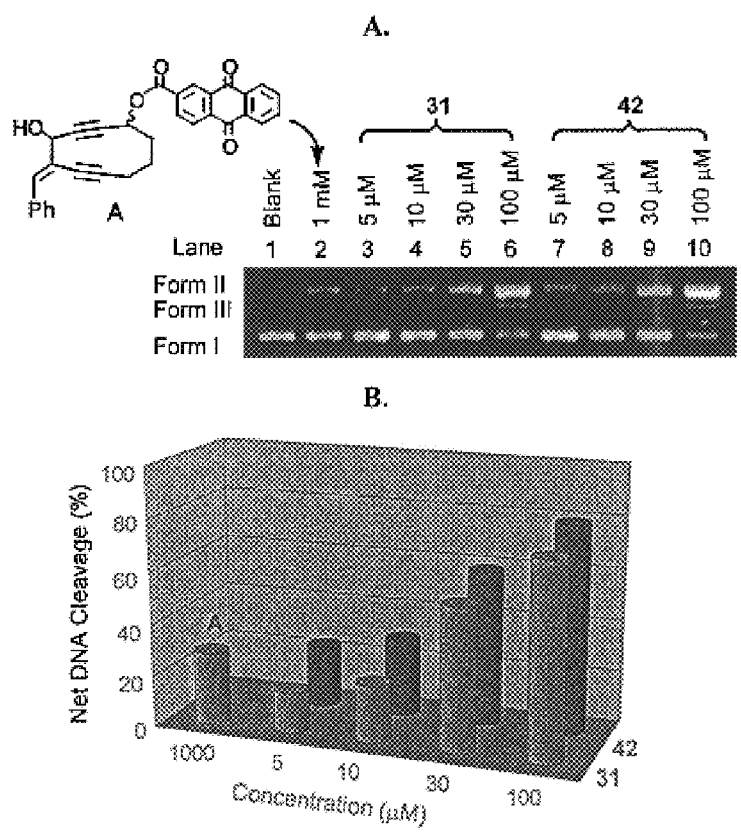
FIG. 2A is a photograph of an ethidium bromide stained 1 percent agarose gel that illustrates the cleavage of φX174 RFI (Form I) DNA by Compounds 31 and 42 at 37° C. after 72 hours in TEA buffer containing 20% DMSO at pH 8.5. Lane 1 is control; Lane 2 shows the result obtained with 1 mM Compound A; Lanes 3–6 show the results obtained with 5, 10, 30, and 100 μM Compound 31, respectively; Lanes 7–10 show the results obtained with 5, 10, 30, and 100 μM Compound 42, respectively.
FIG. 2B is a graph of the scanning densitometry results of the gel picture shown in FIG. 2A.
Figure 3:
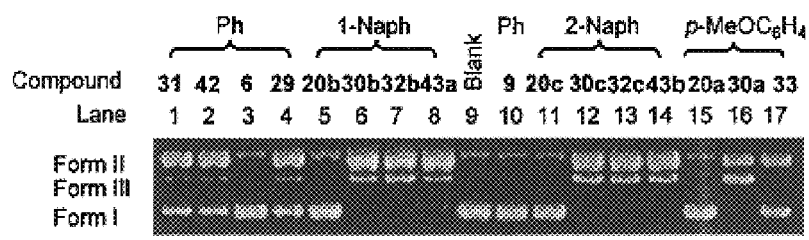
FIG. 3A is a photograph of an ethidium bromide stained 1 percent agarose gel that illustrates the cleavage of φX174 RFI (Form I) DNA by various compounds at 37° C. after 72 hours in TEA buffer containing 20% DMSO at pH 8.5. Lanes 1–8 show the results obtained with 100 μM Compounds 31, 42, 6, 29, 20b, 30b, 32b, and 43, respectively; Lane 9 is control; Lanes 10–17 show the results obtained with 100 μM Compounds 9, 20c, 30c, 32c, 44, 20a, 30a, and 33, respectively.
FIG. 3B is a graph of the scanning densitometry results of the gel picture shown in FIG. 3A.
Figure 3:
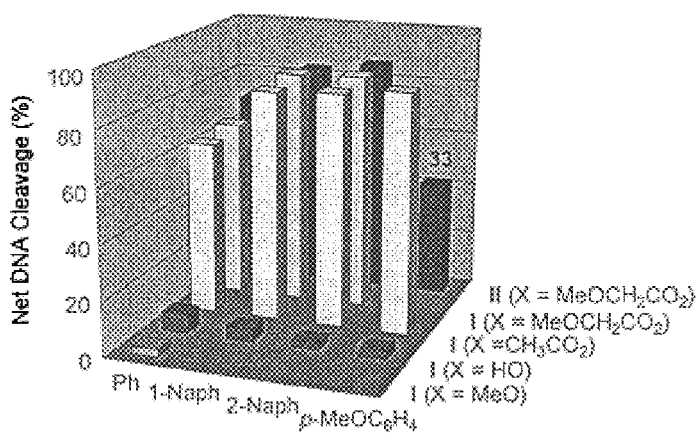

The results in FIG. 2 demonstrate that the methoxyacetates, Compounds 31 and 42 are ca. 100-fold more potent than the alcohol, Compound A, reported by Dai et al., *J. Org. Chem.*, 64:682 (1999). More important is the observation that Compound 31 delivers the same level of DNA cleavage activity as enediyne, Compound 42 within the concentration range of 5–100 μM. This finding strongly supports the notion that (E)-3-acyloxy-4-(arylmethylidene) cyclodeca-1,5-diynes of formula IA, can be used as thermally stable enediyne prodrugs.

The results in FIG. 3 confirm again that a good leaving group X, such as an acyl group, is critically important for high DNA cleavage activity. Compounds of formula IA having X=OH and OMe are weak DNA cleavers whereas Compounds of formula IA or IB having X=acyloxy are remarkably potent. The gel picture in FIG. 3A was obtained at 100 μM concentration. Formation of Form III DNA was clearly observed for those compounds possessing a naphthyl or p-methoxyphenyl ring.

Figure 4:
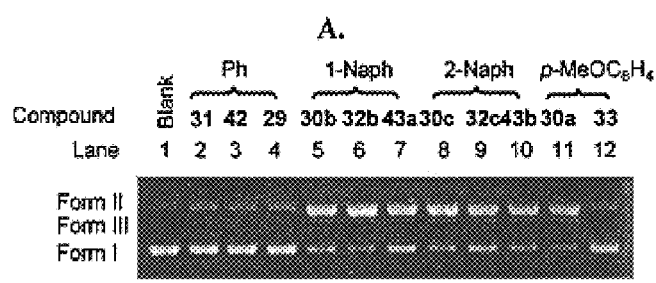
FIG. 4A is a photograph of an ethidium bromide stained 1 percent agarose gel that illustrates the cleavage of φX174 RFI (Form I) DNA by various compounds at 37° C. after 72 hours in TEA buffer containing 20% DMSO at pH 8.5. Lane 1 is control; Lanes 2–12 show the results obtained with 20 μM Compounds 31, 42, 29, 30b, 32b, 43, 30c, 32c, 44, 30a, and 33, respectively.
FIG. 4B is a graph of the scanning densitometry results of the gel picture shown in FIG. 4A.
Figure 4:
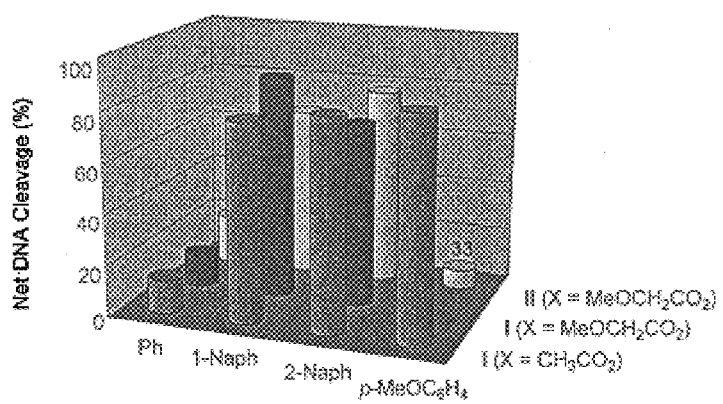

The results of FIG. 4 were obtained at a reduced concentration of 20 μM. Thus, the difference resulting from the aryl group is clearly analyzed. As depicted in FIG. 4B, the phenyl-derived compound of formula IA having X=CH$_3$CO$_2$ is much weaker compared with the 1-naphthyl, 2-naphthyl, and p-methoxyphenyl analogs. This trend in DNA cleavage potency is consistent with the allylic cation stability resulting from loss of the acyloxy group [Dai et al. *J. Org. Chem.*, 64:5062 (1999)]. Compound 33 showed reduced DNA cleavage activity perhaps because it possesses a hydroxyl group in stead of an acyloxy group.

Figure 5:
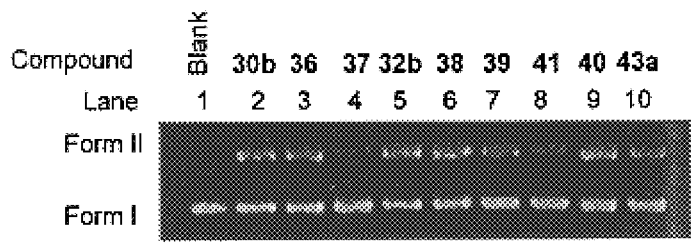
FIG. 5A is a photograph of an ethidium bromide stained 1 percent agarose gel that illustrates the cleavage of φX174 RFI (Form I) DNA by various compounds possessing a 1-naphthyl group at 37° C. after 72 hours in TEA buffer containing 20% DMSO at pH 8.5. Lane 1 is control; Lanes 2–10 show the results obtained with 5 μM Compounds 30b, 36, 37, 32b, 38, 39, 41, 40, and 43, respectively.
FIG. 5B is a graph of the scanning densitometry results of the gel picture shown in FIG. 5A.
Figure 5:
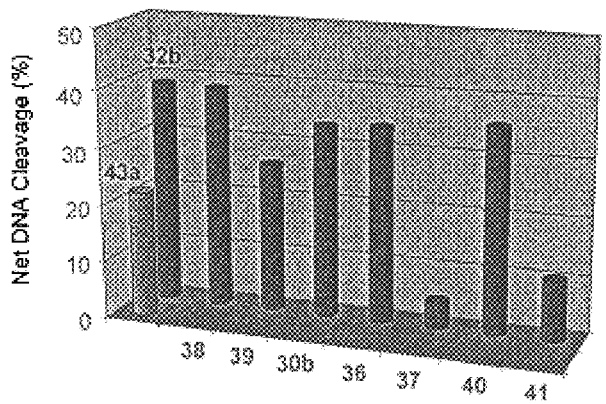

Results in FIG. 5 reveal the effects of the acyloxy group on the potency of the 1-naphthyl-containing enediyne prodrugs. In general, Compounds 32b, 38, and 39 possessing an alkoxyacetyloxy moiety exert a similar level of activity. However, a long alkyl chain has a significant effect on the DNA cleaving profile, for example, Compound 37 having a C$_8$ carbon chain delivers ca. one eighth of the activity of Compound 32b. Aromatic acyl groups also contribute to the drug performance. A 1-anthracene ring in Compound 41 reduced the DNA cleaving potency whereas a 2,5-dimethoxybenzene ring in Compound 40 had little effect as compared to the acetate in Compound 30b.

Figure 6:
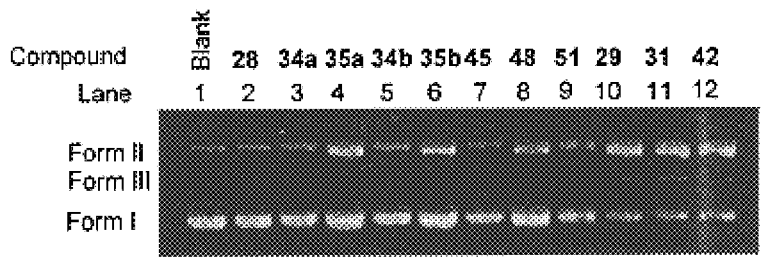
FIG. 6A is a photograph of an ethidium bromide stained 1 percent agarose gel that illustrates the cleavage of φX174 RFI (Form I) DNA by various compounds at 37° C. after 72 hours in TEA buffer containing 20% DMSO at pH 8.5. Lane 1 is control; Lanes 2–12 show the results obtained with 100 μM Compounds 28, 34a, 35a, 34b, 35b, 45, 48, 51, 29, 31, and 42, respectively.
FIG. 6B is a graph of the scanning densitometry results of the gel picture shown in FIG. 6A.
Figure 6:
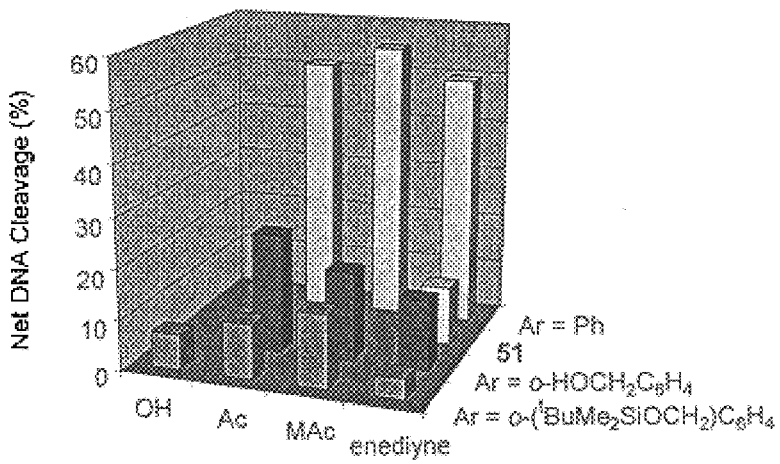

FIG. 6 illustrates a comparison between the ortho-substituted phenyl and the parent phenyl compounds. As shown in FIG. 6B, all ortho-substituted phenyl compounds exhibited a diminished level of potency when compared to Compounds 29, 31, and 42 (Ar=Ph). Compound 51 is also less potent than Compound 42. These results suggest that steric hindrance resulting from the ortho-substituent may be one of the causes.

DNA cleavage and cytotoxicity data of selected compounds are listed in Table 1. In general, trends in both DNA cleaving potency and cytotoxicity are parallel to each other. Among the listed compounds, the acetates possessing a naphthyl group, Compounds 30b,c, are the most cytotoxic enediyne prodrugs, having IC$_{50}$ of 2.4×10$^{-6}$ and 2.8×10$^{-6}$ M, respectively.

TABLE 1

DNA cleavage and cytotoxicity data against P388 mouse leukemia cells of selected compounds.[a]

| compd | Ar | X | net DNA cut (%) | IC$_{50}$ ($\mu$M) |
|---|---|---|---|---|
| 29 | Ph | CH$_3$CO$_2$ | 19.3[b] | 48 |
| 31 | Ph | CH$_3$OCH$_2$CO$_2$ | 13.2[b] | 23 |
| 30a | p-MeOC$_6$H$_4$ | CH$_3$CO$_2$ | 86.4[b] | 15 |
| 34a | o-TBSOCH$_2$C$_6$H$_4$ | CH$_3$CO$_2$ | 10.7[c] | >50 |
| 34b | o-TBSOCH$_2$C$_6$H$_4$ | CH$_3$OCH$_2$CO$_2$ | 14.4[c] | >50 |
| 35a | o-HOCH$_2$C$_6$H$_4$ | CH$_3$CO$_2$ | 23.5[c] | 21 |
| 35b | o-HOCH$_2$C$_6$H$_4$ | CH$_3$OCH$_2$CO$_2$ | 17.6[c] | 16 |
| 30b | 1-Naph | CH$_3$CO$_2$ | 77.7[b] 33.5[d] | 2.4 |
| 36 | 1-Naph | CH$_3$CH$_2$CO$_2$ | 34.0[d] | 10 |
| 37 | 1-Naph | CH$_3$(CH$_2$)$_6$CO$_2$ | 4.67[d] | 13 |
| 32b | 1-Naph | CH$_3$OCH$_2$CO$_2$ | 87.4[b] 38.8[d] | 12 |
| 38 | 1-Naph | BnOCH$_2$CO$_2$ | 38.6[d] | 6.7 |
| 39 | 1-Naph | PMBOCH$_2$CO$_2$ | 26.1[d] | 97 |
| 40 | 1-Naph | 2,5-(MeO)$_2$C$_6$H$_4$CO$_2$ | 35.6[d] | 17 |
| 41 | 1-Naph | 1-Anthracene-CO$_2$ | 10.6[d] | 11 |
| 30c | 2-Naph | CH$_3$CO$_2$ | 82.3[b] | 2.8 |
| 32c | 2-Naph | CH$_3$OCH$_2$CO$_2$ | 71.9[b] | 28 |
| 42 | Ph | CH$_3$OCH$_2$CO$_2$ | 12.9[b] | 7.7 |
| 45 | o-TBSOCH$_2$C$_6$H$_4$ | CH$_3$OCH$_2$CO$_2$ | 4.13[c] | 12 |
| 48 | o-HOCH$_2$C$_6$H$_4$ | CH$_3$OCH$_2$CO$_2$ | 13.6[c] | 8.1 |
| 43a | 1-Naph | CH$_3$OCH$_2$CO$_2$ | 67.4[b] | 3.8 |
| 43b | 2-Naph | CH$_3$OCH$_2$CO$_2$ | 77.8[b] | 9.6 |

[a] See text for details of the DNA cleavage assay and definition of the net DNA cut. Cytotoxicity was performed by incubation of P388 mouse leukemia cells with the samples at 37° C. for 72 h in air containing 5% CO$_2$. IC$_{50}$ was calculated for the drug molar concentration at which 50% cells were killed. [b] At 20 $\mu$M. [c] At 100 $\mu$M. [d] At 5 $\mu$M.

What is claimed is:

1. A compound of the general formula

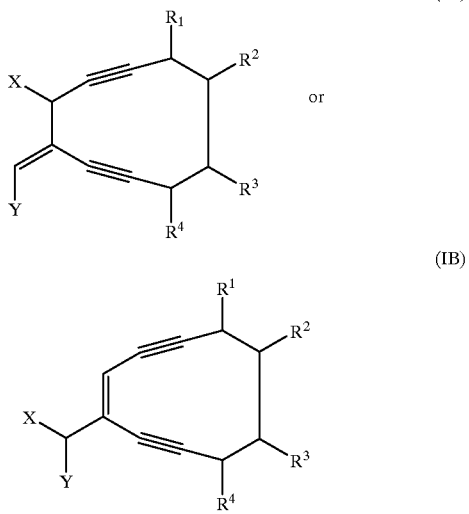

(IA)

or (IB)

wherein
R$^1$, R$^2$, R$^3$ and R$^4$ each independently represent a hydrogen atom or a group —OR, where R represents a hydrogen atom, an optionally substituted alkyl or acyl group or a moiety which is capable of binding to a nucleic acid; and/or,
R$^1$ and R$^2$, R$^2$ and R$^3$ or R$^3$ and R$^4$ together with the interjacent carbon atoms represent an optionally substituted cycloalkyl group;
X represents a hydroxyl group or an optionally substituted alkoxy or acyloxy group; and
Y represents an optionally substituted aryl or heteroaryl group; or,
in the case of formula IB, X and Y together with the interjacent carbon atom represent an optionally substituted heterocyclic group;
or a salt thereof; with the proviso that, when R$^1$ represents an anthraquinone-2-carbonyloxy group, X represents a hydroxyl group or, in the case of formula IB, an ethoxy group and Y represents a phenyl group, then one of R$^2$, R$^3$ and R$^4$ represents a group OR or R$^2$ and R$^3$ or R$^3$ and R$^4$ together with the interjacent carbon atoms represent an optionally substituted cycloalkyl group.

2. A compound according to claim 1 wherein R$^1$, R$^2$, R$^3$ and R$^4$ each independently represent a hydrogen atom or a group —OR, where R represents a hydrogen atom, C$_{1-12}$ alkyl, C$_{1-12}$ alkanoyl, C$_{6-18}$ arylcarbonyl or 5- to 18-membered heteroarylcarbonyl group or a group which is capable of binding to a nucleic acid, each group being optionally substituted by one or more substituents selected from the group consisting of halogen atoms, nitro and hydroxyl groups and groups of formula —R$^5$ or —OR$^5$, where R$^5$ is a C$_{1-12}$ alkyl or C$_{7-16}$ aralkyl group each optionally substituted by one or more substituents selected from the group consisting of halogen atoms, nitro, hydroxyl, C$_{1-6}$ alkyl, C$_{1-6}$ haloalkyl, C$_{1-6}$ alkoxy and C$_{1-6}$ haloalkoxy groups.

3. A compound according to claim 1 wherein R$^1$ and R$^2$, R$^2$ and R$^3$ or R$^3$ and R$^4$ together with the interjacent carbon atoms represent a C$_{5-8}$ cycloalkyl group optionally substituted by one or more substituents selected from the group consisting of halogen atoms, nitro, hydroxyl, C$_{1-6}$ alkyl, C$_{1-6}$ alkoxy, C$_{1-6}$ haloalkoxy and oxy groups.

4. A compound according to claim 1 in which R$^1$, R$^2$, R$^3$ and R$^4$ each represent a hydrogen atom.

5. A compound according to claim 1 wherein X represents a hydroxyl, C$_{1-12}$ alkoxy, C$_{1-12}$ alkanoyloxy, C$_{6-18}$ arylcarbonyloxy or 5- to 18-membered heteroarylcarbonyloxy group, each group being optionally substituted by one or more substituents selected from the group consisting of halogen atoms, nitro and hydroxyl groups and groups of formula —R$^6$ or —OR$^6$, where R$^6$ is a C$_{1-12}$ alkyl or C$_{7-16}$ aralkyl group each optionally substituted by one or more substituents selected from the group consisting of halogen atoms, nitro, hydroxyl, C$_{1-6}$ alkyl, C$_{1-6}$ haloalkyl, C$_{1-6}$ alkoxy and C$_{1-6}$ haloalkoxy groups.

6. A compound according to claim 5 wherein X represents a hydroxyl, C$_{1-8}$ alkoxy, C$_{1-8}$ alkanoyloxy, C$_{6-14}$ arylcarbonyloxy or 5- to 10-membered heteroarylcarbonyloxy group, each group being optionally substituted by one or more substituents selected from the group consisting of halogen atoms and groups of formula —R$^6$ or —OR$^6$, where R$^6$ is a C$_{1-8}$ alkyl or C$_{7-10}$ aralkyl group each optionally substituted by one or more substituents selected from halogen atoms, nitro, C$_{1-4}$ alkoxy and C$_{1-4}$ haloalkoxy groups.

7. A compound according to claim 6 wherein X represents a hydroxyl, methoxy, ethanoyloxy, methoxyethanoyloxy, propanoyloxy, dimethylpropanoyloxy, pentanoyloxy, heptanoyloxy, benzoyloxy, dimethoxybenzoyloxy, naphthylcarbonyloxy, anthracenecarbonyloxy, pyridinecarbonyloxy, benzyloxyethanoyloxy, methoxybenzyloxyethanoyloxy, nitrobenzyloxyethanoyloxy or trifluoroethoxyethanoyloxy group.

8. A compound according to claim 7 wherein X represents a hydroxyl, methoxy, ethanoyloxy, methoxyethanoyloxy, n-propanoyloxy, 2,2-dimethylpropanoyloxy, n-heptanoyloxy, 2,5-dimethoxybenzoyloxy, 1-anthracenecarbonyloxy, benzyloxyethanoyloxy or 4-methoxybenzyloxyethanoyloxy group.

9. A compound according to claim 1 wherein Y represents a $C_{6-18}$ aryl or 5- to 18-membered heteroaryl group, each group being optionally substituted by one or more substituents selected from the group consisting of halogen atoms, nitro and hydroxyl groups and groups of formula —$(Z)_m$—$(CR^7R^8)_n$—$R^9$ where m is 0 or 1, Z is an oxygen or sulfur atom, n is 0 or an integer from 1 to 6, $R^7$ and $R^8$ each independently represent a hydrogen atom or a $C_{1-6}$ alkyl group, and $R^9$ represents a hydroxyl, $C_{1-12}$ alkyl, $C_{1-12}$ haloalkyl, $C_{1-12}$ alkoxy, $C_{1-12}$ haloalkoxy, amino, $C_{1-12}$ alkylamino, di-$C_{1-12}$ alkylamino, carboxyl, $C_{1-12}$ alkanoyl, sulfanyl, $C_{1-12}$ alkylsulfanyl or 5- to 14-membered heterocyclic group or a group —$(W)_p$—$R^{10}$, where p is 0 or 1, W is an oxygen or sulfur atom and $R^{10}$ represents a silyl protecting group, a $C_{1-12}$ alkanoyl or $C_{1-12}$ alkoxycarbonyl group each optionally substituted by a $C_{1-6}$ aryl group which is itself optionally substituted by one or more substituents selected from the group consisting of halogen atoms, nitro, hydroxy, $C_{1-6}$ alkyl, $C_{1-6}$ haloalkyl, $C_{1-6}$ alkoxy and $C_{1-6}$ haloalkoxy groups, or a group of formula —CO—$R^{11}$, —CO—$OR^{12}$ or —CO—$NHR^{13}$ where $R^{11}$, $R^{12}$ and $R^{13}$ each independently represent a moiety which is capable of binding to a nucleic acid.

10. A compound according to claim 9 wherein Y represents a $C_{6-14}$ aryl or 5- to 14-membered heteroaryl group, each group being optionally substituted by one or more substituents selected from the group consisting of groups of formula —$(Z)_m$—$(CR^7R^8)_n$—$R^9$ where m and Z are as defined in claim 6, n is 0 or an integer from 1 to 4, $R^7$ and $R^8$ each independently represent a hydrogen atom or a $C_{1-4}$ alkyl group, and $R^9$ represents a hydroxyl, $C_{1-6}$ alkyl, $C_{1-6}$ alkoxy, amino, $C_{1-6}$, alkylamino, carboxyl, sulfanyl or 5- to 10-membered heterocyclic group or a group —$(W)_p$—$R^{10}$ where p and W are as defined in claim 6 and $R^{10}$ represents a tri-$(C_{1-6}$alkyl)silyl group, a $C_{1-6}$ alkanoyl or $C_{1-6}$ alkoxycarbonyl group optionally substituted by a phenyl group which is itself optionally sustituted by one or more substituents selected from the group consisting of nitro, hydroxy, $C_{1-4}$ alkyl and $C_{1-4}$ alkoxy groups, or a group of formula —CO—$R^{11}$, —CO—$OR^{12}$ or —CO—$NHR^{13}$ where $R^{11}$, $R^{12}$ and $R^{13}$ each independently represent a moiety which is capable of binding to the minor groove of DNA.

11. A compound according to claim 10 wherein Y represents a phenyl, methoxyphenyl, hydroxymethylphenyl, aminomethylphenyl, propylaminomethylphenyl, hexylaminomethylphenyl, sulfanylmethylphenyl, dioxoisoindolinylmethylphenyl, hydroxyethoxyphenyl, hydroxypropoxyphenyl, carboxylmethoxyphenyl, ethanoylthiomethylphenyl, dimethylpropanoyloxyphenyl, (tert-butyldimethyl)silyloxyphenyl, (tert-butyldimethyl)silyloxymethylphenyl, (tert-butyldimethyl)silyloxyethoxyphenyl, (tert-butyldimethyl)silyloxypropoxyphenyl, (methoxyphenyl)methoxycarbonylmethoxyphenyl, naphthyl, pyridyl or quinolinyl group.

12. A compound according to claim 11 wherein Y represents a phenyl, 4-methoxyphenyl, 2-(hydroxymethyl)phenyl, 2-(aminomethyl)phenyl, 2-((n-propylamino)methyl)phenyl, 2-((n-hexylamino)methyl)phenyl, 2-(sulfanylmethyl)phenyl, ((1,3-dioxosoindolin-2-yl)methyl)phenyl, 4-(hydroxyethoxy)phenyl, 4-(hydroxypropoxy)phenyl, 4-(carboxylmethoxy)phenyl, 2-((ethanoylthio)methyl)phenyl, 4-(2,2-dimethylpropanoyloxy)phenyl, 4-((tert-butyldimethyl)siloxy)phenyl, 2-(((tert-butyldimethyl)silyloxy)methyl)phenyl, 4-(2-((tert-butyldimethyl)silyloxy)ethoxy)phenyl, 4-[((4-methoxybenzyloxy)carbonyl)methoxy]phenyl, 1-naphthyl, 2-naphthyl, pyrid-4-yl or quinolin-4-yl group.

13. A compound according to claim 1 of formula IB wherein X and Y together with the interjacent carbon atom represent a 3- to 18-membered heterocyclic group optionally substituted by one or more substituents selected from the group consisting of halogen atoms, nitro and hydroxyl groups and $C_{1-12}$ alkyl and $C_{1-12}$ alkoxy groups each optionally substituted by one or more substituents selected from the group consisting of halogen atoms, nitro and hydroxyl groups.

14. A compound according to claim 13 wherein X and Y together with the interjacent carbon atom represent a group of formula

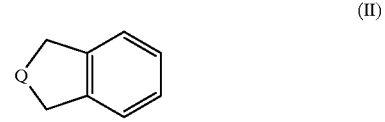

(II)

where Q represents an oxygen or sulphur atom or a group $NR^{14}$ and $R^{14}$ represents a hydrogen atom or a $C_{1-8}$ alkyl group optionally substituted by one or more substituents selected from halogen atoms and hydroxyl groups.

15. A compound according to claim 14 wherein $R^{14}$ represents a hydrogen atom or a methyl, propyl, hexyl or hydroxyethyl group.

16. A process for the preparation of a compound of the general formula IA as defined in claim 1 which comprises (a) either cyclizing a compound of the general formula

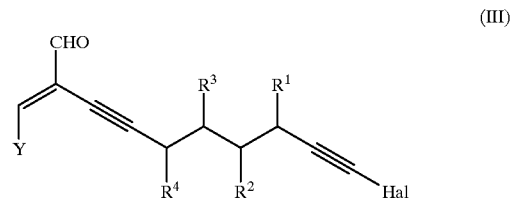

(III)

in which $R^1$, $R^2$, $R^3$, $R^4$ and Y are as defined in claim 1 and Hal represents a bromine or iodine atom, in the presence of a catalyst to form a compound of formula IA in which X represents a hydroxyl group and Y is as defined in claim 1, or cyclizing a compound of the general formula

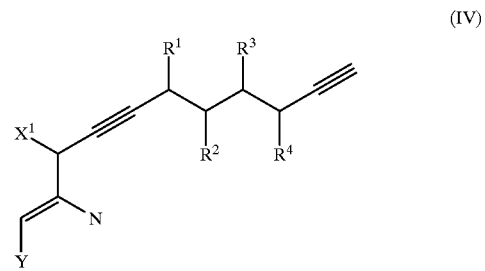

(IV)

in which $X^1$ represents a hydroxyl group or an optionally substituted alkoxy group, N represents a bromine or iodine atom or a trifluoromethanesulfonate group and, $R^1$, $R^2$, $R^3$, $R^4$ and Y is as defined in claim 1, in the presence of a catalyst to form a compound of formula IA in which X represents a hydroxyl group or an optionally substituted alkoxy group and $R^1$, $R^2$, $R^3$, $R^4$ and Y are as defined in claim 1; and (b) if desired, reacting a compound of formula IA so formed in which X represents a hydroxyl group with a suitable carboxylic acid, acid anhydride and/or acid chloride in the presence of a catalyst to form a compound of formula IA in which X represents an optionally substituted acyloxy group and $R^1$, $R^2$, $R^3$, $R^4$ and Y are as defined in claim 1.

17. A process for the preparation of a compound of the general formula IB

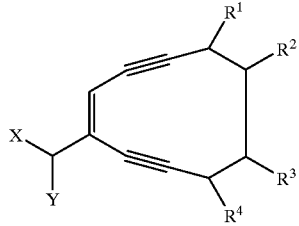

(IB)

in which X represents an optionally substituted acyloxy group and $R^1$, $R^2$, $R^3$, $R^4$ and Y or X and Y together are as defined in claim 1, which comprises reacting a compound of the general formula IA

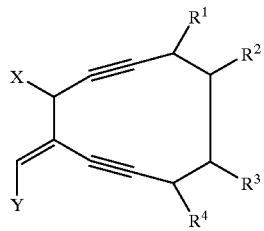

(IA)

in which X represents an optionally substituted acyloxy group and $R^1$, $R^2$, $R^3$, $R^4$ and Y are as defined in claim 1 in the presence of a lanthanide catalyst.

18. A process according to claim 17 wherein the lanthanide catalyst is of the formula $L(fod)_3$, where L represents a lanthanide metal and fod represents tris(6,6,7,7,8,8,8,-heptafluoro-2,2-dimethyl-3,5-octanedionate).

19. A process according to claim 18 wherein L represents a lanthanide metal selected from the group consisting of europium, praseodymium, erbium and ytterbium.

20. A process according to claim 19 wherein the lanthanide metal is europium.

21. A process for the preparation of a compound of the general formula

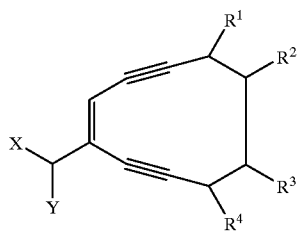

(IB)

in which X represents a hydroxyl group or an optionally substituted alkoxy group and $R^1$, $R^2$, $R^3$, $R^4$ and Y are as defined in claim 1, which comprises reacting a compound of the general formula

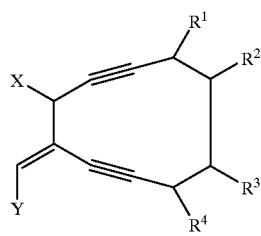

(IA)

in which X represents a hydroxyl group and $R^1$, $R^2$, $R^3$, $R^4$ and Y are as defined in claim 1, with a protic acid in the presence of a suitable alcohol or with a protic acid optionally in the presence of water.

22. A pharmaceutical composition which comprises a carrier and, as active ingredient, a compound of the general formula IA or IB as defined in claim 1 or a salt thereof.

23. A method for inhibiting tumor growth which comprises administering to a patient a therapeutically effective amount of a compound of the general formula IA or IB or a salt thereof as defined in claim 1.

24. A method for treating cancer which comprises administering to a patient a therapeutically effective amount of a compound of the general formula IA or IB or a salt thereof as defined in claim 1.

25. A method for inhibiting microbial growth which comprises administering to a patient a therapeutically effective amount of a compound of the general formula IA or IB or a salt thereof as defined in claim 1.

26. A method for cleaving DNA which comprises contacting DNA or target cells with a compound of the general formula IA or IB or a salt thereof as defined in claim 1.

27. A method for degrading or modulating a protein which comprises contacting the protein with a compound of the general formula IA or IB or a salt thereof as defined in claim 1.

28. A compound according to claim 2 wherein $R^1$ and $R^2$, $R^2$ and $R^3$ or $R^3$ and $R^4$ together with the interjacent carbon atoms represent a $C_{5-8}$ cycloalkyl group optionally substituted by one or more substituents selected from the group consisting of halogen atoms, nitro, hydroxyl, $C_{1-6}$ alkyl, $C_{1-6}$ alkoxy, $C_{1-6}$ haloalkoxy and oxy groups.

29. A method for inhibiting tumor growth which comprises administering to a patient a therapeutically effective amount of a pharmaceutical composition as defined in claim 22.

30. A method for treating cancer which comprises administering to a patient a therapeutically effective amount of a pharmaceutical composition as defined in claim 22.

31. A method for inhibiting microbial growth which comprises administering to a patient a therapeutically effective amount of a pharmaceutical composition as defined in claim 22.

32. A method for cleaving DNA which comprises contacting DNA or target cells with a pharmaceutical composition as defined in claim 22.

33. A method for degrading or modulating a protein which comprises contacting the protein with a pharmaceutical composition as defined in claim 22.

* * * * *